(12) United States Patent
Hartung et al.

(10) Patent No.: US 7,825,114 B2
(45) Date of Patent: Nov. 2, 2010

(54) SUBSTITUTED AMINOPYRAZOLOPYRIDINES AND SALTS THEREOF, PHARMACEUTICAL COMPOSITIONS COMPRISING SAME, METHODS OF PREPARING SAME AND USES OF SAME

(75) Inventors: Ingo Hartung, Berlin (DE); Stuart Ince, Berlin (DE); Georg Kettschau, Berlin (DE); Karl-Heinz Thierauch, Berlin (DE); Hans Briem, Bremen (DE); Wolfgang Schwede, Glienicke (DE); Antonius M. Laak Ter, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 676 days.

(21) Appl. No.: 11/761,621

(22) Filed: Jun. 12, 2007

(65) Prior Publication Data

US 2009/0018129 A1 Jan. 15, 2009

Related U.S. Application Data

(60) Provisional application No. 60/816,624, filed on Jun. 27, 2006, provisional application No. 60/891,103, filed on Feb. 22, 2007.

(30) Foreign Application Priority Data

Jun. 13, 2006 (EP) ................... 06090108
Feb. 22, 2007 (EP) ................... 07090024

(51) Int. Cl.
*A61K 31/5377* (2006.01)
*C07D 471/04* (2006.01)
*A61P 35/00* (2006.01)
*A61P 27/02* (2006.01)
*A61K 31/437* (2006.01)

(52) U.S. Cl. ............... 514/234.2; 514/303; 546/119; 544/127

(58) Field of Classification Search ............ 514/234.2, 514/303; 546/119; 544/127
See application file for complete search history.

(56) References Cited

U.S. PATENT DOCUMENTS
2006/0178378 A1* 8/2006 Dai et al. .............. 514/262.1

FOREIGN PATENT DOCUMENTS
WO WO 2004/113304 12/2004
WO WO 2006/050109 5/2006

OTHER PUBLICATIONS

D.H. Albert et al."Preclinical activity of ABT-869, a multitargeted receptor tyrosine kinase inhibitor", Molecular Cancer Therapeutics, American Association of Cancer Research, (Apr. 2006), pp. 995-1006.

* cited by examiner

*Primary Examiner*—D. Margaret Seaman
*Assistant Examiner*—Niloofar Rahmani
(74) *Attorney, Agent, or Firm*—Millen, White, Zelano & Branigan, P.C.

(57) ABSTRACT

The invention relates to substituted aminopyrazolopyridines according to the general formula (I):

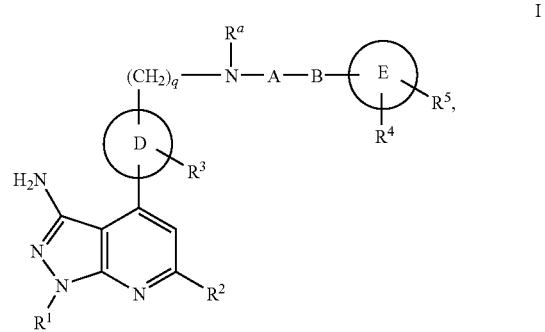

in which A, B, D, E, $R^a$, $R^1$, $R^2$, $R^3$, $R^4$, $R^5$ and q are as defined in the claims, and salts thereof, to pharmaceutical compositions comprising said substituted aminopyrazolopyridines, to methods of preparing said substituted aminopyrazolopyridines as well as the use thereof for manufacturing a pharmaceutical composition for the treatment of diseases of dysregulated vascular growth or of diseases which are accompanied with dysregulated vascular growth, wherein the compounds effectively interfere with Tie2 signalling.

35 Claims, No Drawings

SUBSTITUTED AMINOPYRAZOLOPYRIDINES AND SALTS THEREOF, PHARMACEUTICAL COMPOSITIONS COMPRISING SAME, METHODS OF PREPARING SAME AND USES OF SAME

This application claims the benefit of the filing dates of U.S. Provisional Application Ser. No. 60/816,624 filed Jun. 27, 2006 and U.S. Provisional Application Ser. No. 60/891,103 filed Feb. 22, 2007, which are incorporated by reference herein.

The present invention relates to substituted aminopyrazolopyridine compounds of general formula (I) and salts thereof, to pharmaceutical compositions comprising said substituted aminopyrazolopyridine compounds, to methods of preparing said substituted aminopyrazolopyridines, as well as to uses thereof.

SCIENTIFIC BACKGROUND

Dysregulated vascular growth plays a critical role in a variety of inflammatory diseases, in particular psoriasis, delayed type hypersensitivity, contact dermatitis, asthma, multiple sclerosis, restenosis, rheumatoid arthritis and inflammatory bowl disease. Aberrant vascular growth is also involved in neovascular ocular diseases such as age-related macular degeneration and diabetic retinopathy. Additionally, sustained vascular growth is accepted as one hallmark of cancer development (Hanahan, D.; Weinberg, R. A. *Cell* 2000, 100, 57). While tumours initially grow either as an avascular mass or by co-opting existing host vessels, growth beyond a few $mm^3$ in size is depending on the induction of vessel neogrowth in order to sufficiently provide the tumour with oxygen and nutrients. Induction of angiogenesis is a prerequisite that the tumour surpasses a certain size (the so called angiogenic switch). An intricate signalling interaction network between cancer cells and the tumour microenvironment triggers the induction of vessel growth from existing vasculature. The dependence of tumours on neovascularization has led to a new treatment paradigm in cancer therapy (Ferrara et al. *Nature* 2005, 438, 967; Carmeliet *Nature* 2005, 438, 932). Blocking tumour neovascularization by small molecule or antibody-mediated inhibition of relevant signal transduction pathways holds a great promise for extending currently available therapy options.

The development of the cardiovascular system involves two basic stages. In the initial vasculogenesis stage, which only occurs during embryonal development, angioblasts differentiate into endothelial cells which subsequently form a primitive vessel network. The subsequent stage, termed angiogenesis, involves the remodeling of the initial vasculature and sprouting of new vessels (Risau, W. *Nature* 1997, 386, 671; Jain, R. K. *Nat. Med.* 2003, 9, 685). Physiologically, angiogenesis occurs in wound healing, muscle growth, the female cycle and in the above mentioned disease states.

It has been found that receptor tyrosine kinases of the vascular endothelial growth factor (VEGF) family and the Tie (tyrosine kinase with immunoglobulin and epidermal growth factor homology domain) receptor tyrosine kinases are essential for both developmental and disease-associated angiogenesis (Ferrara et al *Nat. Med.* 2003, 9, 669; Dumont et al. *Genes Dev.* 1994, 8, 1897; Sato et al. *Nature* 1995, 376, 70).

In adults the Tie2 receptor tyrosine kinase is selectively expressed on endothelial cells (EC) of the adult vasculature (Schlaeger et al. *Proc. Nat. Acad. Sci. USA* 1997, 94, 3058). Immunohistochemical analysis demonstrated the expression of Tie2 in adult rat tissues undergoing angiogenesis. During ovarian folliculogenesis, Tie2 is expressed in neovessels of the developing corpus luteum. Four endogeneous ligands—angiopoietins 1 to 4—have been identified for the type 1 transmembrane Tie2 (also named Tek) receptor, while no ligands have been identified so far for the Tie1 receptor. Binding of the extracellular Tie2 domain to the C-terminal fibrinogen-like domains of the various angiopoietins leads to significantly different cellular effects. In addition, heterodimerizations between Tie1 and Tie2 receptors have been postulated to influence ligand binding.

Binding of Ang1 to Tie2 expressed on EC induces receptor cross-phosphorylation and kinase activation thus triggering various intracellular signalling pathways. The intracellular C-terminal tail of the Tie2 protein plays a crucial role in Tie2 signalling (Shewchuk et al. *Structure* 2000, 8, 1105). Upon ligand binding, a conformational change is induced which removes the C-tail out of its inhibitory conformation thus allowing kinase activation by cross-phoshorylation of various Tyr residues in the C-tail, which subsequently function as docking sites for phosphotyrosine-binding (PTB) site possessing down-stream mediators. Cellular effects initiated by Ang1 activation of Tie2 include inhibition of EC apoptosis, stimulation of EC migration and blood vessel reorganization, suppression of inflammatory gene expression and suppression of vascular permeability (Brindle et al. *Circ. Res.* 2006, 98, 1014). In contrast to VEGF-VEGFR signalling in EC, Ang1 activation of Tie2 does not stimulate EC proliferation in the majority of published assay settings.

The anti-apoptotic effect of Tie2 signalling was shown to be mediated mainly by the PI3K-Akt signalling axis which is activated by binding of the regulatory p85 subunit of PI3K to Y1102 in the Tie2 C-tail (DeBusk et al. *Exp. Cell. Res.* 2004, 298, 167; Papapetropoulos et al. *J. Biol. Chem.* 2000, 275, 9102; Kim et al. *Circ. Res.* 2000, 86, 24). In contrast, the chemotactic response downstream of the activated Tie2 receptor requires crosstalk between PI3K and the adaptor protein Dok-R. Membrane localization of Dok-R via binding of its pleckstrin homology (PH) domain to PI3K and simultaneous binding to Y1108 in the Tie2 C-tail via its PTB domain leads to Dok-R phoshorylation and downstream signalling via Nck and Pak-1 (Jones et al. *Mol. Cell. Biol.* 2003, 23, 2658; Master et al. *EMBO J.* 2001, 20, 5919). PI3K-mediated recruitment of the adaptor protein ShcA to Y1102 of the Tie2 C-tail is also believed to induce cellular sprouting and motility effects involving activation of endothelial nitric oxide synthase (eNOS), focal adhesion kinase (FAK) and the GTPases RhoA and Rac1. Other downstream mediators of Tie2 signalling include the adaptor protein Grb2, which mediates Erk1/2 stimulation, and the SHP-2 phosphatase.

In conclusion, basal activation of the Tie2 pathway by Ang1 is believed to maintain quiescence and integrity of the endothelium of the adult vasculature by providing a cell survival signal for ECs and by maintaining the integrity of the EC lining of blood vessels (Peters et al. *Recent Prog. Horm. Res.* 2004, 59, 51).

In contrast to Ang1, Ang2 is not able to activate Tie2 on EC unless Ang2 is present in high concentration or for prolonged periods. However, Ang2 functions as a Tie2 agonist in non-endothelial cells transfected with Tie2. The structural basis for this context-dependence of the Ang2-Tie2 interaction is to date not understood.

In endothelial cells, however, Ang2 functions as Tie2 antagonist and thus blocks the agonistic activity of Ang1 (Maisonpierre et al. *Science* 1997, 277, 55). Ang2 binding to Tie2 prevents Ang1-mediated Tie2 activation which leads to vessel destabilization and results in vessel regression in the absence of pro-angiogenic stimuli such as VEGF. While Ang1 is widely expressed by periendothelial cells in quiescent vasculature such as pericytes or smooth muscle cells, Ang2 expression occurs in areas of ongoing angiogenesis. Ang2 can be stored in Weibel-Palade bodies in the cytoplasm of EC allowing for a quick vascular response upon stimulation.

Ang1 and Ang2 are expressed in the corpus luteum, with Ang2 localizing to the leading edge of proliferating vessels and Ang1 localizing diffusively behind the leading edge. Ang2 expression is inter alia initiated by hypoxia (Pichiule et al. *J. Biol. Chem.* 2004, 279, 12171). Ang2 is upregulated in the tumour vasculature and represents one of the earliest tumour markers. In the hypoxic tumour tissue, Ang2 expression induces vessel permeability and—in the presence of e.g. pro-angiogenic VEGF—triggers angiogenesis. After VEGF mediated EC proliferation and vessel sprouting maturation of the newly formed vessels again necessitates Tie2 activation by Ang1. Therefore, a subtle balancing of Tie2 activity plays a pivotal role in the early as well as late stages of neovascularization. These observations render the Tie2 RTK an attractive target for anti-angiogenesis therapy in diseases caused by or associated with dysregulated vascular growth. However, it remains to be shown if targeting the Tie2 pathway alone will be sufficient to achieve efficacious blockade of neovascularization. In certain diseases or disease subtypes it might be necessary or more efficacious to block several angiogenesis-relevant signalling pathways simultaneously.

Various theories have been discussed to explain the differential effects of Ang1 and Ang2 on Tie2 downstream signalling events. Binding of Ang1 and Ang2 in a structurally different manner to the Tie2 ectodomain could induce ligand-specific conformational changes of the intracellular kinase domain explaining different cellular effects. Mutational studies however point toward similar binding sites of Ang1 and Ang2. In contrast, various publications have focussed on different oligomerization states of Ang1 vs. Ang2 as basis for different receptor multimerization states upon ligand binding. Only Ang1 present in its tetramer or higher-order structure initiates Tie2 activation in EC while Ang2 was reported to exist as a homodimer in its native state (Kim et al. *J. Biol. Chem.* 2005, 280, 20126; Davis et al. *Nat. Struc. Biol.* 2003, 10, 38; Barton et al. *Structure* 2005, 13, 825). Finally, specific interactions of Ang1 or Ang2 with additional cell-specific co-receptors could be responsible for the different cellular effects of Ang1 vs. Ang2 binding to Tie2. Interaction of Ang1 with integrin α5β1 has been reported to be essential for certain cellular effects (Carlson et al. *J. Biol. Chem.* 2001, 276, 26516; Dallabrida et al. *Circ. Res.* 2005, 96, e8). Integrin α5β1 associates constitutively with Tie2 and increases the receptor's binding affinity for Ang1 resulting in initiation of downstream signalling at lower Ang1 effector concentrations in situations where integrin α5 β1 is present. The recently solved crystal structure of the Tie2-Ang2 complex suggests however that neither the oligomerization state nor a different binding mode causes the opposing cellular effects (Barton et al. *Nat. Struc. Mol. Biol.* 2006, advance online publication).

Ang1-Tie2 signalling plays also a role in the development of the lymphatic system and in lymphatic maintenance and sprouting (Tammela et al. *Blood* 2005, 105, 4642). An intimate cross-talk between Tie2 and VEGFR-3 signalling in lymphangiogenesis seems to equal the Tie2-KDR cross-talk in blood vessel angiogenesis.

A multitude of studies have underscored the functional significance of Tie2 signalling in the development and maintenance of the vasculature. Disruption of Tie2 function in Tie2$^{-/-}$ transgenic mice leads to early embryonic lethality between days 9.5 and 12.5 as a consequence of vascular abnormalities. Tie2$^{-/-}$ embryos fail to develop the normal vessel hierachy suggesting a failure of vascular branching and differentiation. The heart and vessels in Tie2$^{-/-}$ embryos show a decreased lining of EC and a loosened interaction between EC and underlying pericyte/smooth muscle cell matrix. Mice lacking functional Ang1 expression and mice overexpressing Ang2 display a phenotype reminiscent of the phenotype of Tie2$^{-/-}$ mice (Suri et al. *Cell* 1996, 87, 1171). Ang2$^{-/-}$ mice have profound defects in the growth and patterning of lymphatic vasculature and fail to remodel and regress the hyaloid vasculature of the neonatal lens (Gale et al. *Dev. Cell* 2002, 3, 411). Ang1 rescued the lymphatic defects, but not the vascular remodeling defects. Therefore, Ang2 might function as a Tie2 antagonist in blood vasculature but as a Tie2 agonist in developing lymph vasculature suggesting redundant roles of Ang1 and Ang2 in lymphatic development.

Aberrant activation of the Tie2 pathway is involved in various pathological settings. Activating Tie2 mutations leading to increased ligand-dependent and ligand-independent Tie2 kinase activity cause inherited venous malformations (Vikkula et al. *Cell* 1996, 87, 1181). Increased Ang1 mRNA and protein levels as well as increased Tie2 activation have been reported in patients with pulmonary hypertension (PH). Increased pulmonary arterial pressure in PH patients results from increased coverage of pulmonary arterioles with smooth muscle cells (Sullivan et al. *Proc. Natl. Acad. Sci. USA* 2003, 100, 12331). In chronic inflammatory diseases, like in psoriasis, Tie2 and the ligands Ang1 and Ang2 are greatly upregulated in lesions, whereas a significant decrease in expression of Tie2 and ligands occur under anti-psoriatic treatment (Kuroda et al. *J. Invest. Dermatol* 2001, 116, 713). Direct association of pathogenesis of disease with Tie2 expression has been demonstrated recently in transgenic mice overexpressing Tie2 (Voskas et al. *Am. J. Pathol.* 2005, 166, 843). In these mice overexpression of Tie2 causes a psoriasis-like phenotype (such as epidermal thickening, rete ridges and lymphocyte infiltration). These skin abnormalities are resolved completely upon suppression of transgene expression, thereby illustrating a complete dependence on Tie2 signalling for disease maintenance and progression.

Tie2 expression was investigated in human breast cancer specimens and Tie2 expression was found in the vascular endothelium both in normal breast tissue as well as in tumour tissue. The proportion of Tie2-positive microvessels was increased in tumours as compared to normal breast tissue (Peters et al. *Br. J. Canc.* 1998, 77, 51). However, significant heterogeneity in endothelial Tie2 expression was observed in clinical specimen from a variety of human cancers (Fathers et al. *Am. J. Path.* 2005, 167, 1753). In contrast, Tie2 and angiopoietins were found to be highly expressed in the cytoplasm of human colorectal adenocarcinoma cells indicating at the potential presence of an autocrine/paracrine growth loop in certain cancers (Nakayama et al. *World J. Gastroenterol.* 2005, 11, 964). A similar autocrine/paracrine Ang1-Ang2-Tie2 loop was postulated for certain human gastric cancer cell lines (Wang et al. *Biochem. Biophys. Res. Comm.* 2005, 337, 386).

The relevance of the Ang1-Tie2 signalling axis was challenged with various biochemical techniques. Inhibition of Ang1 expression by an antisense RNA approach resulted in decreased xenograft tumour growth (Shim et al. *Int. J. Canc.* 2001, 94, 6; Shim et al. *Exp. Cell Research* 2002, 279, 299). However, other studies report that experimental overexpression of Ang1 in tumour models leads to decreased tumour growth (Hayes et al. *Br. J. Canc.* 2000, 83, 1154; Hawighorst et al. *Am. J. Pathol.* 2002, 160, 1381; Stoeltzing et al. *Cancer Res.* 2003, 63, 3370). The latter results can be rationalized by the ligand's ability to stabilize the endothelial lining of vessels rendering vessels less sensitive for angiogenic stimuli. Interference with the dynamics of Ang1-Tie2 signalling either by over-stimulation or by stimulus deprivation seemingly leads to similar phenotypes.

The pharmacological relevance of inhibiting Tie2 signalling was tested applying various non-small molecule approaches. A peptidic inhibitor of Ang1/2 binding to Tie2 was shown to inhibit Ang1-induced HUVEC migration and angiogenesis induction in an in vivo model (Tournaire et al. *EMBO Rep.* 2005, 5, 1). Corneal angiogenesis induced by tumour cell conditioned medium was inhibited by a recombinant soluble Tie2 receptor (sTie2) despite the presence of VEGF (Lin et al. *J. Clin. Invest.* 1997, 100, 2072; see also Singh et al. *Biochem. Biophys. Res. Comm.* 2005, 332, 194). Gene therapy by adenoviral vector delivered sTie2 was capable of reducing tumour growth rates of a murine mammary carcinoma and a murine melanoma and resulted in reduction of metastasis formation (Lin et al. *Proc. Natl. Acad. Sci. USA* 1998, 95, 8829). Similar effects were observed with related sTie2 constructs (Siemeister et al. *Cancer Res.* 1999, 59, 3185) and a Tek-Fc construct (Fathers et al. *Am. J. Path.* 2005, 167, 1753). Adenovirus-delivered anti-Tie2 intrabodies were shown to inhibit growth of a human Kaposi's sarcoma and a human colon carcinoma upon peritumoural administration (Popkov et al. *Cancer Res.* 2005, 65, 972). Histopathological analysis revealed a marked decrease in vessel density in treated vs. control tumours. Phenotypic simultaneous knockout of KDR and Tie2 by an adenovirus delivered intradiabody resulted in significantly higher growth inhibition of a human melanoma xenograft model than KDR knockout alone (Jendreyko et al. *Proc. Natl. Acad. Sci. USA* 2005, 102, 8293). Similarly, the bispecific Tie2-KDR intradiabody was more active in an in vitro EC tube formation inhibition assay than the two monospecific intrabodies alone (Jendreyko et al. *J. Biol. Chem.* 2003, 278, 47812). Systematic treatment of tumour-bearing mice with Ang2-blocking antibodies and peptide-Fc fusion proteins led to tumour stasis and elimination of tumour burden in a subset of animals (Oliner et al. *Cancer Cell* 2004, 6, 507). For a recent report on an immunization approach, see Luo et al. *Clin. Cancer Res.* 2006, 12, 1813.

However, from the above studies using biochemical techniques to interfere with Tie2 signalling it is not clear, whether similar phenotypes will be observed with small molecule inhibitors of the Tie2 kinase activity. Small molecule inhibitors of kinases by definition block only those cellular effects which are mediated by the receptor's kinase activity and not those which might involve the kinase only as a co-receptor or scaffolding component in multi-enzyme complexes. So far, only a single study using a small molecule Tie2 inhibitor has been published (Scharpfenecker et al. *J. Cell Sci.* 2005, 118, 771). It remains to be shown that small molecule inhibitors of the Tie2 kinase will be as efficacious in inhibiting angiogenesis as e.g. ligand antibodies, soluble decoy receptors or receptor intrabodies. As discussed above, in certain settings inhibition of Tie2 signalling alone might not be sufficient to induce an adequate antiangiogenic effect. Simultaneous inhibition of several angiogenesis relevant signalling pathways could overcome such inadequacies. In conclusion, there is a great need for novel chemotypes for small molecule inhibitors of the Tie2 kinase. Fine tuning of additive anti-angiogenic activities as well as pharmacokinetic parameters such as e.g. solubility, membrane permeability, tissue distribution and metabolism will finally allow for chosing compounds of accurate profiles for various diseases caused by or associated with dysregulated vascular growth.

PRIOR ART

To date, a small number of therapeutic agents with antiangiogenic activity have been approved for cancer treatment. Avastin (Bevacizumab), a VEGF neutralizing antibody, blocks KDR and VEGFR1 signalling and has been approved for first-line treatment of metastatic colorectal cancer. The small molecule multi-targeted kinase inhibitor Nexavar (Sorafenib) inhibits inter alia members of the VEGFR family and has been approved for the treatment of advanced renal cell carcinoma. Sutent (Sunitinib), another multi-targeted kinase inhibitor with activity vs. VEGFR family members, has been approved by the FDA for treatment of patients with gastrointestinal stromal tumours (GIST) or advanced kidney tumours. Several other small molecule inhibitors of angiogenesis-relevant targets are in clinical and pre-clinical development.

AMG-386, an angiopoietin-targeting recombinant Fc fusion protein, is in phase I clinical development in patients with advanced solid tumours. Several multi-targeted small molecule inhibitors with activity against Tie2 are (or have been) in preclinical evaluation for cancer therapy, including ABT-869, GW697465A and A-422885.88 (BSF466895). The first and most recent compound, however, was reported to possess higher inhibitory activity against other kinase targets including non-angiogenesis kinases and oncogenic kinases. This agent is therefore not considered to be a purely antiangiogenic agent and its applicability to non-cancer diseases remains to be shown.

Pyrazolopyridines have been disclosed as antimicrobiotic substances (e.g. Attaby et al., *Phosphorus, Sulphur and Silicon and the related Elements* 1999, 149, 49-64; Goda et al. *Bioorg. Med. Chem.* 2004, 12, 1845). A single 3-amino-1H-pyrazolo[3,4-b]pyridine with modest EGFR inhibitory activity has been published by Cavasotto et al. (*Bioorg. Med. Chem. Lett.* 2006, 16, 1969). 5-aryl-1H-3-aminopyrazolo[3,4-b]pyridines have been reported as GSK-3 inhibitors (Witherington et al. *Bioorg. Med. Chem. Lett.* 2003, 13, 1577). WO 2003068773 discloses 3-acylaminopyrazolopyridine derivatives as GSK-3 inhibitors.

DE2232038 and DE2160780 disclose 3-amino-pyrazolo [3,4-b]pyridines i.a. as intermediates for the preparation of azo-dyes.

U.S. Pat. No. 4,224,322, U.S. Pat. No. 4,260,621 and DE2643753 further disclose 3-Amino-pyrazolo[3,4-b]pyridines as antithrombotic substances.

U.S. Pat. No. 5,478,830 further discloses fused heterocycles for the treatment of atherosclerosis.

WO 2001019828 discloses 125 templates, including 3-amino-1H-pyrazolopyridines, as modulators of the activity of receptor and non-receptor tyrosine and serine/threonine kinases.

WO 2002024679 discloses tetrahydropyridine-substituted pyrazolopyridines as IKK inhibitors.

WO 2004076450 further discloses 5-heteroaryl-pyrazolopyridines as p38 inhibitors.

WO 2004113304 discloses indazoles, benzisoxazoles and benzisothiazoles as inhibitors of protein tyrosine kinases, particularly of KDR kinase. However, an exemplary compound from this patent (termed Abt-869; see above) is reported to be ~40 times less active against Tie2 vs. KDR in enzymatic assays and even ~1000 times less active against Tie2 than KDR in cellular assays (Albert et al. *Mol. Cancer. Ther.* 2006, 5, 995).

WO 2006/050109 discloses pyrazolopyridines as protein tyrosine kinase inhibitors, particularly as KDR kinase inhibitors.

TECHNICAL PROBLEM TO BE SOLVED

There is a high demand for compounds which can be used not only as potent inhibitors of Tie-2 kinase, in particular inhibitors not only of the isolated kinase domain, but more importantly of cellular Tie-2 autophosphorylation, for the treatment of diseases of dysregulated vascular growth or diseases which are accompanied with dysregulated vascular growth, but which optionally also display inhibition of a further kinase, the inhibition of which is in response to particular therapeutic needs. Said further kinase may mediate e.g. angiogenesis, inflammation, or may be involved in oncological diseases. More specifically, inhibition of Tie2 or said further kinase can be tuned according to the appropriate therapeutic needs. Such pharmacological profiles are highly desirable for treating diseases of dysregulated vascular growth or diseases which are accompanied with dysregulated vascular growth, in particular solid tumours and metastases thereof, and also for treating non-oncological diseases of dysregulated vascular growth or non-oncological diseases which are accompanied with dysregulated vascular growth, such as retinopathy, other angiogenesis dependent diseases of the eye, in particular cornea transplant rejection or age-related macular degeneration, rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and diseases of the bowel, diseases such as coronary and peripheral artery disease. For example, simultaneous inhibition of Tie2 kinase and cKIT kinase would be of particular therapeutic use for the treatment of neoplastic disesases driven by cKIT kinase activity. In contrast, inhibition of cKIT may lead to side effects which are not acceptable in the treatment of non-oncological diseases. Therefore it would be highly desirable to have a class of compounds at one's disposal of potent Tie2 inhibitors which allow for tunability of the additional e.g. cKIT inhibitory activity in response to the particular disease to be treated.

DESCRIPTION OF THE INVENTION

The solution to the above-mentioned novel technical problem is achieved by providing compounds derived, in accordance with the present invention, from a class of substituted aminopyrazolopyridines and salts thereof, methods of preparing substituted aminopyrazolopyridines, a pharmaceutical composition containing said substituted aminopyrazolopyridines, use of said substituted aminopyrazolopyridines and a method for treating diseases with said substituted aminopyrazolopyridines, all in accordance with the description, as defined in the claims of the present application.

The present invention thus relates to compounds of general formula (I):

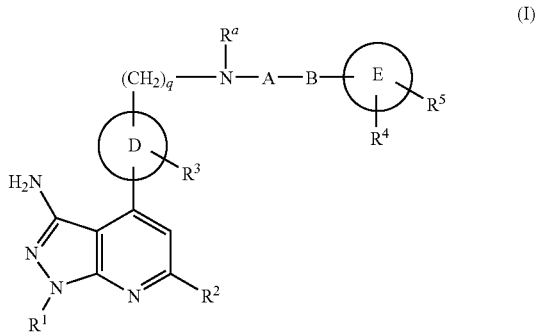

(I)

in which $R^1$ represents —C(O)$R^b$ or is selected from the group comprising, preferably consisting of, $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, wherein said residues are unsubstituted or substituted one or more times, independently from each other, with $R^6$;

$R^2$ represents a $C_3$-$C_{10}$-cycloalkyl optionally substituted with $R^7$;

$R^3$ is selected from the group comprising, preferably consisting of, hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen, cyano;

$R^4$, $R^5$, $R^6$, $R^7$, $R^8$ independently from each other, are selected from the group comprising, preferably consisting of, hydrogen, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)$R^b$, —S(O)$_2R^b$, —O$R^c$, —N$R^{d1}$, $R^{d2}$, —OP(O)(O$R^c$)$_2$, wherein $C_1$-$C_6$-alkyl, $C_3$-$C_{10}$-heterocycloalkyl and $C_3$-$C_{10}$-cycloalkyl of $R^4$, $R^5$, $R^6$, and $R^7$, are optionally substituted one or more times, in the same way or differently, with $R^8$, and wherein $C_1$-$C_6$-alkyl, $C_3$-$C_{10}$-heterocycloalkyl and $C_3$-$C_{10}$-cycloalkyl of $R^8$, are optionally substituted once with $R^8$;

$R^a$ is selected from the group comprising, preferably consisting of, hydrogen or $C_1$-$C_6$-alkyl;

$R^b$ is selected from the group comprising, preferably consisting of, hydroxyl, —O$R^c$, —S$R^c$, —N$R^{d1}R^{d2}$, aryl and $C_1$-$C_6$-alkyl;

$R^c$ is selected from the group comprising, preferably consisting of, hydrogen, —C(O)$R^b$, $C_1$-$C_6$-alkyl, $C_1$-$C_6$-haloalkyl, $C_3$-$C_{10}$-cycloalkyl, $C_3$-$C_{10}$-heterocycloalkyl, wherein $C_1$-$C_6$-alkyl, $C_1$-$C_6$-haloalkyl, $C_3$-$C_{10}$-cycloalkyl, $C_3$-$C_{10}$-heterocycloalkyl are optionally substituted one or more times, in the same way or differently, with hydroxyl, halogen, aryl, or —N$R^{d1}R^{d2}$, and wherein $C_1$-$C_6$-alkyl, $C_1$-$C_6$-haloalkyl, $C_3$-$C_{10}$-cycloalkyl, $C_3$-$C_{10}$-heterocycloalkyl are optionally substituted once with —O$R^c$, or —OP(O)(O$R^c$)$_2$;

$R^{d1}$, $R^{d2}$ independently from each other are selected from the group comprising, preferably consisting of hydrogen, $C_1$-$C_6$-alkyl, $C_3$-$C_{10}$-cycloalkyl, $C_3$-$C_{10}$-heterocycloalkyl, aryl, heteroaryl, or for a —C(O)$R^c$, —S(O)$_2R^b$, or —C(O)N$R^{d1}R^{d2}$ group, wherein $C_1$-$C_6$-alkyl, $C_3$-$C_{10}$-cycloalkyl, $C_3$-$C_{10}$-heterocycloalkyl are optionally substituted one or more times, in the same way or differently, with halogen, hydroxy or an —O$R^c$, —C(O)$R^b$, —S(O)$_2R^b$, —OP(O)(O$R^c$)$_2$ group, and wherein $C_1$-$C_6$-alkyl, $C_3$-$C_{10}$-cycloalkyl, $C_3$-$C_{10}$-heterocycloalkyl are optionally substituted once with an —N$R^{d1}R^{d2}$ group; or $R^{d1}$ and $R^{d2}$ together with the nitrogen atom to which they are attached, form a 3 to 10 membered heterocycloalkyl ring, whereby the carbon backbone of this heterocycloalkyl ring is optionally interrupted one or more times, in the same way or differently, by a member of the group comprising, preferably consisting of, NH, NR$^d$, oxygen or sulphur, and is optionally interrupted one or more times, in the same way or differently, with a —C(O)—, —S(O)—, and/or —S(O)$_2$— group, and optionally contains one or more double bonds;

A is selected from the group comprising, preferably consisting of, —C(O)—, —C(S)—, —C(=N$R^a$)—, —C(O)N$R^a$, —C(=N$R^a$)N$R^a$—, —S(O)$_2$—, —S(O)(=N$R^a$)—, —S(=N$R^a$)$_2$—, —C(S)N$R^a$—, —C(O)C(O)—, —C(O)C(O)N$R^a$—, —C(O)N$R^a$C(O)—, —C(S)N$R^a$C(O)—, and —C(O)N$R^a$C(S)—;

B is a bond or a group selected from the group comprising, preferably consisting of $C_1$-$C_6$-alkylene, $C_3$-$C_{10}$-cycloalkylene, $C_3$-$C_{10}$-heterocycloalkylene;

D, E are, independently from each other, arylene or heteroarylene and q represents an integer of 0, 1, or 2 or a salt or an N-oxide, thereof, wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

In accordance with a preferred embodiment, the present invention relates to compounds of general formula (I), in which:

$R^1$ represents —C(O)$R^b$ or is selected from the group comprising, preferably consisting of, $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, wherein said residues are unsubstituted or substituted one or more times, independently from each other, with $R^6$;

$R^2$ represents a $C_3$-$C_{10}$-cycloalkyl optionally substituted with $R^7$;

$R^3$ is selected from the group comprising, preferably consisting of, hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen, cyano $R^4$, $R^5$, $R^6$, $R^7$, $R^8$ independently from each other, are selected from the group comprising, preferably consisting of, hydrogen, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)$R^b$, —S(O)$_2R^b$, —OR$^c$, —NR$^{d1}R^{d2}$, —OP(O)(OR$^c$)$_2$, wherein $C_1$-$C_6$-alkyl, $C_3$-$C_{10}$-heterocycloalkyl and $C_3$-$C_{10}$-cycloalkyl of $R^4$, $R^5$, $R^6$, and $R^7$, are optionally substituted one or more times with $R^8$, and wherein $C_1$-$C_6$-alkyl, $C_3$-$C_{10}$-heterocycloalkyl and $C_3$-$C_{10}$-cycloalkyl of $R^8$, are optionally substituted once with $R^8$;

$R^a$ is selected from the group comprising, preferably consisting of, hydrogen or $C_1$-$C_6$-alkyl;

$R^b$ is selected from the group comprising, preferably consisting of, hydroxyl, —OR$^c$, —SR$^c$, —NR$^{d1}R^{d2}$, aryl and $C_1$-$C_6$-alkyl;

$R^c$ is selected from the group comprising, preferably consisting of, hydrogen, —C(O)$R^b$, $C_1$-$C_6$-alkyl, $C_1$-$C_6$-haloalkyl, $C_3$-$C_{10}$-cycloalkyl, $C_3$-$C_{10}$-heterocycloalkyl, wherein $C_1$-$C_6$-alkyl, $C_1$-$C_6$-haloalkyl, $C_3$-$C_{10}$-cycloalkyl, $C_3$-$C_{10}$-heterocycloalkyl are optionally substituted one or more times, in the same way or differently, with hydroxyl, halogen, aryl, or —NR$^{d1}R^{d2}$, and wherein $C_1$-$C_6$-alkyl, $C_1$-$C_6$-haloalkyl, $C_3$-$C_{10}$-cycloalkyl, $C_3$-$C_{10}$-heterocycloalkyl are optionally substituted once with —OR$^c$, or —OP(O)(OR$^c$)$_2$;

$R^{d1}$, $R^{d2}$ independently from each other are selected from the group comprising, preferably consisting of hydrogen, $C_1$-$C_6$-alkyl, $C_3$-$C_{10}$-cycloalkyl, $C_3$-$C_{10}$-heterocycloalkyl, aryl, heteroaryl, or for a group —C(O)$R^c$, —S(O)$_2R^b$, or —C(O)NR$^{d1}R^{d2}$, wherein $C_1$-$C_6$-alkyl, $C_3$-$C_{10}$-cycloalkyl, $C_3$-$C_{10}$-heterocycloalkyl are optionally substituted one or more times, in the same way or differently, with halogen, hydroxy or an —OR$^c$, —C(O)$R^b$, —S(O)$_2R^b$, —OP(O)(OR$^c$)$_2$ group, and wherein $C_1$-$C_6$-alkyl, $C_3$-$C_{10}$-cycloalkyl, $C_3$-$C_{10}$-heterocycloalkyl are optionally substituted once with the group —NR$^{d1}R^{d2}$; or $R^{d1}$ and $R^{d2}$ together with the nitrogen atom to which they are attached, form a 3 to 10 membered heterocycloalkyl ring, whereby the carbon backbone of this heterocycloalkyl ring is optionally interrupted one or more times, the same way or differently, by a member of the group comprising, preferably consisting of, NH, NR$^{d1}$, oxygen or sulphur, and is optionally interrupted one or more times, the same way or differently, with a —C(O)—, —S(O)—, and/or —S(O)$_2$— group, and optionally contains one or more double bonds;

A is selected from the group comprising, preferably consisting of, —C(O)—, —C(O)NR$^a$—, —S(O)$_2$—, —C(S)NR$^a$—, —C(O)C(O)—C(O)C(O)NR$^a$—, —C(O)NR$^a$C(O)—, —C(S)NR$^a$C(O)—, and —C(O)NR$^a$C(S)—;

B is a bond or a group selected from the group comprising, preferably consisting of $C_1$-$C_6$-alkylene, $C_3$-$C_{10}$-cycloalkylene, $C_3$-$C_{10}$-heterocycloalkylene;

D is phenylene;

E is phenylene or 5- or 6-membered heteroarylene;

and q represents an integer of 0 or 1 wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

In accordance with a particularly preferred embodiment, the present invention relates to compounds of general formula (I), in which:

$R^1$ represents —C(O)$R^b$ or is selected from the group comprising, preferably consisting of, $C_1$-$C_6$-alkyl, $C_3$-$C_{10}$-cycloalkyl, $C_3$-$C_{10}$-heterocycloalkyl, wherein said residues are unsubstituted or substituted one or more times, independently from each other, with $R^6$;

$R^2$ represents a $C_3$-$C_{10}$-cycloalkyl optionally substituted with $R^7$;

$R^3$ is selected from the group comprising, preferably consisting of, hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen, cyano $R^4$, $R^5$, $R^6$, $R^7$, $R^8$ independently from each other, are selected from the group comprising, preferably consisting of, hydrogen, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)$R^b$, —S(O)$_2R^b$, —OR$^c$, —NR$^{d1}R^{d2}$, —OP(O)(OR$^c$)$_2$, wherein $C_1$-$C_6$-alkyl, $C_3$-$C_{10}$-heterocycloalkyl and $C_3$-$C_{10}$-cycloalkyl of $R^4$, $R^5$, $R^6$, and $R^7$, are optionally substituted one or more times with $R^8$, and wherein $C_1$-$C_6$-alkyl, $C_3$-$C_{10}$-heterocycloalkyl and $C_3$-$C_{10}$-cycloalkyl of $R^8$, are optionally substituted once with $R^8$;

$R^a$ is selected from the group comprising, preferably consisting of, hydrogen or $C_1$-$C_6$-alkyl;

$R^b$ is selected from the group comprising, preferably consisting of, hydroxyl, —$OR^c$, —$SR^c$, —$NR^{d1}R^{d2}$, aryl and $C_1$-$C_6$-alkyl;

$R^c$ is selected from the group comprising, preferably consisting of, hydrogen, —$C(O)R^b$, $C_1$-$C_6$-alkyl, $C_1$-$C_6$-haloalkyl, $C_3$-$C_{10}$-cycloalkyl, $C_3$-$C_{10}$-heterocycloalkyl, wherein $C_1$-$C_6$-alkyl, $C_1$-$C_6$-haloalkyl, $C_3$-$C_{10}$-cycloalkyl, $C_3$-$C_{10}$-heterocycloalkyl are optionally substituted one or more times with hydroxyl, halogen, aryl, or —$NR^{d1}R^{d2}$, and wherein $C_1$-$C_6$-alkyl, $C_1$-$C_6$-haloalkyl, $C_3$-$C_{10}$-cycloalkyl, $C_3$-$C_{10}$-heterocycloalkyl are optionally substituted once with —$OR^c$, or —$OP(O)(OR^c)_2$;

$R^{d1}$, $R^{d2}$ independently from each other are selected from the group comprising, preferably consisting of hydrogen, $C_1$-$C_6$-alkyl, $C_3$-$C_{10}$-cycloalkyl, $C_3$-$C_{10}$-heterocycloalkyl, aryl, heteroaryl, or for a group —$C(O)R^c$, —$S(O)_2R^b$, or —$C(O)NR^{d1}R^{d2}$, wherein $C_1$-$C_6$-alkyl, $C_3$-$C_{10}$-cycloalkyl, $C_3$-$C_{10}$-heterocycloalkyl are optionally substituted one or more times, in the same way or differently, with halogen, hydroxy or an —$OR^c$, —$C(O)R^b$, —$S(O)_2R^b$, —$OP(O)(OR^c)_2$ group, and wherein $C_1$-$C_6$-alkyl, $C_3$-$C_{10}$-cycloalkyl, $C_3$-$C_{10}$-heterocycloalkyl are optionally substituted once with an —$NR^{d1}R^{d2}$ group; or $R^{d1}$ and $R^{d2}$ together with the nitrogen atom to which they are attached, form a 3 to 10 membered heterocycloalkyl ring, whereby the carbon backbone of this heterocycloalkyl ring is optionally interrupted one or more times, the same way or differently, by a member of the group comprising, preferably consisting of, NH, $NR^{d1}$, oxygen or sulphur, and is optionally interrupted one or more times, the same way or differently, with a —C(O)—, —S(O)—, and/or —$S(O)_2$— group, and optionally contains one or more double bonds;

A is selected from the group comprising, preferably consisting of, —C(O)—, —$C(O)NR^a$—, —$S(O)_2$—;

B is a bond or a group selected from the group comprising, preferably consisting of $C_1$-$C_6$-alkylene, $C_3$-$C_{10}$-cycloalkylene;

D is para-phenylene;

E is phenylene or 5- or 6-membered heteroarylene;

and q represents an integer of 0 or 1 wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

In accordance with a more particularly preferred embodiment, the present invention relates to compounds of general formula (I), in which $R^1$ represents —$C(O)R^b$ or is selected from the group comprising, preferably consisting of, $C_1$-$C_6$-alkyl, $C_3$-$C_6$-cycloalkyl, $C_3$-$C_6$-heterocycloalkyl, wherein said residues are unsubstituted or substituted one or more times, independently from each other, with $R^6$;

$R^2$ represents a $C_3$-$C_6$-cycloalkyl optionally substituted with $R^7$;

$R^3$ is selected from the group comprising, preferably consisting of, hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen, cyano;

$R^4$ is selected from the group comprising, preferably consisting of, hydrogen, $C_1$-$C_6$-alkyl, $C_1$-$C_6$-haloalkyl, $C_1$-$C_6$-haloalkoxy, hydroxy, amino, halogen, cyano, nitro, —$OR^c$, wherein $C_1$-$C_6$-alkyl is optionally substituted one or more times with $R^8$;

$R^5$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, cyano, nitro, —$C(O)R^b$, —$S(O)_2R^b$, —$OR^c$, —$NR^{d1}R^{d2}$, wherein $C_1$-$C_6$-alkyl and $C_3$-$C_6$-heterocycloalkyl are optionally substituted one or more times with $R^8$;

$R^6$ is selected from the group comprising, preferably consisting of, hydrogen, $C_3$-$C_6$-heterocycloalkyl, $C_1$-$C_6$-haloalkoxy, aryl, hydroxy, amino, cyano, —$C(O)R^b$, —$S(O)_2R^b$, —$OR^c$, —$NR^{d1}R^{d2}$, wherein $C_3$-$C_6$-heterocycloalkyl is optionally substituted one or more times with $R^8$;

$R^7$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, aryl, hydroxy, amino, cyano, —$C(O)R^b$, —$S(O)_2R^b$, —$OR^c$, —$NR^{d1}R^{d2}$, wherein $C_1$-$C_6$-alkyl and $C_3$-$C_6$-heterocycloalkyl are optionally substituted one or more times with $R^8$;

$R^8$ is selected from the group comprising, preferably consisting of, $C_1$-$C_6$-haloalkoxy, hydroxy, amino, cyano, halogen, —$C(O)R^b$, —$S(O)_2R^b$, —$OR^c$, —$NR^{d1}R^{d2}$;

$R^a$ is hydrogen $R^b$ is selected from the group comprising, preferably consisting of, —$OR^c$, —$NR^{d1}R^{d2}$, and $C_1$-$C_6$-alkyl;

$R^c$ is selected from the group comprising, preferably consisting of, hydrogen, $C_1$-$C_6$-alkyl, $C_3$-$C_6$-cycloalkyl, $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times, in the same way or differently, with —$NR^{d1}R^{d2}$, and wherein $C_1$-$C_6$-alkyl, $C_3$-$C_6$-cycloalkyl, $C_3$-$C_6$-heterocycloalkyl are optionally substituted once with —$OR^c$;

$R^{d1}$, $R^{d2}$ independently from each other are selected from the group comprising, preferably consisting of, hydrogen, $C_1$-$C_6$-alkyl, $C_3$-$C_6$-cycloalkyl, or for a —$C(O)R^c$ or —$C(O)NR^{d1}R^{d2}$ group, wherein $C_1$-$C_6$-alkyl, and $C_3$-$C_6$-cycloalkyl are optionally substituted one or more times, in the same way or differently, with an —$OR^c$, or —$C(O)R^b$ group, and wherein $C_1$-$C_6$-alkyl, and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, whereby the carbon backbone of this heterocycloalkyl ring is optionally interrupted one or more times, the same way or differently, by a member of the group comprising, preferably consisting of, NH, $NR^{d1}$, and oxygen;

A is selected from the group comprising, preferably consisting of, —C(O)—, —$C(O)NR^a$—, —$S(O)_2$—;

B is a bond or a group selected from the group comprising, preferably consisting of $C_1$-$C_3$-alkylene, $C_3$-cycloalkylene;

D is para-phenylene;

E is phenylene;

q represents an integer of 0;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

In accordance with a first variant of the more particularly preferred embodiment, supra, the present invention relates to compounds of general formula (I), in which:

$R^1$ represents $—C(O)R^b$ or is selected from the group comprising, preferably consisting of, $C_1$-$C_6$-alkyl, $C_3$-$C_6$-cycloalkyl, $C_3$-$C_6$-heterocycloalkyl, wherein said residues are unsubstituted or substituted one or more times, independently from each other, with $R^6$;

$R^2$ represents a $C_3$-$C_6$-cycloalkyl optionally substituted with $R^7$;

$R^3$ is selected from the group comprising, preferably consisting of, hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen, cyano;

$R^4$ is selected from the group comprising, preferably consisting of, hydrogen, $C_1$-$C_6$-alkyl, $C_1$-$C_6$-haloalkyl, $C_1$-$C_6$-haloalkoxy, hydroxy, amino, halogen, cyano, nitro, $—OR^c$, wherein $C_1$-$C_6$-alkyl is optionally substituted one or more times with $R^8$ $R^5$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, cyano, nitro, $—C(O)R^b$, $—S(O)_2R^b$, $—OR^c$, $—NR^{d1}R^{d2}$, wherein $C_1$-$C_6$-alkyl and $C_3$-$C_6$-heterocycloalkyl are optionally substituted one or more times with $R^8$;

$R^6$ is selected from the group comprising, preferably consisting of, hydrogen, $C_3$-$C_6$-heterocycloalkyl, $C_1$-$C_6$-haloalkoxy, hydroxy, amino, cyano, $—C(O)R^b$, $—S(O)_2R^b$, $—OR^c$, $—NR^{d1}R^{d2}$, wherein $C_3$-$C_6$-heterocycloalkyl is optionally substituted one or more times with $R^8$;

$R^7$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, cyano, $—C(O)R^b$, $—S(O)_2R^b$, $—OR^c$, $—NR^{d1}R^{d2}$, wherein $C_1$-$C_6$-alkyl and $C_3$-$C_6$-heterocycloalkyl are optionally substituted one or more times with $R^8$;

$R^8$ is selected from the group comprising, preferably consisting of, $C_1$-$C_6$-haloalkoxy, hydroxy, amino, cyano, halogen, $—C(O)R^b$, $—S(O)_2R^b$, $—OR^c$, $—NR^{d1}R^{d2}$;

$R^a$ is hydrogen;

$R^b$ is selected from the group comprising, preferably consisting of, $—OR^c$, $—NR^{d1}R^{d2}$, and $C_1$-$C_6$-alkyl;

$R^c$ is selected from the group comprising, preferably consisting of, hydrogen, $C_1$-$C_6$-alkyl, $C_3$-$C_6$-cycloalkyl, $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with $—NR^{d1}R^{d2}$, and wherein $C_1$-$C_6$-alkyl, $C_3$-$C_6$-cycloalkyl, $C_3$-$C_6$-heterocycloalkyl are optionally substituted once with $—OR$;

$R^{d1}$, $R^{d2}$ independently from each other are selected from the group comprising, preferably consisting of, hydrogen, $C_1$-$C_6$-alkyl, $C_3$-$C_6$-cycloalkyl, or for a $—C(O)R^c$ or $—C(O)NR^{d1}R^{d2}$ group, wherein $C_1$-$C_6$-alkyl, and $C_3$-$C_6$-cycloalkyl are optionally substituted one or more times, in the same way or differently, with an $—OR^c$, or $—C(O)R^b$ group, and wherein $C_1$-$C_6$-alkyl, and $C_3$-$C_6$-cycloalkyl are optionally substituted once with an $—NR^{d1}R^{d2}$ group; or, $R^{d1}$ and $R^{d2}$ together with the nitrogen atom to which they are attached, form a 3 to 6 membered heterocycloalkyl ring, whereby the carbon backbone of this heterocycloalkyl ring is optionally interrupted one or more times, the same way or differently, by a member of the group comprising, preferably consisting of, NH, $NR^{d1}$, and oxygen A is $—C(O)NR^a—$;

B is a bond or a group selected from the group comprising, preferably consisting of, $C_1$-$C_3$-alkylene, $C_3$-cycloalkylene;

D is para-phenylene;

E is phenylene;

q represents an integer of 0 wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

Preferably, the first variant of the more particularly preferred embodiment, supra, of the present invention relates to compounds of general formula (I), in which:

$R^1$ represents $—C(O)R^b$ or is selected from the group comprising, preferably consisting of, $C_1$-$C_6$-alkyl, $C_3$-$C_6$-cycloalkyl, $C_3$-$C_6$-heterocycloalkyl, wherein said residues are unsubstituted or substituted one or more times, independently from each other, with $R^6$;

$R^2$ represents cyclopropyl;

$R^3$ is selected from the group comprising, preferably consisting of, hydrogen, methyl, or fluoro;

$R^4$ is selected from the group comprising, preferably consisting of, hydrogen, $C_1$-$C_6$-alkyl, $C_1$-$C_6$-haloalkyl, $C_1$-$C_6$-haloalkoxy, hydroxy, amino, cyano, halogen, $—OR^c$, wherein $C_1$-$C_6$-alkyl is optionally substituted one or more times with $R^8$;

$R^5$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, cyano, halogen, $—C(O)R^b$, $—S(O)_2R^b$, $—OR^c$, $—NR^{d1}R^{d2}$, wherein $C_1$-$C_6$-alkyl and $C_3$-$C_6$-heterocycloalkyl are optionally substituted one or more times with $R^8$;

$R^6$ is selected from the group comprising, preferably consisting of, hydrogen, $C_3$-$C_6$-heterocycloalkyl, $C_1$-$C_6$-haloalkoxy, hydroxy, amino, cyano, $—C(O)R^b$, $—S(O)_2R^b$, $—OR^c$, $—NR^{d1}R^{d2}$, wherein $C_3$-$C_6$-heterocycloalkyl is optionally substituted one or more times with $R^8$;

$R^8$ is selected from the group comprising, preferably consisting of, $C_1$-$C_6$-haloalkoxy, hydroxy, amino, cyano, halogen, $—C(O)R^b$, $—S(O)_2R^b$, $—OR^c$, $—NR^{d1}$, $R^{d2}$;

$R^a$ is hydrogen;

$R^b$ is selected from the group comprising, preferably consisting of, $—OR^c$, and $—NR^{d1}R^{d2}$;

$R^c$ is selected from the group comprising, preferably consisting of, hydrogen, $C_1$-$C_6$-alkyl, $C_3$-$C_6$-cycloalkyl, $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with $—NR^{d1}R^{d2}$, and wherein $C_1$-$C_6$-alkyl, $C_3$-$C_6$-cycloalkyl, $C_3$-$C_6$-heterocycloalkyl are optionally substituted once with —$OR^c$;

$R^{d1}$, $R^{d2}$ independently from each other are selected from the group comprising, preferably consisting of hydrogen, $C_1$-$C_6$-alkyl, $C_3$-$C_6$-cycloalkyl, or for a —$C(O)R^c$ or —$C(O)NR^{d1}R^{d2}$ group, wherein $C_1$-$C_6$-alkyl, and $C_3$-$C_6$-cycloalkyl are optionally substituted one or more times, in the same way or differently, with an —$OR^c$, or —$C(O)R^b$ group, and wherein $C_1$-$C_6$-alkyl, and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, whereby the carbon backbone of this heterocycloalkyl ring is optionally interrupted one or more times, the same way or differently, by a member of the group comprising, preferably consisting of, NH, $NR^{d1}$, and oxygen A is —$C(O)NR^a$—;

B is a bond or a group selected from the group comprising, preferably consisting of $C_1$-$C_3$-alkylene, $C_3$-cycloalkylene;

D is para-phenylene;

E is phenylene;

q represents an integer of 0 wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

More preferably, the first variant of the more particularly preferred embodiment, supra, of the present invention relates to compounds of general formula (I), in which $R^1$ is $C_1$-$C_6$-alkyl;

$R^2$ represents a $C_3$-$C_6$-cycloalkyl optionally substituted with $R^7$;

$R^3$ is selected from the group comprising, preferably consisting of, hydrogen, methyl, or fluoro;

$R^4$ is selected from the group comprising, preferably consisting of, hydrogen, $C_1$-$C_6$-alkyl, $C_1$-$C_6$-haloalkyl, $C_1$-$C_6$-haloalkoxy, hydroxy, amino, cyano, halogen, —$OR^c$, wherein $C_1$-$C_6$-alkyl is optionally substituted one or more times with $R^8$;

$R^5$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, cyano, halogen, —$C(O)R^b$, —$S(O)_2R^b$, —$OR^c$, —$NR^{d1}R^{d2}$, wherein $C_1$-$C_6$-alkyl and $C_3$-$C_6$-heterocycloalkyl are optionally substituted one or more times with $R^8$;

$R^7$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, cyano, —$C(O)R^b$, —$S(O)_2R^b$, —$OR^c$, —$NR^{d1}R^{d2}$, wherein $C_1$-$C_6$-alkyl and $C_3$-$C_6$-heterocycloalkyl are optionally substituted one or more times with $R^8$;

$R^8$ is selected from the group comprising, preferably consisting of, $C_1$-$C_6$-haloalkoxy, hydroxy, amino, cyano, halogen, —$C(O)R^b$, —$S(O)_2R^b$, —$OR^c$, —$NR^{d1}R^{d2}$ $R^a$ is hydrogen $R^b$ is selected from the group comprising, preferably consisting of, —$OR^c$, and —$NR^{d1}R^{d2}$;

$R^c$ is selected from the group comprising, preferably consisting of, hydrogen, $C_1$-$C_6$-alkyl, $C_3$-$C_6$-cycloalkyl, $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with —$NR^{d1}R^{d2}$, and wherein $C_1$-$C_6$-alkyl, $C_3$-$C_6$-cycloalkyl, $C_3$-$C_6$-heterocycloalkyl are optionally substituted once with —$OR^c$;

$R^{d1}$, $R^{d2}$ independently from each other are selected from the group comprising, preferably consisting of hydrogen, $C_1$-$C_6$-alkyl, $C_3$-$C_6$-cycloalkyl, or for a —$C(O)R^c$ or —$C(O)NR^{d1}R^{d2}$ group, wherein $C_1$-$C_6$-alkyl, and $C_3$-$C_6$-cycloalkyl are optionally substituted one or more times, in the same way or differently, with an —$OR^c$, or —$C(O)R^b$ group, and wherein $C_1$-$C_6$-alkyl, and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, whereby the carbon backbone of this heterocycloalkyl ring is optionally interrupted one or more times, the same way or differently, by a member of the group comprising, preferably consisting of, NH, $NR^{d1}$, and oxygen A is —$C(O)NR^a$—;

B is a bond or a group selected from the group comprising, preferably consisting of $C_1$-$C_3$-alkylene, $C_3$-cycloalkylene D is para-phenylene;

E is phenylene;

q represents an integer of 0 wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

Even more preferably, the first variant of the more particularly preferred embodiment, supra, of the present invention relates to compounds of general formula (I), in which:

$R^1$ is $C_1$-$C_3$-alkyl;

$R^2$ is cyclopropyl;

$R^3$ is selected from the group comprising, preferably consisting of, hydrogen, methyl, or fluoro;

$R^4$ is selected from the group comprising, preferably consisting of, hydrogen, halogen, $C_1$-$C_3$-alkyl, or $C_1$-$C_3$-haloalkyl;

$R^5$ is selected from the group comprising, preferably consisting of, hydrogen, $C_1$-$C_3$-alkyl, $C_1$-$C_3$-haloalkyl, $C_1$-$C_3$-haloalkoxy, halogen, —$OR^c$, —$NR^{d1}R^{d2}$, wherein $C_1$-$C_3$-alkyl is optionally substituted by $R^8$;

$R^8$ is selected from the group comprising, preferably consisting of, —$OR^c$, and —$NR^{d1}R^{d2}$ $R^a$ is hydrogen;

$R^c$ is selected from the group comprising, preferably consisting of, hydrogen, and $C_1$-$C_3$-alkyl, wherein $C_1$-$C_3$-alkyl is optionally substituted one or more times with —$NR^{d1}R^{d2}$, and wherein $C_1$-$C_3$-alkyl is optionally substituted once with —$OR^c$;

$R^{d1}$, $R^{d2}$ independently from each other are selected from the group comprising, preferably consisting of hydrogen, $C_1$-$C_3$-alkyl, wherein $C_1$-$C_3$-alkyl is optionally substituted one or more times, in the same way or differently, with an —$OR^c$ group, and wherein $C_1$-$C_3$-alkyl is optionally substituted once with an —$NR^{d1}R^{d2}$ group; or, $R^{d1}$ and $R^{d2}$ together with the nitrogen atom to which they are attached, form a 6 membered heterocycloalkyl ring, whereby the carbon backbone of this heterocycloalkyl ring is optionally interrupted one time, by a member of the group comprising, preferably consisting of, NH, $NR^{d1}$, and oxygen A is —C(O)$NR^a$—

B is a bond;

D is para-phenylene;

E is phenylene;

q represents an integer of 0 wherein, when one or more of $R^a$, $R^b$, $R^c$, $R^{d1}$ or $R^{d2}$ is (are) present in one position in the molecule as well as in one or more further positions in the molecule, said $R^a$, $R^b$, $R^c$, $R^{d1}$ or $R^{d2}$ has (have), independently from each other, the same meanings as defined above in said first position in the molecule and in said second or further positions in the molecule, it being possible for the two or more occurrences of $R^a$, $R^b$, $R^c$, $R^{d1}$ or $R^{d2}$ within a single molecule to be identical or different. For example, when $R^a$ is present twice in the molecule, then the meaning of the first $R^a$ may be H, for example, and the meaning of the second $R^a$ may be methyl, for example.

In accordance with a second variant of the more particularly preferred embodiment, supra, the present invention relates to compounds of general formula (I), in which:

$R^1$ represents —C(O)$R^b$ or is selected from the group comprising, preferably consisting of, $C_1$-$C_6$-alkyl, $C_3$-$C_6$-cycloalkyl, $C_3$-$C_6$-heterocycloalkyl, wherein said residues are unsubstituted or substituted one or more times, independently from each other, with $R^6$;

$R^2$ represents a $C_3$-$C_6$-cycloalkyl optionally substituted with $R^7$;

$R^3$ is selected from the group comprising, preferably consisting of, hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen, cyano;

$R^4$ is selected from the group comprising, preferably consisting of, hydrogen, $C_1$-$C_6$-alkyl, $C_1$-$C_6$-haloalkyl, $C_1$-$C_6$-haloalkoxy, hydroxy, amino, cyano, nitro, halogen, —$OR^c$, wherein $C_1$-$C_6$-alkyl is optionally substituted one or more times with $R^8$;

$R^5$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, cyano, nitro, halogen, —C(O)$R^b$, —S(O)$_2R^b$, —$OR^c$, —$NR^{d1}R^{d2}$, wherein $C_1$-$C_6$-alkyl and $C_3$-$C_6$-heterocycloalkyl are optionally substituted one or more times with $R^8$;

$R^6$ is selected from the group comprising, preferably consisting of, hydrogen, $C_3$-$C_6$-heterocycloalkyl, $C_1$-$C_6$-haloalkoxy, hydroxy, amino, cyano, —C(O)$R^b$, —S(O)$_2R^b$, —$OR^c$, —$NR^{d1}R^{d2}$, wherein $C_3$-$C_6$-heterocycloalkyl is optionally substituted one or more times with $R^8$;

$R^7$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, cyano, —C(O)$R^b$, —S(O)$_2R^b$, —$OR^c$, —$NR^{d1}R^{d2}$, wherein $C_1$-$C_6$-alkyl and $C_3$-$C_6$-heterocycloalkyl are optionally substituted one or more times with $R^8$;

$R^8$ is selected from the group comprising, preferably consisting of, $C_1$-$C_6$-haloalkoxy, hydroxy, amino, cyano, halogen, —C(O)$R^b$, —S(O)$_2R^b$, —$OR^c$, —$NR^{d1}R^{d2}$;

$R^a$ is hydrogen $R^b$ is selected from the group comprising, preferably consisting of, —$OR^c$, —$NR^{d1}R^{d2}$, and $C_1$-$C_6$-alkyl;

$R^c$ is selected from the group comprising, preferably consisting of, hydrogen, $C_1$-$C_6$-alkyl, $C_3$-$C_6$-cycloalkyl, $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with —$NR^{d1}R^{d2}$, and wherein $C_1$-$C_6$-alkyl, $C_3$-$C_6$-cycloalkyl, $C_3$-$C_6$-heterocycloalkyl are optionally substituted once with —$OR^c$;

$R^{d1}$, $R^{d2}$ independently from each other are selected from the group comprising, preferably consisting of hydrogen, $C_1$-$C_6$-alkyl, $C_3$-$C_6$-cycloalkyl, or for a —C(O)$R^c$ or —C(O)$NR^{d1}R^{d2}$ group, wherein $C_1$-$C_6$-alkyl, and $C_3$-$C_6$-cycloalkyl are optionally substituted one or more times, in the same way or differently, with an —$OR^c$, or —C(O)$R^b$ group, and wherein $C_1$-$C_6$-alkyl, and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, whereby the carbon backbone of this heterocycloalkyl ring is optionally interrupted one or more times, the same way or differently, by a member of the group comprising, preferably consisting of, NH, $NR^{d1}$, and oxygen A is —C(O)— or —S(O)$_2$—;

B is a bond or a group selected from the group comprising, preferably consisting of $C_1$-$C_3$-alkylene, $C_3$-cycloalkylene;

D is para-phenylene;

E is phenylene;

q represents an integer of 0 wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

Preferably, the second variant of the more particularly preferred embodiment, supra, of the present invention relates to compounds of general formula (I), in which:

$R^1$ represents —C(O)$R^b$ or is selected from the group comprising, preferably consisting of, $C_1$-$C_6$-alkyl, $C_3$-$C_6$-cycloalkyl, $C_3$-$C_6$-heterocycloalkyl, wherein said residues are unsubstituted or substituted one or more times, independently from each other, with $R^6$;

$R^2$ represents cyclopropyl;

$R^3$ is selected from the group comprising, preferably consisting of, hydrogen, methyl, or fluoro;

$R^4$ is selected from the group comprising, preferably consisting of, hydrogen, $C_1$-$C_6$-alkyl, $C_1$-$C_6$-haloalkyl, $C_1$-$C_6$-haloalkoxy, hydroxy, amino, cyano, halogen, —$OR^c$, wherein $C_1$-$C_6$-alkyl is optionally substituted one or more times with $R^8$;

$R^5$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, cyano, halogen, —C(O)$R^b$, —S(O)$_2R^b$, —$OR^c$, —$NR^{d1}R^{d2}$, wherein $C_1$-$C_6$-alkyl and $C_3$-$C_6$-heterocycloalkyl are optionally substituted one or more times with $R^8$;

$R^6$ is selected from the group comprising, preferably consisting of, hydrogen, $C_3$-$C_6$-heterocycloalkyl, $C_1$-$C_6$-haloalkoxy, hydroxy, amino, cyano, —C(O)$R^b$, —S(O)$_2R^b$, —OR$^c$, —NR$^{d1}$R$^{d2}$, wherein C$_3$-C$_6$-heterocycloalkyl is optionally substituted one or more times with R$^8$;

R$^8$ is selected from the group comprising, preferably consisting of, C$_1$-C$_6$-haloalkoxy, hydroxy, amino, cyano, halogen, —C(O)R$^b$, —S(O)$_2$R$^b$, —OR$^c$, —NR$^{d1}$R$^{d2}$;

R$^a$ is hydrogen

R$^b$ is selected from the group comprising, preferably consisting of, —OR$^c$, and —NR$^{d1}$R$^{d2}$;

R$^c$ is selected from the group comprising, preferably consisting of, hydrogen, C$_1$-C$_6$-alkyl, C$_3$-C$_6$-cycloalkyl, C$_3$-C$_6$-heterocycloalkyl, wherein C$_1$-C$_6$-alkyl, C$_3$-C$_6$-cycloalkyl, C$_3$-C$_6$-heterocycloalkyl are optionally substituted one or more times with —NR$^{d1}$R$^{d2}$, and wherein C$_1$-C$_6$-alkyl, C$_3$-C$_6$-cycloalkyl, C$_3$-C$_6$-heterocycloalkyl are optionally substituted once with —OR$^c$;

R$^{d1}$, R$^{d2}$ independently from each other are selected from the group comprising, preferably consisting of hydrogen, C$_1$-C$_6$-alkyl, C$_3$-C$_6$-cycloalkyl, or for a —C(O)R$^c$ or —C(O)NR$^{d1}$R$^{d2}$ group, wherein C$_1$-C$_6$-alkyl, and C$_3$-C$_6$-cycloalkyl are optionally substituted one or more times, in the same way or differently, with an —OR$^c$, or —C(O)R$^b$ group, and wherein C$_1$-C$_6$-alkyl, and C$_3$-C$_6$-cycloalkyl are optionally substituted once with an —NR$^{d1}$R$^{d2}$ group; or, R$^{d1}$ and R$^{d2}$ together with the nitrogen atom to which they are attached, form a 3 to 6 membered heterocycloalkyl ring, whereby the carbon backbone of this heterocycloalkyl ring is optionally interrupted one or more times, the same way or differently, by a member of the group comprising, preferably consisting of, NH, NR$^{d1}$, and oxygen A is —C(O)— or —S(O)$_2$—;

B is a bond or a group selected from the group comprising, preferably consisting of C$_1$-C$_3$-alkylene, C$_3$-cycloalkylene;

D is para-phenylene

E is phenylene;

q represents an integer of 0;

wherein, when one or more of R$^a$, R$^b$, R$^c$, R$^{d1}$, R$^{d2}$ or R$^8$ is (are) present in one position in the molecule as well as in one or more further positions in the molecule, said R$^a$, R$^b$, R$^c$, R$^{d1}$, R$^{d2}$ or R$^8$ has (have), independently from each other, the same meanings as defined above in said first position in the molecule and in said second or further positions in the molecule, it being possible for the two or more occurrences of R$^a$, R$^b$, R$^c$, R$^{d1}$, R$^{d2}$ or R$^8$ within a single molecule to be identical or different. For example, when R$^a$ is present twice in the molecule, then the meaning of the first R$^a$ may be H, for example, and the meaning of the second R$^a$ may be methyl, for example.

More preferably, the second variant of the more particularly preferred embodiment, supra, of the present invention relates to compounds of general formula (I), in which:

R$^1$ is C$_1$-C$_6$-alkyl;

R$^2$ represents a C$_3$-C$_6$-cycloalkyl optionally substituted with R$^7$;

R$^3$ is selected from the group comprising, preferably consisting of, hydrogen, methyl, or fluoro;

R$^4$ is selected from the group comprising, preferably consisting of, hydrogen, C$_1$-C$_6$-alkyl, C$_1$-C$_6$-haloalkyl, C$_1$-C$_6$-haloalkoxy, hydroxy, amino, cyano, halogen, —OR$^c$, wherein C$_1$-C$_6$-alkyl is optionally substituted one or more times with R$^8$;

R$^5$ is selected from the group comprising, preferably consisting of, hydrogen, C$_1$-C$_6$-alkyl, C$_3$-C$_6$-heterocycloalkyl, C$_1$-C$_6$-haloalkyl, C$_1$-C$_6$-haloalkoxy, hydroxy, amino, cyano, halogen, —C(O)R$^b$, —S(O)$_2$R$^b$, —OR$^c$, —NR$^{d1}$R$^{d2}$, wherein C$_1$-C$_6$-alkyl and C$_3$-C$_6$-heterocycloalkyl are optionally substituted one or more times with R$^8$;

R$^7$ is selected from the group comprising, preferably consisting of, hydrogen, C$_1$-C$_6$-alkyl, C$_3$-C$_6$-heterocycloalkyl, C$_1$-C$_6$-haloalkyl, C$_1$-C$_6$-haloalkoxy, hydroxy, amino, cyano, —C(O)R$^b$, —S(O)$_2$R$^b$, —OR$^c$, —NR$^{d1}$R$^{d2}$, wherein C$_1$-C$_6$-alkyl and C$_3$-C$_6$-heterocycloalkyl are optionally substituted one or more times with R$^8$;

R$^8$ is selected from the group comprising, preferably consisting of, C$_1$-C$_6$-haloalkoxy, hydroxy, amino, cyano, halogen, —C(O)R$^b$, —S(O)$_2$R$^b$, —OR$^c$, —NR$^{d1}$, R$^{d2}$;

R$^a$ is hydrogen

R$^b$ is selected from the group comprising, preferably consisting of, —OR$^c$, and —NR$^{d1}$R$^{d2}$;

R$^c$ is selected from the group comprising, preferably consisting of, hydrogen, C$_1$-C$_6$-alkyl, C$_3$-C$_6$-cycloalkyl, C$_3$-C$_6$-heterocycloalkyl, wherein C$_1$-C$_6$-alkyl, C$_3$-C$_6$-cycloalkyl, C$_3$-C$_6$-heterocycloalkyl are optionally substituted one or more times with —NR$^{d1}$R$^{d2}$, and wherein C$_1$-C$_6$-alkyl, C$_3$-C$_6$-cycloalkyl, C$_3$-C$_6$-heterocycloalkyl are optionally substituted once with —OR$^c$;

R$^{d1}$, R$^{d2}$ independently from each other are selected from the group comprising, preferably consisting of hydrogen, C$_1$-C$_6$-alkyl, C$_3$-C$_6$-cycloalkyl, or for a —C(O)R$^c$ or —C(O)NR$^{d1}$R$^{d2}$ group, wherein C$_1$-C$_6$-alkyl, and C$_3$-C$_6$-cycloalkyl are optionally substituted one or more times, in the same way or differently, with an —OR$^c$, or —C(O)R$^b$ group, and wherein C$_1$-C$_6$-alkyl, and C$_3$-C$_6$-cycloalkyl are optionally substituted once with an —NR$^{d1}$R$^{d2}$ group; or, R$^{d1}$ and R$^{d2}$ together with the nitrogen atom to which they are attached, form a 3 to 6 membered heterocycloalkyl ring, whereby the carbon backbone of this heterocycloalkyl ring is optionally interrupted one or more times, the same way or differently, by a member of the group comprising, preferably consisting of, NH, NR$^{d1}$, and oxygen A is —C(O)— or —S(O)$_2$—;

B is a bond or a group selected from the group comprising, preferably consisting of C$_1$-C$_3$-alkylene, C$_3$-cycloalkylene;

D is para-phenylene

E is phenylene;

q represents an integer of 0 wherein, when one or more of R$^a$, R$^b$, R$^c$, R$^{d1}$, R$^{d2}$ or R$^8$ is (are) present in one position in the molecule as well as in one or more further positions in the molecule, said R$^a$, R$^b$, R$^c$, R$^{d1}$, R$^{d2}$ or R$^8$ has (have), independently from each other, the same meanings as defined above in said first position in the molecule and in said second or further positions in the molecule, it being possible for the two or more occurrences of R$^a$, R$^b$, R$^c$, R$^{d1}$, R$^{d2}$ or R$^8$ within a single molecule to be identical or different. For example, when R$^a$ is present twice in the molecule, then the meaning of the first R$^a$ may be H, for example, and the meaning of the second R$^a$ may be methyl, for example.

Even more preferably, the second variant of the more particularly preferred embodiment, supra, of the present invention relates to compounds of general formula (I), in which:

R$^1$ is C$_1$-C$_3$-alkyl;

R$^2$ is cyclopropyl;

R$^3$ is selected from the group comprising, preferably consisting of, hydrogen, methyl, or fluoro;

R$^4$ is selected from the group comprising, preferably consisting of, hydrogen, halogen, C$_1$-C$_3$-alkyl, or C$_1$-C$_3$-haloalkyl;

$R^5$ is selected from the group comprising, preferably consisting of, hydrogen, $C_1$-$C_3$-alkyl, $C_1$-$C_3$-haloalkyl, $C_1$-$C_3$-haloalkoxy, halogen, —$OR^c$, —$NR^{d1}R^{d2}$, wherein $C_1$-$C_3$-alkyl is optionally substituted by $R^8$;

$R^8$ is selected from the group comprising, preferably consisting of, —$OR^c$, and —$NR^{d1}R^{d2}$;

$R^a$ is hydrogen;

$R^c$ is selected from the group comprising, preferably consisting of, hydrogen, and $C_1$-$C_3$-alkyl, wherein $C_1$-$C_3$-alkyl is optionally substituted one or more times with —$NR^{d1}R^{d2}$, and wherein $C_1$-$C_3$-alkyl is optionally substituted once with —$OR^c$;

$R^{d1}$, $R^{d2}$ independently from each other are selected from the group comprising, preferably consisting of, hydrogen, $C_1$-$C_3$-alkyl, wherein $C_1$-$C_3$-alkyl is optionally substituted one or more times, with an —$OR^c$ group, and wherein $C_1$-$C_3$-alkyl is optionally substituted once with an —$NR^{d1}R^{d2}$ group; $OR^c$;

$R^{d1}$ and $R^{d2}$ together with the nitrogen atom to which they are attached, form a 6 membered heterocycloalkyl ring, whereby the carbon backbone of this heterocycloalkyl ring is optionally interrupted one time, by a member of the group comprising, preferably consisting of, NH, $NR^{d1}$, and oxygen;

A is —C(O)—;

B is $C_1$-alkylene or $C_3$-cycloalkylene D is para-phenylene;

E is phenylene;

q represents an integer of 0 wherein, when one or more of $R^a$, $R^b$, $R^c$, $R^{d1}$ or $R^{d2}$ is (are) present in one position in the molecule as well as in one or more further positions in the molecule, said $R^a$, $R^b$, $R^c$, $R^{d1}$ or $R^{d2}$ has (have), independently from each other, the same meanings as defined above in said first position in the molecule and in said second or further positions in the molecule, it being possible for the two or more occurrences of $R^a$, $R^b$, $R^c$, $R^{d1}$ or $R^{d2}$ within a single molecule to be identical or different. For example, when $R^a$ is present twice in the molecule, then the meaning of the first $R^a$ may be H, for example, and the meaning of the second $R^a$ may be methyl, for example.

DEFINITIONS

The terms as mentioned herein below and in the claims have preferably the following meanings:

The term "alkyl" is to be understood as preferably meaning branched and unbranched alkyl, meaning e.g. methyl, ethyl, n-propyl, iso-propyl, n-butyl, iso-butyl, tert-butyl, sec-butyl, pentyl, iso-pentyl, hexyl, heptyl, octyl, nonyl and decyl and the isomers thereof.

The term "haloalkyl" is to be understood as preferably meaning branched and unbranched alkyl, as defined supra, in which one or more of the hydrogen substituents is replaced in the same way or differently with halogen. Particularly preferably, said haloalkyl is, e.g. chloromethyl, fluoropropyl, fluoromethyl, difluoromethyl, trichloromethyl, 2,2,2-trifluoroethyl, pentafluoroethyl, bromobutyl, trifluoromethyl, iodoethyl, and isomers thereof.

The term "alkoxy" is to be understood as preferably meaning branched and unbranched alkoxy, meaning e.g. methoxy, ethoxy, propyloxy, iso-propyloxy, butyloxy, iso-butyloxy, tert-butyloxy, sec-butyloxy, pentyloxy, iso-pentyloxy, hexyloxy, heptyloxy, octyloxy, nonyloxy, decyloxy, undecyloxy and dodecyloxy and the isomers thereof.

The term "haloalkoxy" is to be understood as preferably meaning branched and unbranched alkoxy, as defined supra, in which one or more of the hydrogen substituents is replaced in the same way or differently with halogen, e.g. chloromethoxy, fluoromethoxy, pentafluoroethoxy, fluoropropyloxy, difluoromethyloxy, trichloromethoxy, 2,2,2-trifluoroethoxy, bromobutyloxy, trifluoromethoxy, iodoethoxy, and isomers thereof.

The term "cycloalkyl" is to be understood as preferably meaning a $C_3$-$C_{10}$ cycloalkyl group, more particularly a saturated cycloalkyl group of the indicated ring size, meaning e.g. a cyclopropyl, cyclobutyl, cyclopentyl, cyclohexyl, cycloheptyl, cyclooctyl, cyclononyl, or cyclodecyl group; and also as meaning an unsaturated cycloalkyl group containing one or more double bonds in the C-backbone, e.g. a $C_3$-$C_{10}$ cycloalkenyl group, such as, for example, a cyclopropenyl, cyclobutenyl, cyclopentenyl, cyclohexenyl, cycloheptenyl, cyclooctenyl, cyclononenyl, or cyclodecenyl group, wherein the linkage of said cyclolalkyl group to the rest of the molecule can be provided to the double or single bond.

The term "heterocycloalkyl" is to be understood as preferably meaning a $C_3$-$C_{10}$ cycloalkyl group, as defined supra, featuring the indicated number of ring atoms, wherein one (or more) ring atom(s) is a (are) heteroatom(s) such as NH, $NR^{d1}$, O, S or is a (are) group(s) such as —C(O)—, —S(O)—, —S(O)$_2$—, or, otherwise stated, in a $C_n$-cycloalkyl group (wherein n is an integer of 3, 4, 5, 6, 7, 8, 9, or 10) one (or more) carbon atom(s) is (are) replaced by said heteroatom(s) or said group(s) to give such a $C_n$ heterocycloalkyl group. Thus, said $C_n$ heterocycloalkyl group refers, for example, to a three-membered heterocycloalkyl, expressed as $C_3$-$C_{10}$ heterocycloalkyl such as oxiranyl. Other examples of heterocycloalkyls are oxetanyl ($C_4$), aziridinyl ($C_3$), azetidinyl ($C_4$), tetrahydrofuranyl ($C_5$), pyrrolidinyl ($C_5$), morpholinyl ($C_6$), dithianyl ($C_6$), thiomorpholinyl ($C_6$), piperidinyl ($C_6$), tetrahydropyranyl ($C_6$), piperazinyl ($C_6$), trithianyl ($C_6$) and chinuclidinyl ($C_8$).

The term "halogen" or "Hal" is to be understood as preferably meaning fluorine, chlorine, bromine, or iodine.

The term "alkeny" is to be understood as preferably meaning branched and unbranched alkenyl, e.g. a vinyl, propen-1-yl, propen-2-yl, but-1-en-1-yl, but-1-en-2-yl, but-2-en-1-yl, but-2-en-2-yl, but-1-en-3-yl, 2-methyl-prop-2-en-1-yl, or 2-methyl-prop-1-en-1-yl group.

The term "alkyny" is to be understood as preferably meaning branched and unbranched alkynyl, e.g. an ethynyl, prop-1-yn-1-yl, but-1-yn-1-yl, but-2-yn-1-yl, or but-3-yn-1-yl group.

As used herein, the term "aryl" is defined in each case as having 3-12 carbon atoms, preferably 6-12 carbon atoms, such as, for example, cyclopropenyl, phenyl, tropyl, indenyl, naphthyl, azulenyl, biphenyl, fluorenyl, anthracenyl etc, phenyl being preferred.

As used herein, the term "heteroaryl" is understood as meaning an aromatic ring system which comprises 3-16 ring atoms, preferably 5 or 6 or 9 or 10 atoms, and which contains at least one heteroatom which may be identical or different, said heteroatom being such as oxygen, nitrogen or sulphur, and can be monocyclic, bicyclic, or tricyclic, and in addition in each case can be benzocondensed. Preferably, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, e.g., benzofuranyl, benzothienyl, benzoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc.

The term "alkylene", as used herein in the context of the compounds of general formula (I) is to be understood as meaning an optionally substituted alkyl chain or "tether", having 1, 2, 3, 4, 5, or 6 carbon atoms, i.e. an optionally substituted —CH$_2$—("methylene" or "single membered tether" or e.g. —C(Me)$_2$-, or —CH(Me)-, ((R)— isomer or (S)-isomer)), —CH$_2$—CH$_2$— ("ethylene", "dimethylene", or "two-membered tether"), —CH$_2$—CH$_2$—CH$_2$— ("propylene", "trimethylene", or "three-membered tether"), —CH$_2$—CH$_2$—CH$_2$—CH$_2$— ("butylene", "tetramethylene", or "four-membered tether"), —CH$_2$—CH$_2$—CH$_2$—CH$_2$—CH$_2$— ("pentylene", "pentamethylene" or "five-membered ether"), or —CH$_2$—CH$_2$—CH$_2$—CH$_2$—CH$_2$—CH$_2$— ("hexylene", "hexamethylene", or six-membered tether") group. Preferably, said alkylene tether is 1, 2, 3, 4, or 5 carbon atoms, more preferably 1 or 2 carbon atoms.

The term "cycloalkylene", as used herein in the context of the compounds of general formula (I) is to be understood as meaning an optionally substituted cycloalkyl ring, having 3, 4, 5, 6, 7, 8, 9 or 10, preferably 3, 4, 5, or 6, carbon atoms, i.e. an optionally substituted cyclopropyl, cyclobutyl, cyclopenyl, cyclohexyl, cycloheptyl, cyclooctyl, cyclononyl, or cyclodecyl ring, preferably a cyclopropyl, cyclobutyl, cyclopentyl or cyclohexyl ring.

The term "heterocycloalkylene", as used herein in the context of the compounds of general formula (I) is to be understood as meaning a cycloalkylene ring, as defined supra, but which contains one (or more) heteroatom(s) such as O, NH; NR$^{d1}$, S or one (or more) group(s) such as —C(O)—, —S(O)—, —S(O)$_2$—.

The term "arylene", as used herein in the context of the compounds of general formula (I) which include the groups D and E, is to be understood as meaning an optionally substituted monocyclic or polycyclic arylene aromatic system e.g. arylene, naphthylene and biarylene, preferably an optionally substituted phenyl ring or "tether", having 6 or 10 carbon atoms. More preferably, said arylene tether is a ring having 6 carbon atoms. If the term "arylene" is used it is to be understood that the linking residues can be arranged to each other in ortho-, para- and meta-position, e.g. an optionally substituted moiety of structure

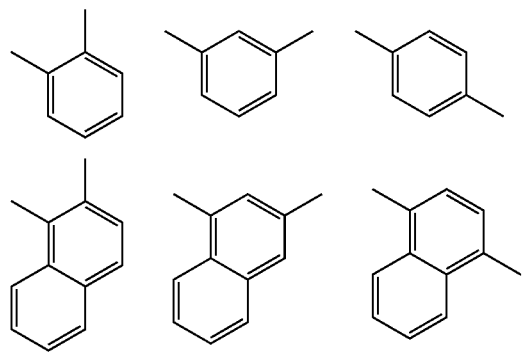

-continued

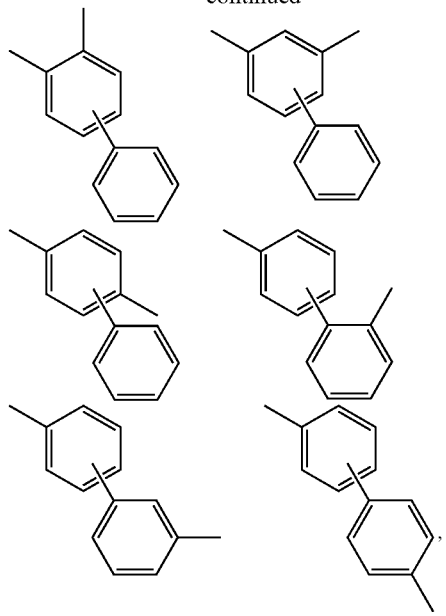

in which linking positions on the rings are shown as non-attached bonds.

The term "heteroarylene", as used herein in the context of the compounds of general formula (I) which include the groups D and E, is to be understood as meaning an optionally substituted monocyclic or polycyclic heteroarylene aromatic system, e.g. heteroarylene, benzoheteroarylene, preferably an optionally substituted 5-membered heterocycle, such as, for example, furan, pyrrole, thiazole, oxazole, isoxazole, or thiophene or "tether", or a 6-membered heterocycle, such as, for example, pyridine, pyrimidine, pyrazine, pyridazine. More preferably, said heteroarylene tether is a ring having 6 carbon atoms, e.g. an optionally substituted structure as shown supra for the arylene moieties, but which contains at least one heteroatom which may be identical or different, said heteroatom being such as oxygen, nitrogen or sulphur. If the term "heteroarylene" is used it is to be understood that the linking residues can be arranged to each other in ortho-, para- and meta-position.

As used herein, the term "$C_1$-$C_6$", as used throughout this text, e.g. in the context of the definition of "$C_1$-$C_6$-alkyl", or "$C_1$-$C_6$-alkoxy", is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$ $C_1$-$C_6$; preferably $C_1$-$C_2$, $C_1$-$C_3$, $C_1$-$C_4$, $C_1$-$C_5$, $C_1$-$C_6$; more preferably $C_1$-$C_4$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; preferably $C_2$-$C_3$.

As used herein, the term "$C_3$-$C_{10}$", as used throughout this text, e.g. in the context of the definitions of "$C_3$-$C_{10}$-cycloalkyl" or "$C_3$-$C_{10}$-heterocycloalkyl", is to be understood as meaning a cycloalkyl group having a finite number of carbon atoms of 3 to 10, i.e. 3, 4, 5, 6, 7, 8, 9 or 10 carbon atoms, preferably 3, 4, 5 or 6 carbon atoms. It is to be understood further that said term "$C_3$-$C_{10}$" is to be interpreted as any sub-range comprised therein, e.g. $C_3$-$C_{10}$, $C_4$-$C_9$, $C_5$-$C_8$, $C_6$-$C_7$; preferably $C_3$-$C_6$.

As used herein, the term "$C_3$-$C_6$", as used throughout this text, e.g. in the context of the definitions of "$C_3$-$C_6$-cycloalkyl" or "$C_3$-$C_6$-heterocycloalkyl", is to be understood as meaning a cycloalkyl group having a finite number of carbon atoms of 3 to 6, i.e. 3, 4, 5, or 6 carbon atoms. It is to be understood further that said term "$C_3$-$C_6$" is to be interpreted as any sub-range comprised therein, e.g. $C_3$-$C_4$, $C_4$-$C_6$, $C_5$-$C_6$.

As used herein, the term "$C_6$-$C_{11}$", as used throughout this text, e.g. in the context of the definitions of "$C_6$-$C_{11}$-aryl", is to be understood as meaning an aryl group having a finite number of carbon atoms of 5 to 11, i.e. 5, 6, 7, 8, 9, 10 or 11 carbon atoms, preferably 5, 6, or 10 carbon atoms. It is to be understood further that said term "$C_6$-$C_{11}$" is to be interpreted as any sub-range comprised therein, e.g. $C_5$-$C_{10}$, $C_6$-$C_9$, $C_7$-$C_8$; preferably $C_5$-$C_6$.

As used herein, the term "$C_5$-$C_{10}$", as used throughout this text, e.g. in the context of the definitions of "$C_5$-$C_{10}$-heteroaryl", is to be understood as meaning a heteroaryl group having a finite number of carbon atoms of 5 to 10, in addition to the one or more heteroatoms present in the ring i.e. 5, 6, 7, 8, 9, or 10 carbon atoms, preferably 5, 6, or 10 carbon atoms. It is to be understood further that said term "$C_5$-$C_{10}$" is to be interpreted as any sub-range comprised therein, e.g. $C_6$-$C_9$, $C_7$-$C_8$, $C_7$-$C_8$; preferably $C_5$-$C_6$.

As used herein, the term "$C_1$-$C_3$", as used throughout this text, e.g. in the context of the definitions of "$C_1$-$C_3$-alkylene", is to be understood as meaning an alkylene group as defined supra having a finite number of carbon atoms of 1 to 3, i.e. 1, 2, or 3. It is to be understood further that said term "$C_1$-$C_3$" is to be interpreted as any sub-range comprised therein, e.g. $C_1$-$C_2$, or $C_2$-$C_3$.

As used herein, the term "one or more times", e.g. in the definition of the substituents of the compounds of the general formulae of the present invention, is understood as meaning "one, two, three, four or five times, particularly one, two, three or four tines, more particularly one, two or three times, more particularly one or two times".

The compounds of the present invention can exist as isomers. The term "isomers" is to be understood as meaning chemical compounds with the same number and types of atoms as another chemical species. There are two main classes of isomers, constitutional isomers and stereoisomers.

The term "constitutional isomers" is to be understood as meaning chemical compounds with the same number and types of atoms, but they are connected in differing sequences. There are functional isomers, structural isomers, tautomers or valence isomers.

In stereoisomers, the atoms are connected sequentially in the same way, such that condensed formulae for two isomeric molecules are identical. The isomers differ, however, in the way the atoms are arranged in space. There are two major sub-classes of stereoisomers; conformational isomers, which interconvert through rotations around single bonds, and configurational isomers, which are not readily interconvertable.

Configurational isomers are, in turn, comprised of enantiomers and diastereomers. Enantiomers are stereoisomers which are related to each other as mirror images. Enantiomers can contain any number of stereogenic centers, as long as each center is the exact mirror image of the corresponding center in the other molecule. If one or more of these centers differs in configuration, the two molecules are no longer mirror images. Stereoisomers which are not enantiomers are called diastereomers. Diastereomers which still have a different constitution, are another sub-class of diastereomers, the best known of which are simple cis-trans isomers.

In order to limit different types of isomers from each other reference is made to IUPAC Rules Section E (*Pure Appl Chem* 45, 11-30, 1976).

The compound according to Fomula (I) can exist in free form or in a salt form. A suitably pharmaceutically acceptable salt of the pyrazolopyridines of the present invention may be, for example, an acid-addition salt of a pyrazolopyridine of the invention which is sufficiently basic, for example, an acid-addition salt with, for example, an inorganic or organic acid, for example hydrochloric, hydrobromic, sulphuric, phosphoric, trifluoroacetic, para-toluenesulphonic, methylsulphonic, citric, tartaric, succinic or maleic acid. In addition, another suitably pharmaceutically acceptable salt of a pyrazolopyridine of the invention which is sufficiently acidic is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, 1,6-hexadiamine, ethanolamine, glucosamine, sarcosine, serinol, tris-hydroxy-methyl-aminomethane, aminopropandiol, sovak-base, 1-amino-2,3,4-butantriol.

The compound according to Formula (I) can exist as N-oxides which are defined in that at least one nitrogen of the compounds of the general Formula (I) may be oxidized.

The compound according to Formula (I) can exist as solvates, in particular as hydrate, wherein the compound according to Formula (I) may contain polar solvents, in particular water, as structural element of the crystal lattice of the compounds. The amount of polar solvents, in particular water, may exist in a stoichiometric or unstoichiometric ratio. In case of stoichiometric solvates, e.g. hydrate, are possible hemi-, (semi-), mono-, sesqui-, di-, tri-, tetra-, penta- etc. solvates or hydrates, respectively.

The compounds of the present invention according to formula (I) can exist as prodrugs, e.g. as in vivo hydrolysable esters. As used herein, the term "in vivo hydrolysable ester" is understood as meaning an in vivo hydrolysable ester of a compound of formula (I) containing a carboxy or hydroxyl group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention. An in vivo hydrolysable ester of a compound of formula (I) containing a hydroxyl group includes inorganic esters such as phosphate esters and [alpha]-acyloxyalkyl ethers and related compounds which as a result of the in vivo hydrolysis of the ester breakdown to give the parent hydroxyl group. Examples of [alpha]-acyloxyalkyl ethers include acetoxymethoxy and 2,2-dimethylpropionyloxymethoxy. A selection of in vivo hydrolysable ester forming groups for hydroxyl include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

The compounds of the present invention according to Formula (I), or salts, N-oxides, or prodrugs thereof, may contain one or more asymmetric centers. Asymmetric carbon atoms may be present in the (R) or (S) configuration or (R,S) configuration. Substituents on a ring may also be present in either cis or trans form. It is intended that all such configurations (including enantiomers and diastereomers), are included within the scope of the present invention. Preferred stereoisomers are those with the configuration which produces the more desirable biological activity. Separated, pure or partially purified configurational isomers or racemic mixtures of the compounds of this invention are also included within the scope of the present invention. The purification of said isomers and the separation of said isomeric mixtures can be accomplished by standard techniques known in the art.

Further another embodiment of the present invention relates to the use of a compound of general formula (6) as mentioned below for the preparation of a compound of general formula (I) as defined supra.

Further another embodiment of the present invention relates to the use of a compound of general formula (10) as mentioned below for the preparation of a compound of general formula (I) as defined supra.

Further another embodiment of the present invention relates to the use of a compound of general formula (11) as mentioned below for the preparation of a compound of general formula (I) as defined supra.

The compounds of the present invention can be used in treating diseases of dysregulated vascular growth or diseases which are accompanied with dysregulated vascular growth. Especially, the compounds effectively interfere with Tie2 signalling. In addition, the compounds of the present invention allow for tunability of the inhibition of an additional kinase target according to the appropriate therapeutic needs.

Therefore, another aspect of the present invention is a use of the compound of general formula (I) described supra for manufacturing a pharmaceutical composition for the treatment of diseases of dysregulated vascular growth or of diseases which are accompanied with dysregulated vascular growth.

Preferably, the use is in the treatment of diseases, wherein the diseases are tumours and/or metastases thereof.

Another preferred use is in the treatment of diseases, wherein the diseases are retinopathy, other angiogenesis dependent diseases of the eye, in particular cornea transplant rejection or age-related macular degeneration, rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and diseases of the bowel.

A further use is in the treatment of diseases, wherein the diseases are coronary and peripheral artery disease.

Another use is in the treatment of diseases, wherein the diseases are ascites, oedema such as brain tumour associated oedema, high altitude trauma, hypoxia induced cerebral oedema, pulmonary oedema and macular oedema or oedema following burns and trauma, chronic lung disease, adult respiratory distress syndrome, bone resorption and for benign proliferating diseases such as myoma, benign prostate hyperplasia and wound healing for the reduction of scar formation, reduction of scar formation during regeneration of damaged nerves, endometriosis, pre-eclampsia, postmenopausal bleeding and ovarian hyperstimulation.

Yet another aspect of the invention is a method of treating a disease of dysregulated vascular growth or diseases which are accompanied with dysregulated vascular growth, by administering an effective amount of a compound of general formula (I) described supra.

Preferably, the diseases of said method are tumours and/or metastases thereof.

Also, the diseases of said method are retinopathy, other angiogenesis dependent diseases of the eye, in particular cornea transplant rejection or age-related macular degeneration, e.g. rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and diseases of the bowel.

Further, the disease of the method are coronary and peripheral artery disease.

Other diseases of the method are ascites, oedema such as brain tumour associated oedema, high altitude trauma, hypoxia induced cerebral oedema, pulmonary oedema and macular oedema or oedema following burns and trauma, chronic lung disease, adult respiratory distress syndrome, bone resorption and for benign proliferating diseases such as myoma, benign prostate hyperplasia and wound healing for the reduction of scar formation, reduction of scar formation during regeneration of damaged nerves, endometriosis, pre-eclampsia, postmenopausal bleeding and ovarian hyperstimulation.

The compounds of the present invention can thus be applied for the treatment of diseases accompanied by neoangiogenesis. This holds principally for all solid tumours, e.g. breast, colon, renal, lung and/or brain tumours or metastases thereof and can be extended to a broad range of diseases, where pathologic angiogenesis is persistent. This applies for diseases with inflammatory association, diseases associated with oedema of various forms and diseases associated with stromal proliferation and pathologic stromal reactions broadly. Particularly suited is the treatment for gynaecological diseases where inhibition of angiogenic, inflammatory and stromal processes with pathologic character can be inhibited. The treatment is therefore an addition to the existing armament to treat diseases associated with neoangiogenesis.

The compounds of the present invention can be used in particular in therapy and prevention of tumour growth and metastases, especially in solid tumours of all indications and stages with or without pre-treatment if the tumour growth is accompanied with persistent angiogenesis. However, it is not restricted to tumour therapy but is also of great value for the treatment of other diseases with dysregulated vascular growth. This includes retinopathy and other angiogenesis dependent diseases of the eye (e.g. cornea transplant rejection, age-related macular degeneration), rheumatoid arthritis, and other inflammatory diseases associated with angiogenesis such as psoriasis, delayed type hypersensitivity, contact dermatitis, asthma, multiple sclerosis, restenosis, pulmonary hypertension, stroke and inflammatory diseases of the bowel, such as Crohn's disease. It includes coronary and peripheral artery disease. It can be applied for disease states such as ascites, oedema, such as brain tumour associated oedema, high altitude trauma, hypoxia induced cerebral oedema, pulmonary oedema and macular oedema or oedema following burns and trauma. Furthermore, it is useful for chronic lung disease, adult respiratory distress syndrome. Also for bone resorption and for benign proliferating diseases such as myoma, benign prostate hyperplasia and wound healing for the reduction of scar formation. It is therapeutically valuable for the treatment of diseases, where deposition of fibrin or extracellular matrix is an issue and stroma proliferation is accelerated (e.g. fibrosis, cirrhosis, carpal tunnel syndrome etc). In addition it can be used for the reduction of scar formation during regeneration of damaged nerves, permitting the reconnection of axons. Further uses are endometriosis, pre-eclampsia, postmenopausal bleeding and ovarian hyperstimulation.

Another aspect of the present invention is a pharmaceutical composition which contains a compound of formula (I) or a pharmaceutically acceptable salt thereof, or an N-oxide thereof, or a prodrug thereof, in admixture with one or more suitable excipients. This composition is particularly suited for the treatment of diseases of dysregulated vascular growth or of diseases which are accompanied with dysregulated vascular growth as explained above.

In order to use the compounds of the present invention as pharmaceutical products, the compounds or mixtures thereof may be provided in a pharmaceutical composition, which, as well as the compounds of the present invention for enteral, oral or parenteral application contain suitable pharmaceutically acceptable organic or inorganic inert base material, e.g. purified water, gelatine, gum Arabic, lactate, starch, magnesium stearate, talcum, vegetable oils, polyalkyleneglycol, etc.

The pharmaceutical compositions of the present invention may be provided in a solid form, e.g. as tablets, dragées, suppositories, capsules or in liquid form, e.g. as a solution, suspension or emulsion. The pharmaceutical composition may additionally contain auxiliary substances, e.g. preservatives, stabilisers, wetting agents or emulsifiers, salts for adjusting the osmotic pressure or buffers.

For parenteral applications, (including intravenous, subcutaneous, intramuscular, intravascular or infusion), sterile injection solutions or suspensions are preferred, especially aqueous solutions of the compounds in polyhydroxyethoxy containing castor oil.

The pharmaceutical compositions of the present invention may further contain surface active agents, e.g. salts of gallenic acid, phospholipids of animal or vegetable origin, mixtures thereof and liposomes and parts thereof.

For oral application tablets, dragées or capsules with talcum and/or hydrocarbon-containing carriers and binders, e.g. lactose, maize and potato starch, are preferred. Further application in liquid form is possible, for example as juice, which contains sweetener if necessary.

The dosage will necessarily be varied depending upon the route of administration, age, weight of the patient, the kind and severity of the illness being treated and similar factors. The daily dose is in the range of 0.5 to 1,500 mg. A dose can be administered as unit dose or in part thereof and distributed over the day. Accordingly the optimum dosage may be determined by the practitioner who is treating any particular patient.

It is possible for compounds of general formula (I) of the present invention to be used alone or, indeed in combination with one or more further drugs, particularly anti-cancer drugs or compositions thereof. Particularly, it is possible for said combination to be a single pharmaceutical composition entity, e.g. a single pharmaceutical formulation containing one or more compounds according to general formula (I) together with one or more further drugs, particularly anti-cancer drugs, or in a form, e.g. a "kit of parts", which comprises, for example, a first distinct part which contains one or more compounds according to general formula I, and one or more further distinct parts each containing one or more further drugs, particularly anti-cancer drugs. More particularly, said first distinct part may be used concomitantly with said one or more further distinct parts, or sequentially.

Another aspect of the present invention is a method which may be used for preparing the compounds according to the present invention.

EXPERIMENTAL DETAILS AND GENERAL PROCESSES

The following Table lists the abbreviations used in this paragraph and in the Examples section as far as they are not explained within the text body. NMR peak forms are stated as they appear in the spectra, possible higher order effects have not been considered.

Chemical names were generated using AutoNom2000 as implemented in MDL ISIS Draw.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallisation. In some cases, impurities may be stirred out using a suitable solvent. In some cases, the compounds may be purified by chromatography, particularly flash column chromatography, using for example prepacked silica gel cartridges, e.g. from Separtis such as Isolute® Flash silica gel or Isolute® Flash NH$_2$ silica gel in combination with a Flashmaster 11 autopurifier (Argonaut/Biotage) and eluents such as gradients of hexane/EtOAc or DCM/ethanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid or aqueous ammonia.

| Abbreviation | Meaning |
| --- | --- |
| Ac | Acetyl |
| Boc | tert-butyloxycarbonyl |
| Br | Broad |
| c- | cyclo- |
| CI | chemical ionisation |
| D | Doublet |
| Dd | doublet of doublet |
| DCM | Dichloromethane |
| DIPEA | N,N-diisopropylethyl amine |
| DMAP | N,N-dimethylaminopyridine |
| DMF | N,N-dimethylformamide |
| DMSO | dimethyl sulphoxide |
| eq. | Equivalent |
| ESI | electrospray ionisation |
| GP | general procedure |
| HPLC | high performance liquid chromatography |
| LC-MS | liquid chromatography mass spectrometry |
| M | Multiplet |
| Mc | centred multiplet |
| MS | mass spectrometry |
| NMR | nuclear magnetic resonance spectroscopy: chemical shifts (□) are given in ppm. |
| OTf | trifluoromethylsulphonyl- |
| 1-PrOH | 1-propanol |
| Pg | protecting group |
| Q | Quartet |
| Rf | at reflux |
| r.t. or rt | room temperature |
| S | Singlet |

| Abbreviation | Meaning |
| --- | --- |
| sept. | Septet |
| T | Triplet |
| T3P | 1-propanephosphonic acid cyclic anhydride = 2,4,6-tripropyl-[1,3,5,2,4,6]trioxatriphosphinane 2,4,6-trioxide |
| TEA | Triethylamine |
| TFA | trifluoroacetic acid |
| THF | Tetrahydrofuran |

The following Schemes and general procedures illustrate general synthetic routes to the compounds of general formula I of the invention and are not intended to be limiting. Specific examples are described in the subsequent paragraph.

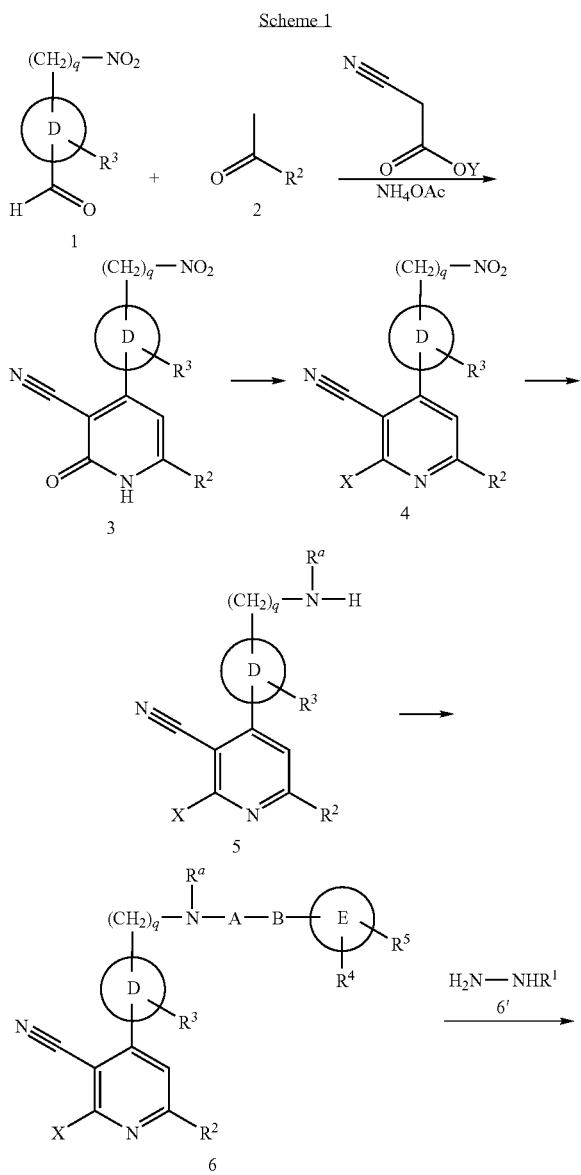

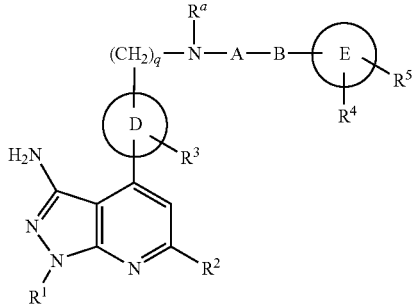

Scheme 1 General procedure for the preparation of compounds of the general formula (I), wherein X represents OTf, Cl, F, OAc, OMe, Y represents Me, Et and A, B, D, E, $R^a$, $R^1$, $R^2$, $R^3$, $R^4$, $R^5$ and q are as defined in the description and claims of this invention.

Compounds of general formula (I) can be synthesized according to the procedure depicted in Scheme 1. Pyridones of general formula 3 are accessible for example by a multi-component coupling of a (hetero)aryl carbaldehyde 1, a methylketone 2, an alkyl cyanoacetate (e.g. methyl cyanoacetate or ethyl cyanoacetate), for example, and an ammonium salt, preferably ammonium acetate, in a suitable solvent, preferably ethanol, preferably with heating at temperatures preferably up to the boiling point of the solvent, whereby in the case of ethanol 80° C. is preferred.

The so-formed pyridones 3 are converted into pyridines of general formula 4 carrying a leaving group X at the C2 position, wherein X represents a leaving group, such as, for example, trifluoromethanesulphonyl (OTf), acetate (OAc), methoxy (OMe), Cl, or F, it being understood that the above-mentioned list of leaving groups is not limiting. Preferably, X represents Cl, even more preferably X represents OTf. Conversion of intermediate compounds of general formula 3 into intermediates of general formula 4 may be achieved by a variety of methods which are well-known to the person skilled in the art, e.g. when X=Cl, by reaction with phosphorus oxychloride, optionally in the presence of a solvent, e.g. DMF; or, for example, when X=OTf, by reaction with trifluoromethanesulphonic acid anhydride, in the presence of a suitable base, e.g. pyridine, which may also be used as solvent, optionally in the presence of an inert solvent, e.g. dichloromethane, preferably at temperatures ranging from −20° C. to room temperature, whereby 0° C. up to room temperature is preferred.

Reduction of the nitro group in intermediate compounds of general formula 4 gives rise to intermediate amine compounds of general formula 5. The person skilled in the art is well aware of many methods for nitro group reduction, the reduction of intermediate compounds of general formula 4 with a reducing agent, such as, for example, tin (II) chloride dihydrate, in a suitable solvent, e.g. ethanol, preferably with heating at temperatures ranging from room temperature to the boiling point of the solvents, whereby in the case of ethanol 80° C., being preferred.

Intermediate compounds of general formula 6 are formed from intermediate compounds of general formula 5 by reaction with, for example, a suitably functionalized isocyanate (leading to ureas), a suitably functionalized sulphonyl chloride (leading to sulphonylamides), or a suitably functionalized acid halide, particularly an acid chloride (leading to carboxylic amides), in the presence of a suitable base as necessary, e.g. pyridine, which may also be used as solvent, optionally in the presence of an inert solvent, e.g. dichloromethane, acetonitrile, DMF or THF, at temperatures preferably ranging from −20° C. to the boiling point of the solvent, room temperature being preferred.

Reaction of intermediate compounds of general formula 6 with, for example, a substituted hydrazine 6', preferably in a suitable solvent, e.g. 1-propanol, ("1-PrOH") preferably with heating at temperatures from room temperature up to the boiling point of the solvent, whereby in the case of 1-PrOH 100° C. is preferred, leads to compounds of general formula I.

A variety of substituted hydrazine building blocks is commercially available, either in form of their free base or as various types of salts (e.g. hydrochlorides, oxalates), which can be converted into their respective free bases by alkaline treatment either before the cyclization or in situ. Additionally, substituted alkyl-, allyl-, and benzylhydrazines (or their respective hydrochloride salts) are accessible from the respective alkyl-, allyl- and benzylhalides, preferably the respective alkyl-, allyl- and benzyl bromides, by nucleophilic substitution reaction with a protected hydrazine, such as Boc-NHNH$_2$, in an inert solvent, preferably MeOH, in the presence of an amine promoter, e.g. Et$_3$N, preferably with heating at temperatures ranging from room temperature up to the boiling point of the solvent, followed by Boc-deprotection employing conditions known to the person skilled in the art, preferably by treatment with HCl in a mixture of diethyl ether and methanol (for a representative procedure, see *J. Med. Chem.* 2006, 49, 2170).

The substituents $R^a$, $R^1$, $R^2$, $R^3$, $R^4$, $R^5$ may be further modified in each step (general formula 1 to general formula 13) or in the last step (general formula I). These modifications can be such as the introduction of protecting groups, cleavage of protecting groups, reduction or oxidation of functional groups, substitution or other reactions. Appropriate protecting groups and their introduction and cleavage are well-known to the person skilled in the art, (see for example T. W. Greene and P. G. M. Wuts in *Protective Groups in Organic Synthesis*, 3$^{rd}$ edition, Wiley 1999).

The person skilled in the art is well aware of alternative methods of forming ureas, which may be of special importance in cases were the respective isocyanates are not readily available.

Scheme 2

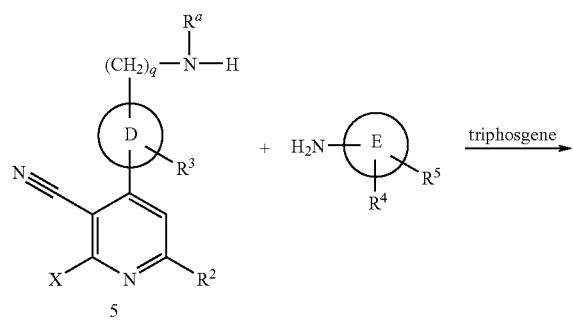

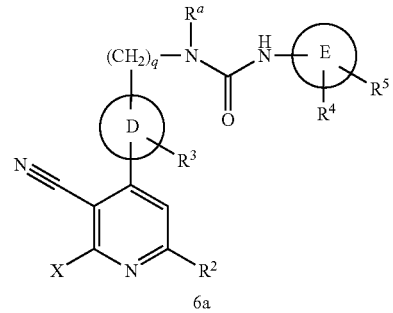

Scheme 2 Urea formation by in situ activation of one of two amines with triphosgene and subsequent reaction with the second amine, wherein X, represents OTf, Cl, F, OAc, OMe, and A, B, D, E, $R^a$, $R^1$, $R^2$, $R^3$, $R^4$, $R^5$ and q are as defined in the description and claims of this invention.

An alternative process of generating ureas of general formula 6a is depicted in Scheme 2. In this case, urea formation starting from amines of general formula 5 may be achieved by coupling with a second functionalized amine via in situ conversion of one of the reacting amines into the respective carbamoyl chloride, aryl- or alkenylcarbamate (see for example *J. Org. Chem.* 2005, 70, 6960 and references cited therein). This process may provide an alternative to the formation and isolation of the respective isocyanate derived from one of the starting amines (see for example *Tetrahedron Lett.* 2004, 45, 4769). More particularly, ureas of formula 6a may be formed from two suitably functionalized amines and a suitable phosgene equivalent, preferably triphosgene, preferably in an inert solvent, preferably acetonitrile, at temperatures preferably ranging from −20° C. to room temperature, room temperature being preferred.

Processes for the preparation of functionalized (hetero)aryl amines are well-known to the person skilled in the art. Starting from commercially available (hetero)aryl amines or nitro (hetero)arylenes, well known conversions, including, but not limited to, alkylations, nucleophilic or electrophilic substitutions, acylations, halogenations, nitrations, sulphonylations, (transition) metal catalyzed couplings, metallations, rearrangements, reductions, and/or oxidations may be applied to prepare functionalized amines to be used in the urea formation step. In addition to specific procedures given in the following experimental section, detailed procedures may be found in the scientific and patent literature (see for example WO2005051366, WO2005110410, WO2005113494, WO2006044823), which are herein incorporated in their entirety by reference.

In the case of the conversion of amines of general formula 5 into amides, it is also possible to react amines of general formula 5 with an appropriate ester according to a method described in *J. Org. Chem.* 1995, 60, 8414 in the presence of trimethylaluminium and in suitable solvents such as toluene, preferably at temperatures of 0° C. to the boiling point of the solvent. For amide formation, however, all processes that are known from peptide chemistry to the person skilled in the art are also available. For example, the corresponding acid, which may be obtained from the corresponding ester by saponification, can be reacted with amines of general formula 5 in aprotic polar solvents, such as, for example, DMF, via an activated acid derivative, which is obtainable, for example, with hydroxybenzotriazole and a carbodiimide, such as, for example, diisopropylcarbodiimide (DIC), at temperatures of between 0° C. and the boiling point of the solvent, preferably at 80° C., or else with preformed reagents, such as, for example, O-(7-azabenzotriazol-1-yl)-1,1,3,3-tetramethyluronium hexafluorophosphate (HATU) (see for example *Chem. Comm.* 1994, 201), at temperatures of between 0° C. and the boiling point of the solvent, preferably at room temperature, or else with activating agents such as dicyclohexylcarbodiimide (DCC)/dimethylaminopyridine (DMAP) or N-ethyl-N'-dimethylaminopropyl-carbodiimide (EDCI)/dimethylaminopyridine (DMAP) or T3P. The addition of a suitable base such as N-methylmorpholine, for example, may be necessary. Amide formation may also be accomplished via the acid halide, mixed acid anhydride, imidazolide or azide.

The carboxylic acids required for the above described amide coupling reactions are either commercially available or are accessible from commercially available carboxylic esters or nitriles. Alternatively, (hetero)aryls bearing a methylenenitrile substituent are easily accessible from the respective halides via a nucleophilic substitution reaction (e.g. KCN, cat. KI, EtOH/$H_2O$). Incorporation of additional functionality into commercially available starting materials can be accomplished by a multitude of aromatic transformation reactions known to the person skilled in the art, including, but not limited to, electrophilic halogenations, electrophilic nitrations, Friedel-Crafts acylations, nucleophilic displacement of fluorine by oxygen nucleophiles and transformation of (hetero)aryl carboxylic acids into amides and subsequent reduction into benzylic amines, whereby the latter two methods are of particular relevance for the introduction of ether and/or aminomethylene side chains.

Benzylic nitriles and esters (and heteroaryl analogs thereof) can be efficiently alkylated at the benzylic position under basic conditions and subsequently hydrolyzed to the corresponding alkylated acids. Conditions for α-alkylations of nitriles and esters include, but are not limited to, the use of alkyl bromides or alkyl iodides as electrophiles under basic conditions in the presence or absence of a phase-transfer catalyst in a mono- or biphasic solvent system. Particularly, by using excess alkyl iodides as electrophilic species ☐,☐-dialkylated nitriles are accessible. More particularly, by using 1,ω-dihaloalkyls as electrophiles cycloalkyl moieties can be installed at the benzylic position of nitriles and esters (*J. Med. Chem.* 1975, 18, 144; WO2003022852). Even more particularly, by using a 1,2-dihaloethane, such as, for example, 1,2-dibromoethane or 1-bromo-2-chloroethane, a cyclopropane ring can be installed at the benzylic position of a nitrite or ester. The hydrolysis of nitriles to yield carboxylic acids can be accomplished, as known to the person skilled in the art, under acid or base-mediated conditions.

Scheme 3

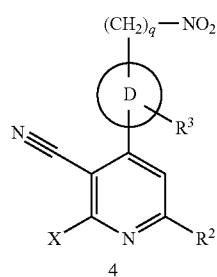

4

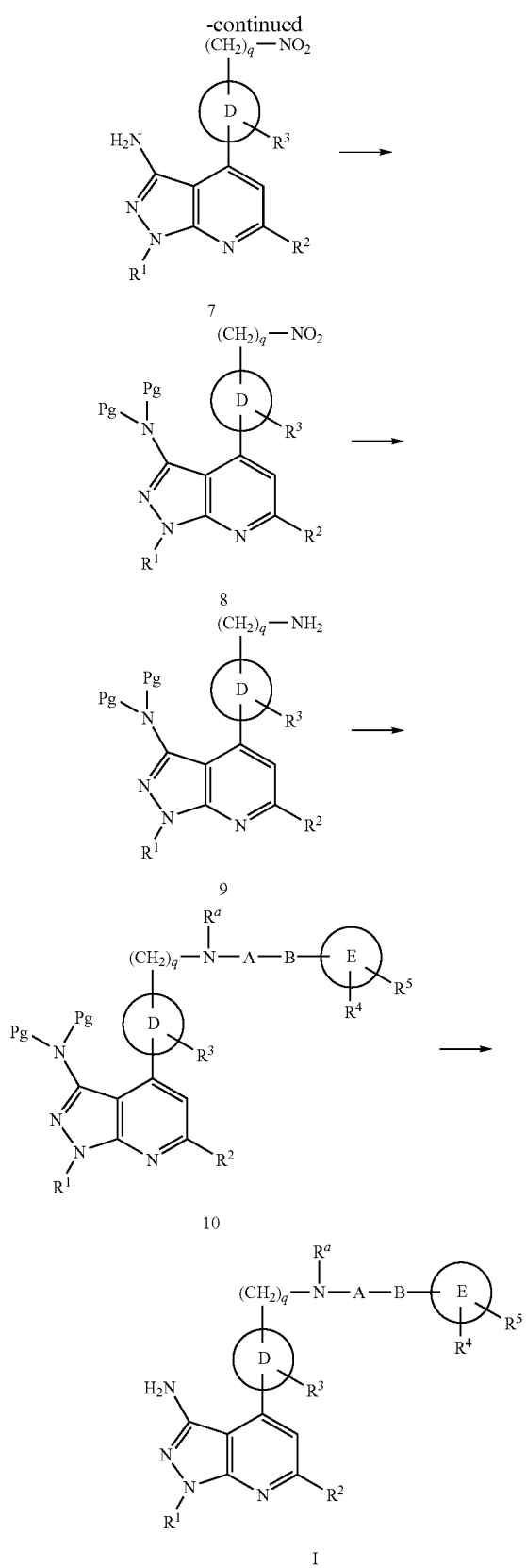

I

Scheme 3 Alternative general procedure for the preparation of compounds of the general formula (I), wherein X represents OTf, Cl, F, OAc, OMe, and A, B, D, E, $R^a$, $R^1$, $R^2$, $R^3$, $R^4$, $R^5$ and q are as defined in the description and claims of this invention. The 3-amino group on the pyrazolo ring of compounds of the general formula 8, 9, and 10 may be substituted with one or two protecting groups Pg, preferably one or two Boc groups or even more preferably said amino group may be protected in form of a phthalimide.

An alternative synthetic route to compounds of general formula (I) is depicted in Scheme 3. Pyridines of the general formula 4, which can be prepared as described above, can be converted into the respective pyrazolopyridines of general formula 7 by cyclization with substituted hydrazines in a suitable solvent, e.g. 1-propanol, at temperatures from room temperature up to the boiling point of the solvent, whereby in the case of 1-PrOH 100° C. is preferred.

Protection of the 3-amino group of the pyrazole nucleus leads to compounds of the general formula 8. Suitable protecting groups for amino functions are well known to the person skilled in the art (see for example T. W. Greene and P. G. M. Wuts in *Protective Groups in Organic Synthesis*, 3rd edition, Wiley 1999). Preferably, the 3-amino group is protected by formation of the respective phthalimide. In particular, phthalimido protection of 3-aminopyrazoles can be achieved by reaction of the amine with phthalic anhydride in a suitable inert solvent, e.g. acetonitrile or dioxane, optionally in the presence of a basic mediator, e.g. $Et_3N$, DIPEA or DMAP, at temperatures from room temperature up to the boiling point of the respective solvent.

Nitro reduction yielding compounds of the general formula 9 and e.g. urea, sulphonamide, or amide formation to give compounds of general formula 10 are feasible as described above. Finally, the compounds of the present invention (I) are accessible by deprotection of the amino group in compounds of the general formula 10. Preferably, cleavage of the phthalimido group can be achieved, as known to the person skilled in the art, by reaction with hydrazine or hydrazine hydrate in solvents such as EtOH at temperatures from room temperature up to the boiling point of the respective solvent.

Scheme 4

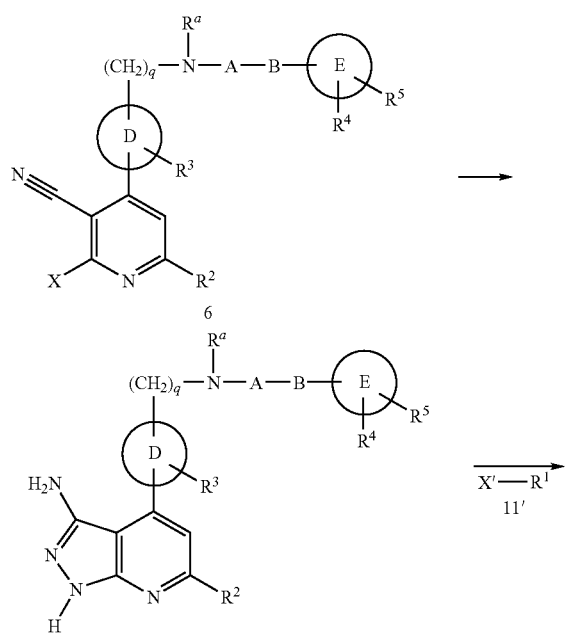

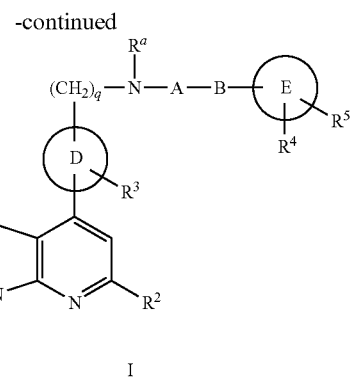

Scheme 4 Additional general procedure for the preparation of compounds of the general formula (I) employing a late-stage N1-functionalization, wherein X represents OTf, Cl, F, OAc, OMe, and X' represents OTf, Cl, Br, I, OMs (methanesulfonyl), OAc, and A, B, D, E, $R^a$, $R^1$, $R^2$, $R^3$, $R^4$, $R^5$ and q are as defined in the description and claims of this invention.

As a further optional process leading to compounds of the present invention, introduction of $R^1$-substituents as present in compounds of the present invention of general formula I can be accomplished after formation of 1H-pyrazolopyridines 11 by alkylation or acylation and subsequent reduction (Scheme 4). This process is of particular importance if appropriately substituted hydrazines are not readily available. 1H-Pyrazolopyridines of general formula II are accessible from synthetic intermediates of formula 6 (which can be prepared as described above) by cyclization with hydrazine or more preferably with hydrazine hydrate in a suitable solvent, preferably 1-propanol, at temperatures from room temperature up to the boiling point of the solvent, whereby in the case of 1-PrOH 100° C. is preferred. Introduction of $R^1$-groups to yield compounds of the present invention of general formula I can be achieved employing various conditions for introducing substituents to nitrogen atoms as known to the person skilled in the art. These conditions include, but are not limited to, alkylations under basic conditions employing alkyl-, allyl-, benzylhalides or □-halocarbonyl compounds as electrophiles (e.g. WO2005056532; *Chem. Pharm. Bull.* 1987, 35, 2292; *J. Med. Chem.* 2005, 48, 6843), alkylations under reductive conditions employing aldehydes as electrophiles and an appropriate reducing agent (e.g. $BH_3$.pyr, NaBH (OAc)$_3$, $NaBH_3CN$, $NaBH_4$), Mitsunobu-type alkylations employing primary or secondary alcohols as electrophiles (e.g. *Tetrahedron* 2006, 62, 1295; *Bioorg. Med. Chem. Lett.* 2002, 12, 1687), or N-acylations (see for example *J. Med. Chem.* 2005, 48, 6843) optionally followed by amide reduction. The presence of the 3-amino group may give rise to regioisomeric product mixtures under some of these conditions requiring separation of regioisomeric products by methods known to the person skilled in the art. Intermittent protection of the 3-amino group (e.g. by formation of a phthalimido group, under conditions as described above, followed by Ni substitution and protecting group cleavage may instead allow regioselective introduction of substituents at N1 (see for example US20040235892). Conditions for N1-alkylation of 3-aminopyrazoles of the general formula II include, but are not limited to, treatment with an excess of the respective electrophile (e.g. alkyl-, allyl-, benzylhalides or □-halocarbonyl compounds) in the presence of a base, e.g. potassium carbonate or cesium carbonate, in DMF at temperatures from room temperature up to the boiling point of the solvent.

Even more preferably, 1H-pyrazoles of general formula 11 are deprotonated with sodium hydride in DMF at temperatures from 0° C. up to 80° C. followed by reaction with the respective electrophile (e.g. alkyl-, allyl-, benzylhalides or □-halocarbonyl compounds) in DMF at temperatures from room temperature up to the boiling point of the solvent.

Scheme 5

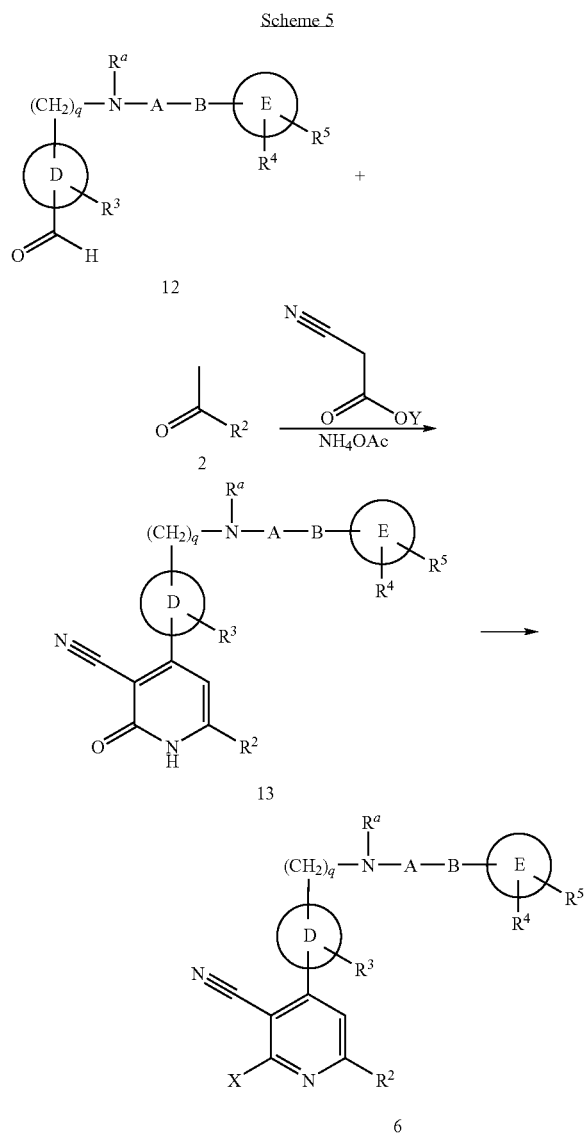

Scheme 6

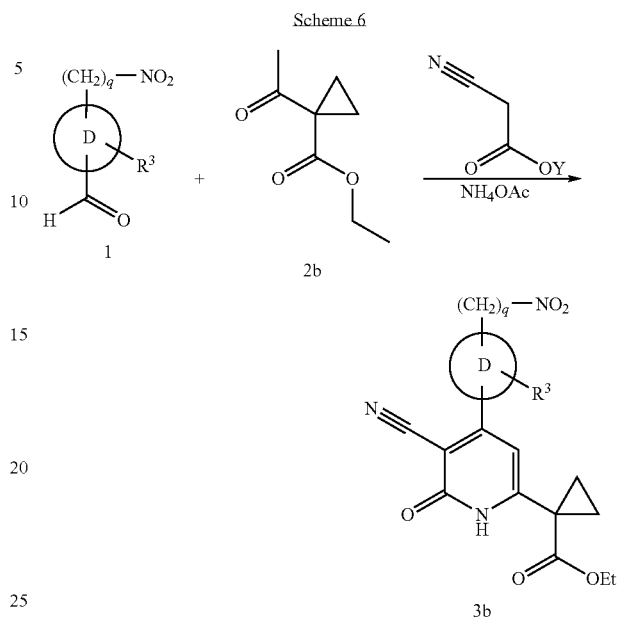

Scheme 6 Synthesis of pyridones of formula 3b, wherein Y represents Me, Et and D, $R^3$, and q are as defined in the description and claims of this invention.

Scheme 6 depicts the more specific synthesis of pyridones of formula 3b, which in turn may be used as substrates in those conversions described above, especially those in Scheme 1 and subsequent Schemes. In addition, methyl ketone 2b may be used in the conversion shown in Scheme 5 replacing substrate 2. Methyl ketone 2b is accessible from the corresponding □-ketoester by cyclopropanation by various conditions known to the person skilled in the art, for example as described in US20030065212 and U.S. Pat. No. 5,286,723. Optionally, the ethyl ester functionality in substrate 2b, in pyridone 3b and subsequent products may be further modified. These modifications may include, but are not limited to, transesterifications, saponifications, amide formations, reductions and subsequent aminations or etherifications or Curtius rearrangements and subsequent amine functionalizations known to the person skilled in the art.

Scheme 5 Alternative order of conversions for the preparation of compounds of the general formula (I), wherein X, represents OTf, Cl, F, OAc, OMe, Y represents Me, Et and A, B, D, E, $R^a$, $R^1$, $R^2$, $R^3$, $R^4$, $R^5$ and q are as defined in the description and claims of this invention.

Alternatively to the process shown in Scheme 1, the order of conversions may be changed as exemplified in Scheme 5. A fully functionalized northern part of compounds of the present invention may already be present in aldehydes of general formula 12, which lead upon multicomponent coupling as described above to pyridones of general formula 13. Conversion of pyridones of general formula 13 into pyridines of general formula 6 can be accomplished as described above.

Scheme 7

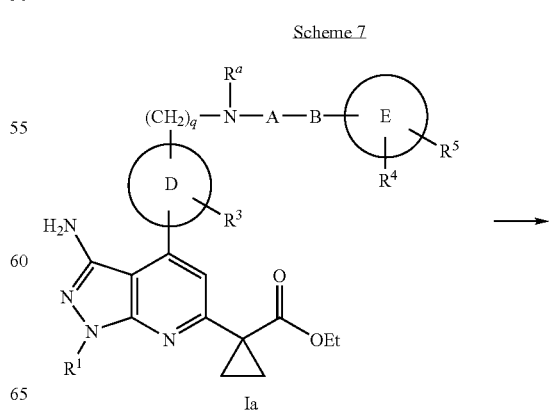

-continued

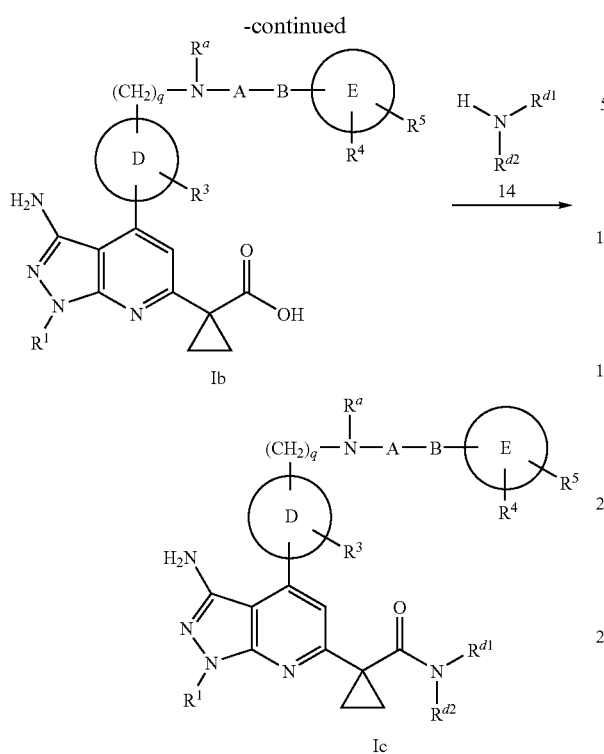

Scheme 7 Synthesis of compounds of general formula Ic, wherein A, B, D, E, $R^a$, $R^1$, $R^2$, $R^3$, $R^4$, $R^5$, $R^{d1}$, $R^{d2}$ and q are as defined in the description and claims of this invention.

As a more specific exemplification of the above-described chemical interconversions, Scheme 7 depicts the transformation of esters of general formula Ia into amides of general formula Ic, via ester saponification, for example by treatment with a base, such as, for example, NaOH, providing carboxylic acids of general formula Ib, followed by reaction with amines of general formula 14 in the presence of a coupling agent, as described above, such as, for example, T3P.

SYNTHESIS OF KEY INTERMEDIATES

In the subsequent paragraphs detailed procedures for the synthesis of key intermediates for compounds of the present invention are described.

General Procedure 1 (GP 1)

Pyridone Multi-Component Coupling

See Schemes 1, 5 and 6

To a suspension of ammonium acetate (6-8 eq.) in EtOH (60 mL per mmol NH$_4$OAc) were added successively the respective methylketone component (1 eq.), methyl cyanoacetate (1 eq.), and 4-nitrobenzaldehyde (1 eq.). The resulting mixture was stirred at reflux for 1-5 h and subsequently for 16 h at r.t. The precipitate was filtered off, washed with EtOH and hexane and dried to yield the pyridone in sufficient purity for use in subsequent transformations without additional purification steps. Concentration of the filtrate gave rise to additional pyridone precipitation improving the overall yield of the multi-component coupling.

Exemplification of GP 1

Preparation of 6-Cyclopropyl-4-(4-nitro-phenyl)-2-oxo-1,2-dihydro-pyridine-3-carbonitrile

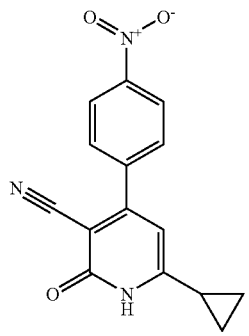

Reaction of 17.9 g ammonium acetate (233 mmol, 7 eq.), 3.5 ml methyl cyanoacetate (40 mmol, 1.2 eq.), 3.8 ml 1-cyclopropyl-ethanone (38 mmol, 1.15 eq.), and 5 g 4-nitrobenzaldehyde (33 mmol, 1 eq.) yielded 3.23 g product (11.5 mmol, 35% yield).

$^1$H-NMR (d6-DMSO; 300 MHz): 12.82 (br. s, 1H); 8.37 (d, 2H); 7.88 (d, 2H); 6.10 (s, 1H); 2.00 (m, 1H); 1.00-1.25 (m, 4H).

General Procedure 2 (Gp 2)

Triflate Formation

See Schemes 1 and 5

To a solution of the respective pyridone (1 eq.) in DCM (8 mL per mmol pyridone) was added pyridine (1.5 eq.) and subsequently at 0° C. dropwise trifluoromethanesulphonic acid anhydride (1.5 eq.). Alternatively, the reaction was run in pyridine without additional DCM. The resulting mixture was gradually warmed to room temperature and stirring was continued for 2 h. The reaction mixture was diluted with DCM and quenched with water. The aqueous layer was extracted with DCM and the combined organic layers were dried and concentrated in vacuo. Flash column chromatography provided the 2-pyridyl triflates.

Exemplification of GP 2

Preparation of Trifluoromethanesulphonic acid 3-cyano-6-cyclopropyl-4-(4-nitro-phenyl)-pyridin-2-yl ester

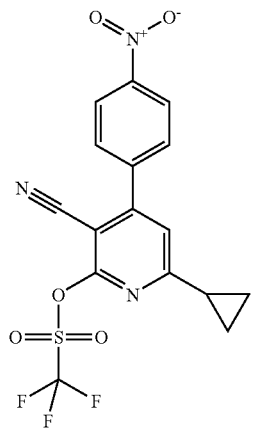

Reaction of 1.5 g 6-cyclopropyl-4-(4-nitro-phenyl)-2-oxo-1,2-dihydro-pyridine-3-carbonitrile (5.3 mmol, 1 eq.), and 2.69 ml trifluoromethanesulphonic acid anhydride (16 mmol, 3 eq.) in pure pyridine yielded 1.49 g product (3.6 mmol mmol, 68% yield).

$^1$H-NMR (CDCl$_3$; 300 MHz): 8.41 (d, 2H); 7.78 (d, 2H); 7.40 (s, 1H); 2.15 (m, 1H); 1.20-1.30 (m, 4H).

General Procedure 3 (GP 3)

Nitro Reduction

See Schemes 1 and 3

The respective nitro compound (1 eq.) was dissolved in EtOH (5-7 mL per mmol nitro compound) and treated in a counterflow of argon portionwise with SnCl$_2$.2H$_2$O (5 eq.). The resulting slurry was vigorously stirred and heated to 70° C. for 30 to 120 min. The reaction mixture was poured into 25% NH$_3$ solution (25 mL per mmol nitro compound), extracted with EtOAc, the combined organic layers were washed with brine twice, dried and concentrated in vacuo. The resulting aniline was usually used for subsequent reactions without additional purification steps.

Exemplification of GP 3

Preparation of Trifluoromethanesulphonic acid 4-(4-amino-phenyl)-3-cyano-6-cyclopropyl-pyridin-2-yl ester

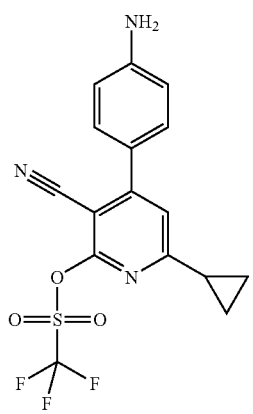

In analogy to GP 3, reaction of 1.49 g trifluoromethanesulphonic acid 3-cyano-6-cyclopropyl-4-(4-nitro-phenyl)-pyridin-2-yl ester (3.6 mmol, 1 eq.) with 4.1 g tin(II) chloride dihydrate (18.19 mmol, 5 eq.) in 20 mL EtOH yielded 1.2 g of the desired aniline (3.1 mmol, 86% yield).

$^1$H-NMR (d$_6$-DMSO; 300 MHz): 7.76 (s, 1H); 7.51 (d, 2H); 6.70 (d, 2H); 5.92 (br. s, 2H); 2.31 (m, 1H); 1.15-1.20 (m, 2H); 0.96-1.00 (m, 2H).

General Procedure 4 (GP 4)

Urea Formation

See Schemes 1 and 4

The respective aniline (1 eq.) was dissolved in DCM (4 mL per mmol aniline) and treated with the respective commercially available isocyanate (1-1.2 eq.). The reaction mixture was stirred at room temperature until TLC indicated complete consumption of the starting aniline (usually 16 h). The reaction mixture was concentrated in vacuo. In most cases, the crude urea was used in the subsequent cyclization without further purification, however, in cases with incomplete urea formation (as judged by TLC) flash column chromatography was applied for purification.

Exemplification of GP 4

Preparation of Trifluoromethanesulphonic acid 3-cyano-6-cyclopropyl-4-{4-[3-(2-fluoro-phenyl)-ureido]-phenyl}-pyridin-2-yl ester

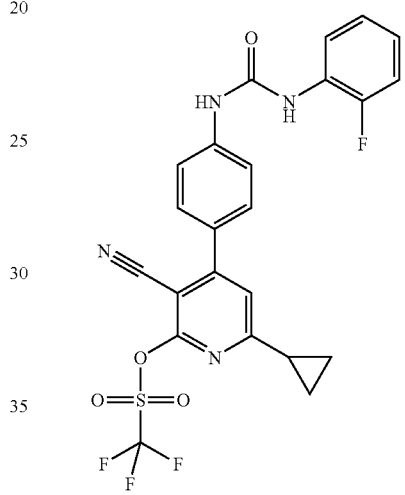

In analogy to GP 4, reaction of 200 mg trifluoromethanesulphonic acid 4-(4-amino-phenyl)-3-cyano-6-cyclopropyl-pyridin-2-yl ester (0.522 mmol) and 71 µl 1-fluoro-2-isocyanato-benzene yielded 179 mg product (0.343 mmol, 66% yield).

$^1$H-NMR (d6-DMSO, 300 MHz): 9.42 (1H); 8.69 (1H); 8.10 (1H); 7.83 (1H); 7.61-7.74; (4H); 7.21 (1H); 7.11 (1H); 7.00 (1H); 2.32 (1H); 1.19 (2H); 0.99 (2H).

General Procedure 5 (GP 5)

Pyrazolopyridine Formation

See Schemes 1 and 4

The crude or purified urea (1 eq.; compare to GP 4) was dissolved in 1-PrOH (12-15 mL per mmol urea) and treated optionally with Et$_3$N (1.5 eq) and subsequently with 80% hydrazine hydrate (1-3 eq.) or a substituted hydrazine (1-3 eq.). The resulting mixture was stirred at 100° C. for 3 h, concentrated in vacuo and the pyrazolopyridine product was isolated by flash column chromatography followed by re-crystallization and/or preparative HPLC purification.

Exemplification of GP 5

Preparation of 1-[4-(3-amino-6-cyclopropyl-1H-pyrazolo[3,4-b]pyridin-4-yl)-phenyl]-3-(2-fluoro-phenyl)-urea

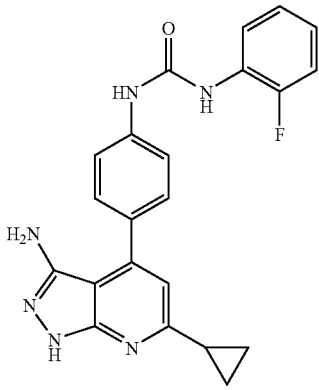

In analogy to the GP 5, reaction of 175 mg trifluoromethanesulphonic acid 3-cyano-6-cyclopropyl-4-{4-[3-(2-fluoro-phenyl)-ureido]-phenyl}-pyridin-2-yl ester (0.336 mmol) with 62 µl 80% hydrazine hydrate in 1-propanol yielded 35 mg product (0.087 mmol, 26% yield).

$^1$H-NMR (d6-DMSO, 300 MHz): 11.95 (1H); 9.26 (1H); 8.60 (1H); 8.12 (1H); 7.59 (2H); 7.50 (2H); 7.20 (1H); 7.10 (1H); 6.99 (1H); 6.80 (1H); 4.45 (2H); 2.15 (1H); 0.94 (4H).

Preparation of 1-[4-(3-amino-6-cyclo-propyl-1H-pyrazolo-[3,4-b]pyridin-4-yl)-phenyl]-3-m-tolyl-urea

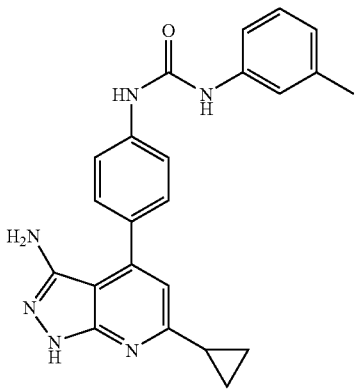

$^1$H-NMR: (d6-DMSO, 400 MHz): 11.96 (s, 1H); 8.83 (s, 1H); 8.61 (s, 1H); 7.60 (d, 2H); 7.48 (d, 2H); 7.26 (br. s, 1H); 7.20 (m, 1H); 7.12 (t, 1H); 6.81 (s, 1H); 6.77 (br. d, 1H); 4.46 (br. s, 2H); 2.25 (s, 3H); 2.15 (m, 1H); 0.96 (m, 4H).

Preparation of 1-[4-(3-amino-6-cyclopropyl-1H-pyrazolo[3,4-b]pyridin-4-yl)-phenyl]-3-phenyl-urea

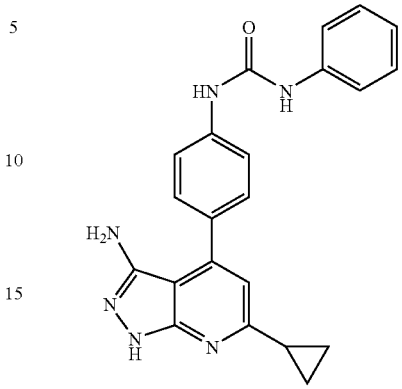

$^1$H-NMR (d6-DMSO, 400 MHz): 11.97 (1H); 8.91 (1H); 8.78 (1H); 7.63 (2H); 7.45-7.59 (4H); 7.30 (2H); 6.99 (1H); 6.86 (1H); 4.48 (2H); 2.19 (1H); 1.00 (4H).

General Procedure 6 (GP 6)

N1-Alkylation of 1H-pyrazolopyridines

See Scheme 4

The respective 1H-pyrazolopyridine was dissolved in dry DMF under an atmosphere of argon and treated with sodium hydride and subsequently stirred at 50° C. for 1 h. A solution of the respective alkyl halide in DMF was added dropwise and stirring was continued at 50° C. for 1 h. [In cases were the respective halide is only available as a salt (e.g. hydrochloride or hydrobromide salt), this salt was dissolved in DMF and treated with excess Et$_3$N, and the resulting slurry was added to the deprotonated 1H-pyrazolopyridine upon filtration through a Millipore filter.] The reaction mixture was diluted with EtOAc, quenched with water, the aqueous layer was extracted with EtOAc and the combined organic layers were dried and concentrated in vacuo. Flash column chromatography optionally followed by recrystallization or preparative HPLC purification yielded the desired alkylated pyrazolopyridines.

General Procedure 7 (GP 7)

Triphosgene-Mediated Urea Formation

See Scheme 2

The aniline (1.2 eq.) was dissolved in 10 mL acetonitrile and treated with triphosgene (0.2 mmol, 0.4 eq.) and stirred at room temperature for 1 h upon which a 2-pyridyltriflate (e.g. of general formula 5) was added and stirring was continued at r.t. for 16 h. The reaction mixture was concentrated and the crude urea was either purified by column chromatography or used without additional purification steps in the subsequent cyclization with a hydrazine (as described in GP 5).

General Procedure 8 (GP 8)

Sulphonylation and Pyrazolopyridine Formation

See Scheme 1, wherein A is —S(O)$_2$—

A solution of the respective aniline (1 eq.) was treated with triethylamine (1.5 eq.) and the respective sulphonyl chloride (1.1 eq.) in THF and stirred at room temperature until TLC indicated complete turnover of the starting aniline. Afterwards, the reaction mixture was poured into ice-cold 1 N hydrochloric acid. It was stirred for 10 minutes and then extracted with ethyl acetate. The organic layer was washed with brine and dried over sodium sulphate and concentrated in vacuo. The crude sulphonyl amide was either used without purification in the subsequent cyclization or further purified by column chromatography. The crude or purified sulphonyl amide was dissolved in 1-PrOH and treated optionally with Et$_3$N (1.5 eq) and subsequently with 80% hydrazine hydrate (1-3 eq.) or a substituted hydrazine (1-3 eq.). The resulting mixture was stirred at 100° C. for 3 h, concentrated in vacuo and the pyrazolopyridine product was isolated by flash column chromatography followed by re-crystallization and/or preparative HPLC purification.

Exemplification of GP 8

Preparation of N-[4-(3-amino-6-cyclo-propyl-1H-pyrazolo-[3,4-b]pyridin-4-yl)-phenyl]-benzene-sulphonamide

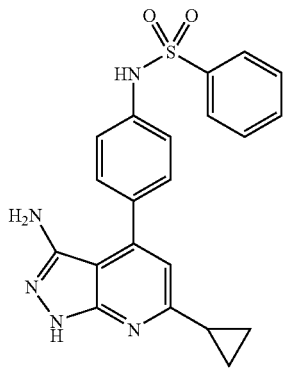

$^1$H-NMR (d6-DMSO, 400 MHz): 11.98 (s, 1H); 10.56 (s, 1H); 7.78 (d, 2H); 7.50-7.65 (m, 3H); 7.41 (d, 2H); 7.20 (d, 2H); 6.74 (s, 1H); 4.35 (s, 2H); 2.10 (m, 1H); 0.90 (m, 4H).

Preparation of N-[4-(3-amino-6-cyclo-propyl-1H-pyrazolo-[3,4-b]pyridin-4-yl)-phenyl]-4-methyl-benzenesulphonamide

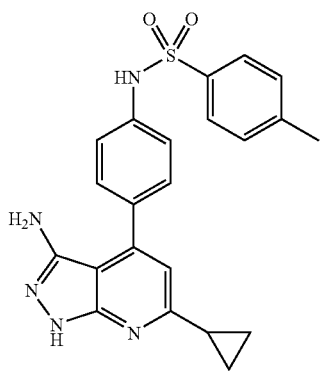

$^1$H-NMR (d6-DMSO, 300 MHz): 11.92 (s, 1H); 10.70 (s, 1H); 7.67 (d, 2H); 7.41 (d, 2H); 7.32 (d, 2H); 7.19 (d, 2H); 6.73 (s, 1H); 4.32 (s, 2H); 2.30 (s, 3H); 2.12 (m, 1H); 0.92 (m, 4H).

Preparation of N-[4-(3-amino-6-cyclo-propyl-1H-pyrazolo-[3,4-b]pyridin-4-yl)-phenyl]-3-nitro-benzenesulphonamide

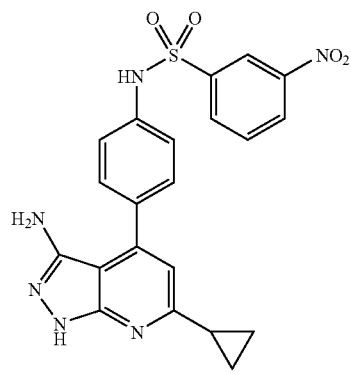

$^1$H-NMR (d6-DMSO, 300 MHz): 11.96 (s, 1H); 10.73 (s, 1H); 8.51 (m, 1H); 8.42 (br. d, 1H); 8.16 (br. d, 1H); 7.73 (t, 1H); 7.46 (d, 2H); 7.22 (d, 2H); 6.75 (s, 1H); 4.30 (s, 2H); 2.12 (m, 1H); 0.91 (m, 4H).

Preparation of N-[4-(3-amino-6-cyclo-propyl-1H-pyrazolo-[3,4-b]pyridin-4-yl)-phenyl]-3-methyl-benzenesulphonamide

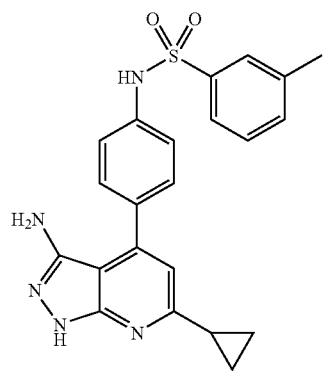

$^1$H-NMR (d6-DMSO, 400 MHz): 11.97 (s, 1H); 10.74 (s, 1H); 7.58 (m, 1H); 7.40-7.50 (m, 5H); 7.20 (d, 2H); 6.76 (s, 1H); 4.32 (s, 2H); 2.30 (s, 3H); 2.10 (m, 1H); 0.93 (m, 4H).

General Procedure 9 (GP 9)

Amide Formation and Cyclization

The respective aniline (1 eq.) was dissolved in DCM (12 mL per mmol aniline) and treated with pyridine (1.5 eq.) and the respective carboxylic acid chloride (1.2 eq.; which was prepared by treating the respective carboxylic acid with thionyl chloride followed by concentration in vacuo). The reaction mixture was stirred at room temperature until TLC indicated complete consumption of the starting aniline (usually 16 h). The reaction mixture was quenched with NaHCO$_3$ and extracted with ethyl acetate. The organic layers were dried and concentrated in vacuo. In most cases, the crude amide was used in the subsequent cyclization without further purification, however, in cases with incomplete amide formation (as judged by TLC) flash column chromatography was applied for purification. The crude or purified carboxylic amide was dissolved in 1-PrOH and treated optionally with Et$_3$N (1.5 eq) and subsequently with 80% hydrazine hydrate (1-3 eq.) or a substituted hydrazine (1-3 eq.). The resulting mixture was stirred at 100° C. for 3 h, concentrated in vacuo and the pyrazolopyridine product was isolated by flash column chromatography followed by re-crystallization and/or preparative HPLC purification.

General Procedure 10 (GP 10)

Ester Saponification

The carboxylic acid ester was treated with EtOH and aqueous sodium hydroxide solution (1 mol per litre) and stirred for 3 hours at 80° C. To the cold solution was added the same volume of water. The mixture was acidified with a 20% solution of citric acid. The precipitate was filtered off, washed with water and dried to yield the carboxylic acid.

General Procedure 11 (GP 11)

Amide Formation

The carboxylic acid (1 eq.) was suspended in DCM and treated with the amine (1.3 eq.) and 4-methylmorpholine (5 eq.). The suspension was stirred for 10 minutes at room temperature and then cooled with ice. 2,4,6-tripropyl-[1,3,5,2,4,6]trioxa-triphosphinane 2,4,6-trioxide (T3P; 2 eq.) was added and the solution stirred over night at room temperature. The mixture was concentrated in vacuo, taken up in sodium bicarbonate solution and stirred. The precipitate was filtered off, washed with water and dried to yield the amide. In some cases additional purification steps (flash column chromatography and/or preparative HPLC) were necessary.

Intermediate 1.1

Preparation of 1-[5-Cyano-4-(4-nitro-phenyl)-6-oxo-1,6-dihydro-pyridin-2-yl]-cyclo-propanecarboxylic acid ethyl ester

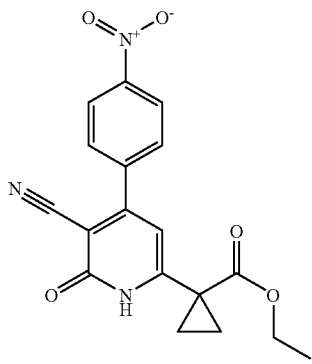

In analogy to GP 1, reaction of 28.9 g ammonium acetate (375 mmol, 8 eq.), 5 ml ethyl cyanoacetate (47.3 mmol, 1 eq.), 7.32 g 1-acetyl-cyclopropanecarboxylic acid ethyl ester (47 mmol, 1 eq.), and 7.08 g 4-nitrobenzaldehyde (47 mmol, 1 eq.) yielded 7.2 g product (43% yield).

$^1$H-NMR (d$_6$-DMSO; 300 MHz): 13.12 (br. s, 1H); 8.38 (d, 2H); 7.94 (d, 2H); 6.51 (br. s, 1H); 4.10 (q, 2H); 1.49 (br. s, 4H); 1.16 (t, 3H).

Intermediate 1.2

Preparation of 1-[5-Cyano-4-(4-nitro-phenyl)-6-trifluoromethanesulfonyloxy-pyridin-2-yl]-cyclopropanecarboxylic acid ethyl ester

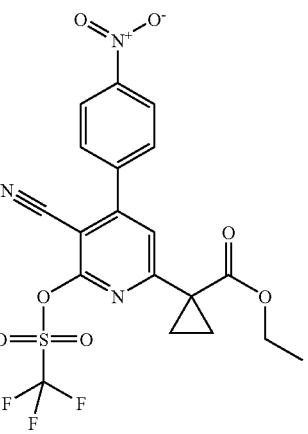

In analogy to GP 2, reaction of 7.2 g Intermediate 1.1 (20.4 mmol, 1 eq.), 2.5 mL dry pyridine (30.6 mmol, 1.5 eq.), 5.14 ml trifluoromethanesulfonic acid anhydride (30.6 mmol, 1.5 eq.) in 320 mL DCM yielded 4.2 g 2-pyridyl triflate (8.65 mmol, 43% yield).

$^1$H-NMR (d$_6$-DMSO; 300 MHz): 8.47 (d, 2H); 8.25 (s, 1H); 8.05 (d, 2H); 4.14 (q, 2H); 1.75 (m, 2H); 1.62 (m, 2H); 1.17 (t, 3H).

Intermediate 1.3

Preparation of 1-[4-(4-Amino-phenyl)-5-cyano-6-trifluoromethanesulfonyloxy-pyridin-2-yl]-cyclopropanecarboxylic acid ethyl ester

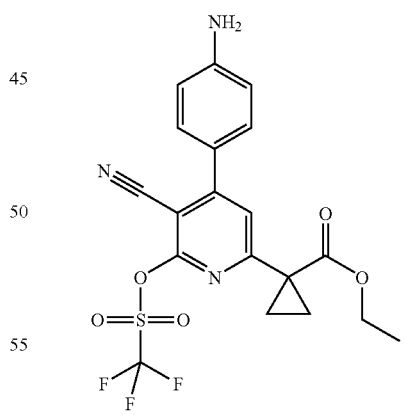

In analogy to GP 3, reaction of 3.8 g Intermediate 1.2 (7.8 mmol, 1 eq.) with 8.83 g tin(II) chloride dihydrate (39.1 mmol, 5 eq.) in 200 mL EtOH yielded 3.57 g of the aniline (7.38 mmol, 94% yield), which was used without further purification.

$^1$H-NMR (d$_6$-DMSO; 300 MHz): 8.01 (s, 1H); 7.55 (d, 2H); 6.72 (d, 2H); 6.00 (br. s, 2H); 4.13 (q, 2H); 1.66 (m, 2H); 1.56 (m, 2H); 1.16 (t, 3H).

Intermediate 1.4

Preparation of 1-{5-Cyano-4-[4-(3-phenyl-ureido)-phenyl]-6-trifluoromethane-sulfonyloxy-pyridin-2-yl}-cyclopropanecarboxylic acid ethyl ester

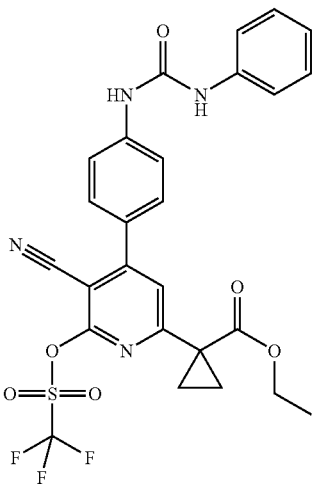

In analogy to GP 4, reaction of 890 mg Intermediate 1.3 (1.95 mmol, 1 eq.) with 0.25 mL isocyanatobenzene (2.35 mmol, 1.2 eq.) in 15 mL DCM yielded 820 mg of the urea (1.43 mmol, 73% yield), which was used without further purification.

$^1$H-NMR (d$_6$-DMSO; 300 MHz): 9.08 (s, 1H); 8.83 (s, 1H); 8.14 (s, 1H); 7.72 (m, 4H); 7.48 (d, 2H); 7.30 (m, 2H); 7.00 (m, 1H); 4.15 (q, 2H); 1.71 (m, 2H); 1.60 (m, 2H); 1.18 (t, 3H).

MS (ESI): [M+H]$^+$=575 (100%).

Intermediate 1.5

Preparation of 1-(5-Cyano-6-trifluoromethanesulfonyloxy-4-{4-[3-(3-trifluoro-methyl-phenyl)-ureido]-phenyl}-pyridin-2-yl)-cyclopropanecarboxylic acid ethyl ester

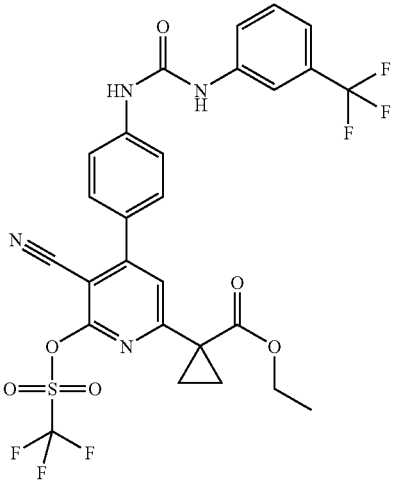

In analogy to GP 4, reaction of 3.3 g Intermediate 1.4 (7.25 mmol, 1 eq.) with 1.63 g 1-isocyanato-3-trifluoromethyl-benzene (8.7 mmol, 1.2 eq.) in 150 mL DCM yielded 3.78 g of the urea (5.9 mmol, 81% yield), after purification by flash column chromatography.

$^1$H-NMR (d$_6$-DMSO; 300 MHz): 9.22 (s, 1H); 9.21 (s, 1H); 8.15 (s, 1H); 8.04 (s, 1H); 7.73 (m, 4H); 7.60 (m, 1H); 7.54 (m, 1H); 7.34 (m, 1H); 4.15 (q, 2H); 1.71 (m, 2H); 1.60 (m, 2H); 1.18 (t, 3H).

Intermediate 1.6

Preparation of 1-{3-Amino-4-[4-(3-phenyl-ureido)-phenyl]-1H-pyrazolo[3,4-b]pyridin-6-yl}-cyclopropanecarboxylic acid ethyl ester

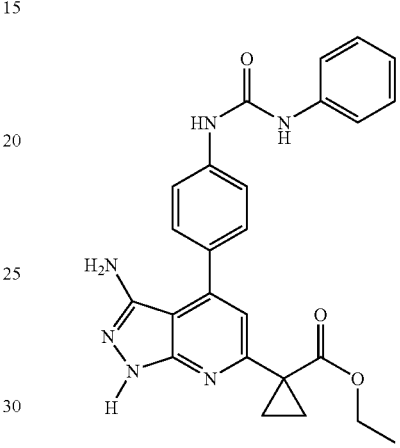

In analogy to GP 5, reaction of Intermediate 1.4 (420 mg, 0.73 mmol, 1 eq.) with 110 µL 80% hydrazine hydrate (2.19 mmol, 3 eq.) in 20 mL 1-PrOH yielded 242 mg of the 1H-pyrazolopyridine (0.53 mmol, 72% yield).

$^1$H-NMR (d$_6$-DMSO; 300 MHz): 12.19 (br. s, 1H); 8.92 (br. s, 1H); 8.76 (br. s, 1H); 7.65 (d, 2H); 7.53 (m, 2H); 7.48 (m, 2H); 7.30 (m, 2H); 7.02 (s, 1H); 6.99.

Intermediate 1.7

Preparation of 1-[3-Amino-4-(4-nitro-phenyl)-1H-pyrazolo[3,4-b]pyridin-6-yl]-cyclopropanecarboxylic acid ethyl ester

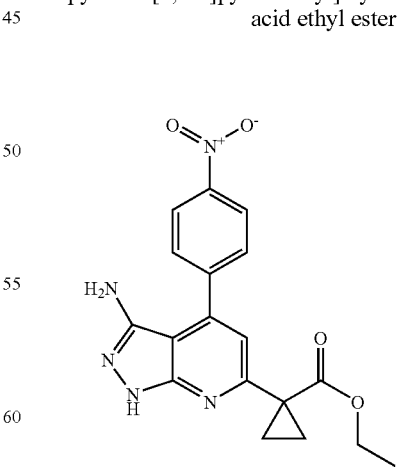

In an adoption of GP 5, reaction of Intermediate 1.2 (1.1 g, 2.27 mmol, 1 eq.) with 330 µL 80% hydrazine hydrate (6.8 mmol, 3 eq.) in 55 mL 1-PrOH yielded 0.83 g of the 1H-pyrazolopyridine (2.26 mmol, 99% yield).

$^1$H-NMR (d$_6$-DMSO; 400 MHz): 12.37 (s, 1H); 8.38 (d, 2H); 7.87 (d, 2H); 7.16 (s, 1H); 4.67 (br. s, 2H); 4.09 (q, 2H); 1.54 (m, 2H); 1.52 (m, 2H); 1.13 (t, 3H).

MS (ESI): [M+H]$^+$=368 (100%). Intermediate 2.1

Preparation of 1-[5-Cyano-4-(3-nitro-phenyl)-6-oxo-1,6-dihydro-pyridin-2-yl]-cyclopropanecarboxylic acid ethyl ester

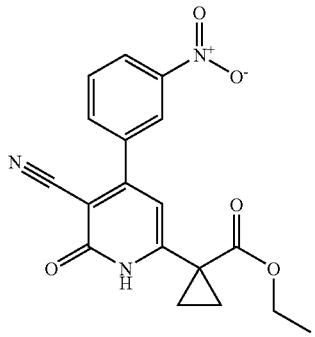

In analogy to GP 1, reaction of 30.8 g ammonium acetate (400 mmol), 11.3 g ethyl cyanoacetate (100 mmol), 15.6 g 1-acetyl-cyclopropanecarboxylic acid ethyl ester (100 mmol), and 15.1 g 3-nitrobenzaldehyde (100 mmol) yielded 3.5 g product (10% yield).

$^1$H-NMR (d$_6$-DMSO; 300 MHz): 13.10 (br. s, 1H); 8.45 (s, 1H); 8.40 (d, 1H); 8.15 (d, 1H); 7.85 (t, 1H); 6.60 (br. s, 1H); 4.10 (q, 2H); 1.50 (m, 4H); 1.20 (t, 3H).

Intermediate 2.2

Preparation of 1-[5-Cyano-4-(3-nitro-phenyl)-6-trifluoromethanesulfonyloxy-pyridin-2-yl]-cyclopropanecarboxylic acid ethyl ester

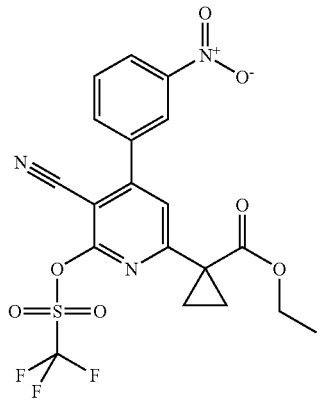

In analogy to GP 2, reaction of 4.7 g Intermediate 2.1 (13 mmol), 4.2 mL dry pyridine (53 mmol), 3.5 ml trifluoromethanesulfonic acid anhydride (21 mmol) in 150 mL DCM yielded 4.8 g 2-pyridyl triflate (74% yield).

$^1$H-NMR (d$_6$-DMSO; 300 MHz): 8.63 (br. s, 1H); 8.48 (d, 1H); 8.30 (s, 1H); 8.24 (d, 1H); 7.95 (t, 1H); 4.15 (q, 2H); 1.75 (m, 2H); 1.65 (m, 2H); 1.20 (t, 3H).

Intermediate 2.3

Preparation of 1-[4-(3-Amino-phenyl)-5-cyano-6-trifluoromethanesulfonyloxy-pyridin-2-yl]-cyclopropanecarboxylic acid ethyl ester

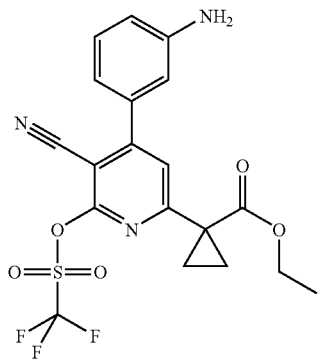

In analogy to GP 3, reaction of 2.07 g Intermediate 2.2 (4.26 mmol, 1 eq.) with 4.81 g tin(II) chloride dihydrate (21.3 mmol, 5 eq.) in 100 mL EtOH yielded 1.4 g of the aniline (3.07 mmol, 72% yield), which was used without further purification.

$^1$H-NMR (d$_6$-DMSO; 300 MHz): 8.09 (s, 1H); 7.24 (t, 1H); 6.84 (s, 1H); 6.81 (d, 1H); 6.78 (d, 1H); 5.49 (br. s, 2H); 4.14 (q, 2H); 1.72 (m, 2H); 1.60 (m, 2H); 1.17 (t, 3H).

MS (ESI): [M+H]$^+$=456.

Intermediate 2.4

Preparation of 1-(5-Cyano-6-trifluoromethanesulfonyloxy-4-{3-[3-(3-trifluoromethyl-phenyl)-ureido]-phenyl}-pyridin-2-yl)-cyclopropanecarboxylic acid ethyl ester

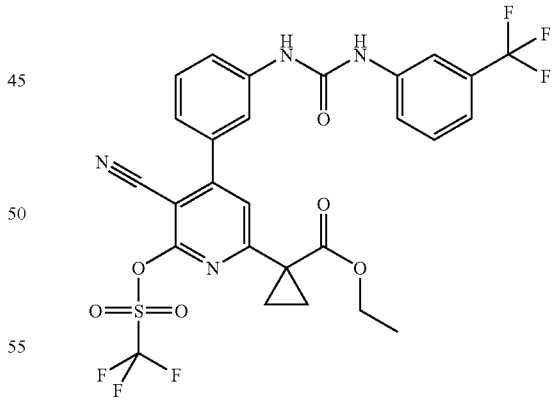

In analogy to GP 4, reaction of 1.1 g Intermediate 2.3 (2.4 mmol, 1 eq.) with 0.54 g isocyanatobenzene (2.9 mmol, 1.2 eq.) in 50 mL DCM yielded 1.6 g of the urea (2.5 mmol, 100% yield), which was used without further purification.

$^1$H-NMR (d$_6$-DMSO; 300 MHz): 9.17 (s, 1H); 9.12 (s, 1H); 8.18 (s, 1H); 8.05 (s, 1H); 7.91 (s, 1H); 7.66 (d, 1H); 7.57 (m, 2H); 7.52 (t, 1H); 7.37 (d, 1H); 7.33 (d, 1H); 4.16 (q, 2H); 1.73 (m, 2H); 1.62 (m, 2H); 1.19 (t, 3H).

MS (ESI): [M+H]$^+$=643.

Intermediate 3.1

Preparation of 1-(5-Cyano-4-{4-[3-(2-fluoro-5-methyl-phenyl)-ureido]-phenyl}-6-trifluoromethanesulfonyloxy-pyridin-2-yl)-cyclopropanecarboxylic acid ethyl ester

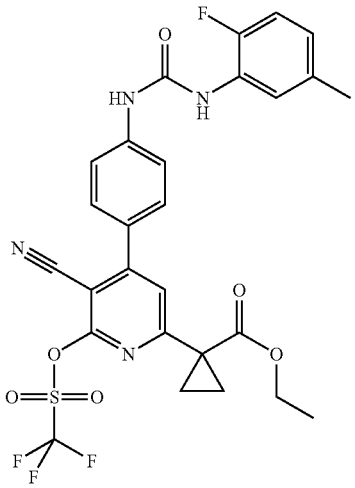

In analogy to GP 4, reaction of 0.95 g Intermediate 1.3 (2.1 mmol, 1 eq.) with 0.38 g 2-fluoro-5-methyl-1-isocyanatobenzene (2.5 mmol, 1.2 eq.) in 25 mL DCM yielded 1.0 g of the urea (66% yield), which was used without further purification.

$^1$H-NMR (d$_6$-DMSO; 400 MHz): 9.45 (s, 1H); 8.64 (s, 1H); 8.15 (s, 1H); 7.99 (d, 1H); 7.76 (d, 2H); 7.70 (d, 2H); 7.13 (dd, 1H); 6.83 (m, 1H); 4.14 (q, 2H); 2.28 (s, 3H); 1.71 (m, 2H); 1.60 (m, 2H); 1.18 (t, 3H).

MS (ESI): [M+H]$^+$=607.

The following synthetic intermediates 4.1 to 4.17 were synthesized in analogy to the before described reactions starting from commercially available 1-cyclopropyl-ethanone, 1-cyclobutyl-ethanone, 1-cyclohexyl-ethanone, 1-(2-phenyl-cyclopropyl)-ethanone, or (3-acetyl-2,2-dimethyl-cyclobutyl)-acetic acid methyl ester (accessible by standard esterification protocols, which are well known to the person skilled in the art, from commercially available cis-pinonic acid) respectively.

| Intermediate | Structure | Name | Analytical data |
|---|---|---|---|
| 4.1 | 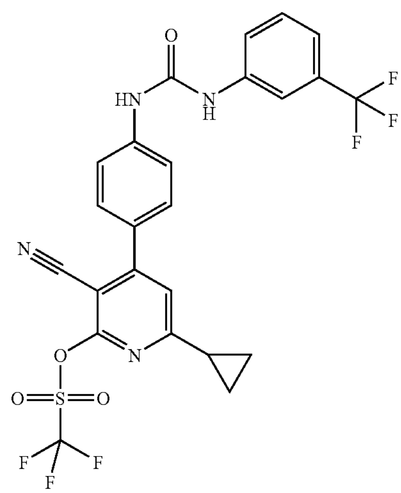 | Trifluoromethanesulfonic acid 3-cyano-6-cyclopropyl-4-{4-[3-(3-trifluoromethyl-phenyl)-ureido]-phenyl}-pyridin-2-yl ester | $^1$H-NMR (d$_6$-DMSO; 300 MHz): 9.20 (s, 1 H); 9.19 (s, 1 H); 8.04 (s, 1 H); 7.88 (s, 1 H); 7.72 (m, 4 H); 7.60 (m, 1 H); 7.54 (t, 1 H); 7.34 (d, 1 H); 2.38 (m, 1 H); 1.23 (m, 2 H); 1.03 (m, 2 H). |
| 4.2 | 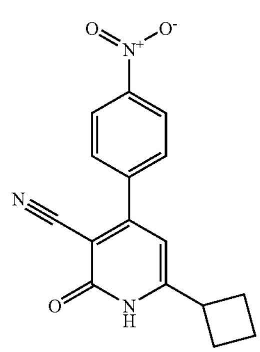 | 6-Cyclobutyl-4-(4-nitro-phenyl)-2-oxo-1,2-dihydro-pyridine-3-carbonitrile | $^1$H-NMR (d$_6$-DMSO; 300 MHz): 12.66 (br. s, 1 H); 8.39 (d, 2 H); 7.92 (d, 2 H); 6.42 (s, 1 H); 3.51 (m, 1 H); 2.26 (m, 4 H); 1.96 (m, 1 H); 1.80 (m, 1 H). |

| Inter-mediate | Structure | Name | Analytical data |
|---|---|---|---|
| 4.3 | 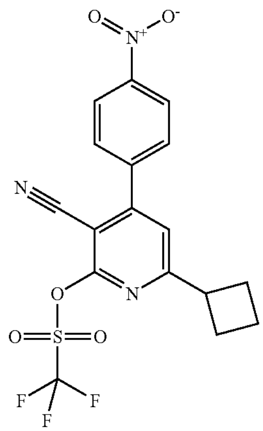 | Trifluoro-methanesulfonic acid 3-cyano-6-cyclobutyl-4-(4-nitro-phenyl)-pyridin-2-yl ester | $^1$H-NMR (d$_6$-DMSO; 400 MHz): 8.45 (d, 2 H); 8.03 (d, 2 H); 7.84 (s, 1 H); 3.86 (m, 1 H); 2.33 (m, 4 H); 2.04 (m, 1 H); 1.90 (m, 1 H). |
| 4.4 | 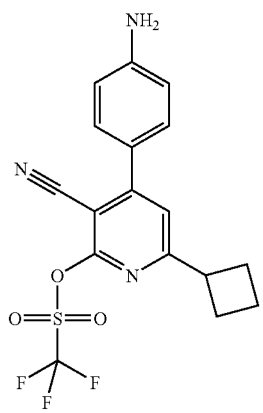 | Trifluoro-methanesulfonic acid 4-(4-amino-phenyl)-3-cyano-6-cyclobutyl-pyridin-2-yl ester | $^1$H-NMR (d$_6$-DMSO; 400 MHz): 7.59 (s, 1 H); 7.52 (d, 2 H); 6.70 (d, 2 H); 5.95 (br. s, 2 H); 3.77 (m, 1 H); 2.29 (m, 4 H); 2.02 (m, 1 H); 1.86 (m, 1 H). |
| 4.5 | 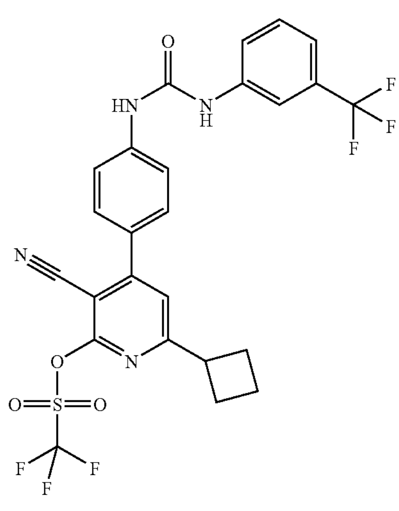 | Trifluoro-methanesulfonic acid 3-cyano-6-cyclobutyl-4-{4-[3-(3-trifluoromethyl-phenyl)-ureido]-phenyl}-pyridin-2-yl ester | $^1$H-NMR (d$_6$-DMSO; 400 MHz): 9.20 (s, 2 H); 8.03 (s, 1 H); 7.72 (m, 5 H); 7.60 (d, 1 H); 7.54 (t, 1 H); 7.34 (d, 1 H); 3.83 (qui, 1 H); 2.32 (m, 4 H); 2.04 (q, 1 H); 1.89 (m, 1 H). |

| Intermediate | Structure | Name | Analytical data |
|---|---|---|---|
| 4.6 | 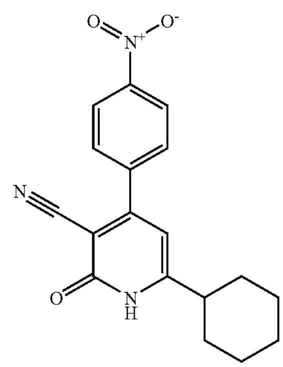 | 6-Cyclohexyl-4-(4-nitro-phenyl)-2-oxo-1,2-dihydro-pyridine-3-carbonitrile | $^1$H-NMR (d$_6$-DMSO; 300 MHz): 12.65 (br. s, 1 H); 8.38 (d, 2 H); 7.91 (d, 2 H); 6.36 (s, 1 H); 2.57 (m, 1 H); 1.81 (m, 4 H); 1.67 (m, 1 H); 1.50 (m, 2 H); 1.24 (m, 3 H). |
| 4.7 | 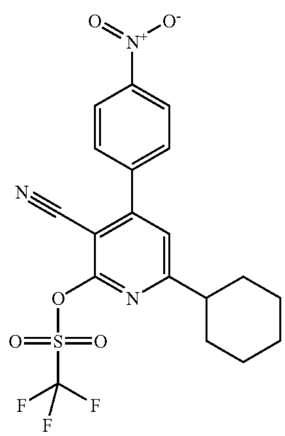 | Trifluoro-methanesulfonic acid 3-cyano-6-cyclohexyl-4-(4-nitro-phenyl)-pyridin-2-yl ester | $^1$H-NMR (d$_6$-DMSO; 400 MHz): 8.45 (d, 2 H); 8.05 (d, 2 H); 7.89 (s, 1 H); 2.91 (m, 1 H); 1.92 (m, 2 H); 1.82 (m, 2 H); 1.71 (m, 1 H); 1.52 (m, 2 H); 1.38 (m, 2 H); 1.23 (m, 1 H). |
| 4.8 | 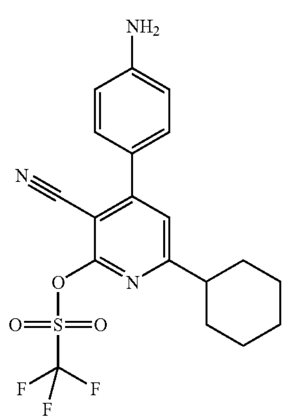 | Trifluoro-methanesulfonic acid 4-(4-amino-phenyl)-3-cyano-6-cyclohexyl-pyridin-2-yl ester | $^1$H-NMR (d$_6$-DMSO; 300 MHz): 7.64 (s, 1 H); 7.54 (d, 2 H); 6.71 (d, 2 H); 5.95 (br. s, 2 H); 2.81 (m, 1 H); 1.93-1.64 (m, 5 H); 1.56-1.13 (m, 5 H). |

-continued

| Intermediate | Structure | Name | Analytical data |
|---|---|---|---|
| 4.9 | 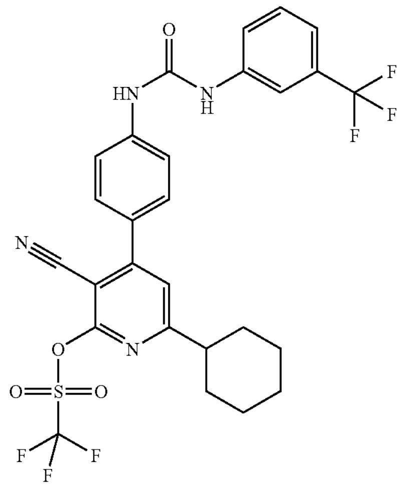 | Trifluoromethanesulfonic acid 3-cyano-6-cyclohexyl-4-{4-[3-(3-trifluoromethyl-phenyl)-ureido]-phenyl}-pyridin-2-yl ester | $^1$H-NMR (d$_6$-DMSO; 400 MHz): 9.20 (s, 1 H); 9.19 (s, 1 H); 8.03 (s, 1 H); 7.74 (m, 5 H); 7.60 (d, 1 H); 7.53 (m, 1 H); 7.34 (d, 1 H); 2.87 (t, 1 H); 1.90 (d, 2 H); 1.81 (d, 2 H); 1.71 (d, 1 H); 1.50 (q, 2 H); 1.37 (q, 2 H); 1.23 (t, 1 H). |
| 4.10 | 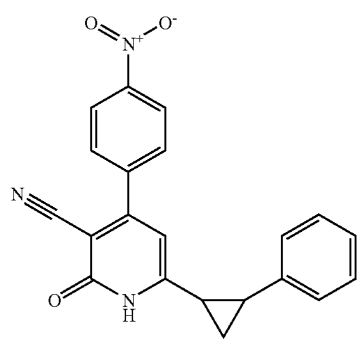 | 4-(4-Nitro-phenyl)-2-oxo-6-(2-phenyl-cyclopropyl)-1,2-dihydro-pyridine-3-carbonitrile | $^1$H-NMR (d$_6$-DMSO; 300 MHz): 12.84 (br. s, 1 H); 8.33 (d, 2 H); 7.51 (d, 2 H); 7.27 (m, 2 H); 7.22 (m, 3 H); 5.82 (s, 1 H); 2.82 (q, 1 H); 2.48 (q, 1 H); 2.00 (q, 1 H); 1.53 (q, 1 H). |
| 4.11 | 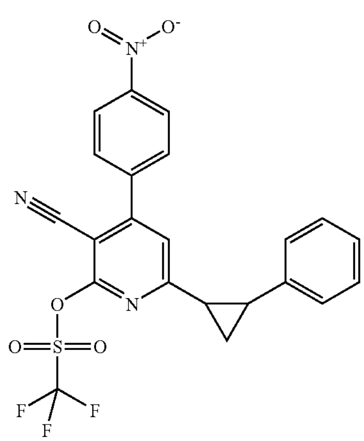 | Trifluoromethanesulfonic acid 3-cyano-4-(4-nitro-phenyl)-6-(2-phenyl-cyclopropyl)-pyridin-2-yl ester | $^1$H-NMR (d$_6$-DMSO; 400 MHz): 8.41 (d, 2 H); 7.82 (d, 2 H); 7.68 (s, 1 H); 7.17 (m, 5 H); 2.98 (q, 1 H); 2.90 (q, 1 H); 2.03 (q, 1 H); 1.71 (q, 1 H). |

| Inter-mediate | Structure | Name | Analytical data |
|---|---|---|---|
| 4.12 | 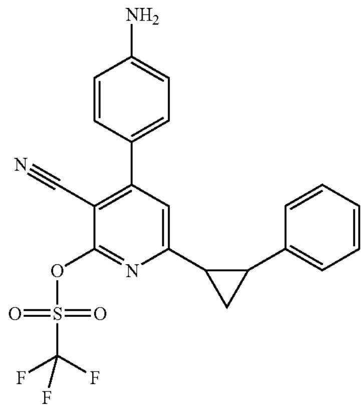 | Trifluoro-methanesulfonic acid 4-(4-amino-phenyl)-3-cyano-6-(2-phenyl-cyclopropyl)-pyridin-2-yl ester | $^1$H-NMR (d$_6$-DMSO; 300 MHz): 7.41 (s, 1 H); 7.31 (d, 2 H); 7.14 (m, 5 H); 6.66 (d, 2 H); 5.91 (br. s, 2 H); 2.88 (q, 1 H); 2.79 (q, 1 H); 1.96 (q, 1 H); 1.62 (q, 1 H). |
| 4.13 | 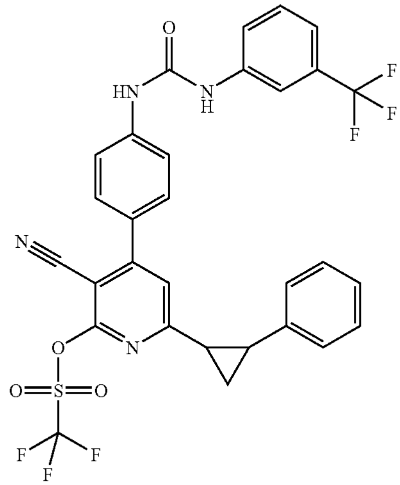 | Trifluoro-methanesulfonic acid 3-cyano-6-(2-phenyl-cyclopropyl)-4-{4-[3-(3-trifluoromethyl-phenyl)-ureido]-phenyl}-pyridin-2-yl ester | $^1$H-NMR (d$_6$-DMSO; 400 MHz): 9.20 (s, 1 H); 9.18 (s, 1 H); 8.03 (s, 1 H); 7.66 (d, 2 H); 7.60 (d, 1 H); 7.52 (m, 4 H); 7.34 (d, 1 H); 7.16 (m, 5 H); 2.94 (q, 1 H); 2.85 (q, 1 H); 2.01 (q, 1 H); 1.67 (q, 1 H). |
| 4.14 | 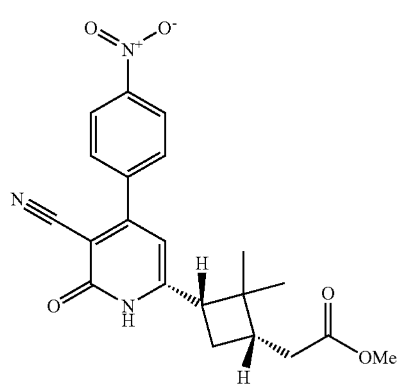 | {3-[5-Cyano-4-(4-nitro-phenyl)-6-oxo-1,6-dihydro-pyridin-2-yl]-2,2-dimethyl-cyclobutyl}-acetic acid methyl ester | $^1$H-NMR (d$_6$-DMSO; 300 MHz): 12.53 (br. s, 1 H); 8.39 (d, 2 H); 7.92 (d, 2 H); 6.42 (s, 1 H); 3.57 (s, 3 H); 3.14 (m, 1 H); 2.42 (m, 1 H); 2.35 (m, 2 H); 2.20 (m, 1 H); 2.08 (m, 1 H); 1.19 (s, 3 H); 0.76 (s, 3 H). |

| Intermediate | Structure | Name | Analytical data |
|---|---|---|---|
| 4.15 | 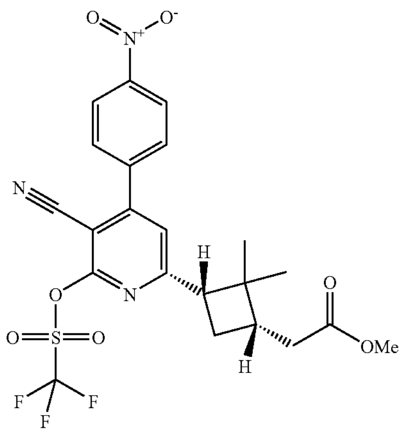 | {3-[5-Cyano-4-(4-nitro-phenyl)-6-trifluoromethane-sulfonyloxy-pyridin-2-yl]-2,2-dimethyl-cyclobutyl}-acetic acid methyl ester | $^1$H-NMR ($d_6$-DMSO; 300 MHz): 8.46 (d, 2 H); 8.06 (d, 2 H); 7.73 (s, 1 H); 3.59 (s, 3 H); 3.45 (m, 1 H); 2.55 (m, 1 H); 2.38 (m, 2 H); 2.24 (m, 2 H); 1.25 (s, 3 H); 0.64 (s, 3 H). |
| 4.16 | 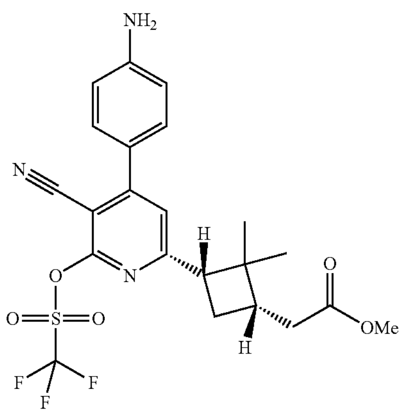 | {3-[4-(4-Amino-phenyl)-5-cyano-6-trifluoromethane-sulfonyloxy-pyridin-2-yl]-2,2-dimethyl-cyclobutyl}-acetic acid methyl ester | $^1$H-NMR ($d_6$-DMSO; 400 MHz): 7.55 (d, 2 H); 7.46 (s, 1 H); 6.71 (d, 2 H); 5.96 (br. s, 2 H); 3.58 (s, 3 H); 3.33 (m, 1 H); 2.54 (m, 1 H); 2.37 (m, 3 H); 2.19 (m, 1 H); 1.23 (s, 3 H); 0.62 (s, 3 H). |
| 4.17 | 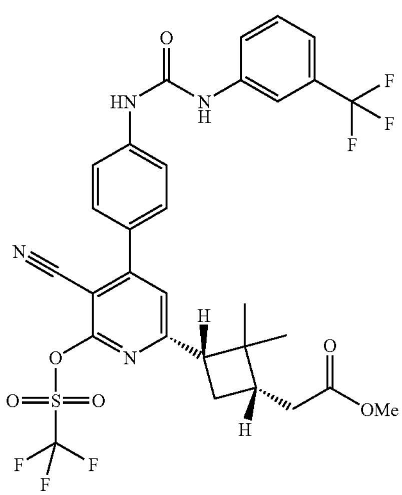 | [3-(5-Cyano-6-trifluoromethane-sulfonyloxy-4-{4-[3-(3-trifluoromethyl-phenyl)-ureido]-phenyl}-pyridin-2-yl)-2,2-dimethyl-cyclobutyl]-acetic acid methyl ester | $^1$H-NMR ($d_6$-DMSO; 400 MHz): 9.21 (s, 1 H); 9.20 (s, 1 H); 8.03 (s, 1 H); 7.76 (d, 2 H); 7.71 (d, 2 H); 7.61 (m, 2 H); 7.54 (m, 1 H); 7.34 (m, 1 H); 3.59 (s, 3 H); 3.41 (m, 1 H); 2.54 (m, 1 H); 2.38 (m, 3 H); 2.22 (m, 1 H); 1.25 (s, 3 H); 0.64 (s, 3 H). |

PREPARATION OF EXAMPLE COMPOUNDS

Example Compound 1.1

Preparation of 1-{3-Amino-1-methyl-4-[4-(3-phenyl-ureido)-phenyl]-1H-pyra-zolo[3,4-b]pyridin-6-yl}-cyclopropanecarboxylic acid ethyl ester

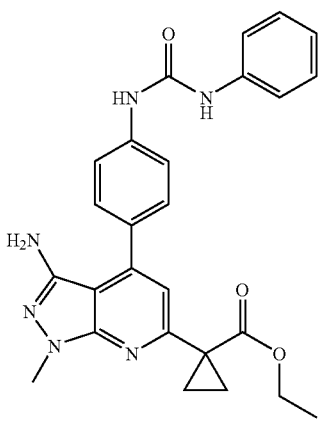

In analogy to GP 5, reaction of 420 mg Intermediate 1.4 (0.73 mmol) with 120 μl methyl hydrazine (2.2 mmol, 3 eq.) in 20 mL 1-PrOH yielded 219 mg of the pyrazolopyridine (0.46 mmol, 64% yield).

$^1$H-NMR (d$_6$-DMSO; 300 MHz): 8.94 (br. s, 1H); 8.77 (br. s, 1H); 7.65 (d, 2H); 7.55 (m, 2H); 7.47 (m, 2H); 7.30 (m, 2H); 7.03 (s, 1H); 6.99 (m, 1H); 4.68 (br. s, 2H); 4.10 (q, 2H); 3.78 (s, 3H); 1.54 (s, 4H); 1.14 (t, 3H).

Example Compound 1.2

Preparation of 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid ethyl ester

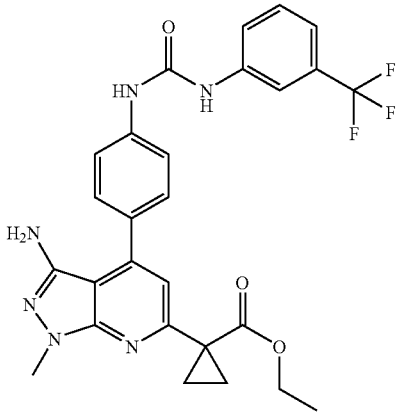

In analogy to GP 5, reaction of 3.78 g Intermediate 1.5 (5.9 mmol) with 940 μl methyl hydrazine (17.7 mmol, 3 eq.) in 150 mL 1-PrOH yielded 2.5 g of the pyrazolopyridine (4.7 mmol, 79% yield).

$^1$H-NMR (d$_6$-DMSO; 400 MHz): 9.14 (br. s, 1H); 9.07 (br. s, 1H); 8.04 (s, 1H); 7.68 (d, 2H); 7.60 (m, 1H); 7.54 (m, 3H); 7.33 (m, 1H); 7.04 (s, 1H); 4.68 (br. s, 2H); 4.10 (q, 2H); 3.78 (s, 3H); 1.54 (s, 4H); 1.14 (t, 3H).

Example Compound 1.3

Preparation of 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid

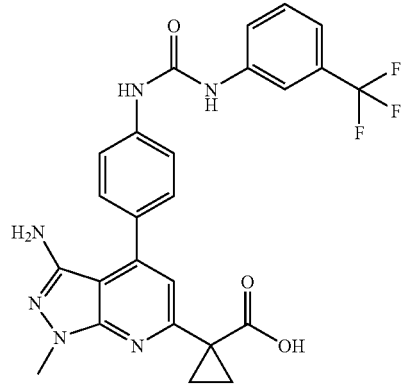

In analogy to GP 10, reaction of 0.96 g Example Compound 1.2 (1.78 mmol, 1 eq.) with 2.67 ml sodium hydroxide solution (2.67 mmol, 1.5 eq.) in 20 ml EtOH yielded 880 mg of the desired product (97% yield).

$^1$H-NMR (d$_6$-DMSO; 300 MHz): 12.61 (br. s, 1H); 9.15 (br. s, 1H); 9.07 (br. s, 1H); 8.04 (s, 1H); 7.68 (m, 2H); 7.60 (m, 1H); 7.55 (m, 3H); 7.33 (m, 1H); 7.05 (br. s, 1H); 4.65 (br. s, 2H); 3.79 (s, 3H); 1.53 (s, 2H); 1.50 (s, 2H).

Example Compound 1.4

Preparation of 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid methylamide

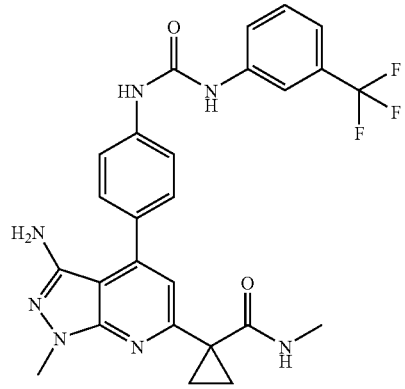

In analogy to GP 11, reaction of 234 mg Example Compound 1.3 (0.46 mmol, 1 eq.) with 0.23 ml methylamine (2M in THF; 0.46 mmol, 1 eq.), 0.25 ml 4-methylmorpholine (5 eq.) and 0.54 ml 2,4,6-tripropyl-[1,3,5,2,4,6]trioxa-triphosphinane 2,4,6-trioxide (T3P; 2 eq.) in 10 ml DCM yielded after purification with flash column chromatography 40 mg of the desired product (17% yield).

$^1$H-NMR (d$_6$-DMSO; 400 MHz): 9.18 (br. s, 1H); 9.10 (br. s, 1H); 8.05 (s, 1H); 7.67 (m, 2H); 7.60 (m, 1H); 7.53 (m, 3H); 7.45 (m, 1H); 7.33 (m, 1H); 6.86 (s, 1H); 4.68 (br. s, 2H); 3.80 (s, 3H); 2.59 (d, 3H); 1.37 (m, 2H); 1.28 (m, 2H).

MS (ESI): [M+H]$^+$=524.

Example Compound 1.5

Preparation of 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid ethylamide

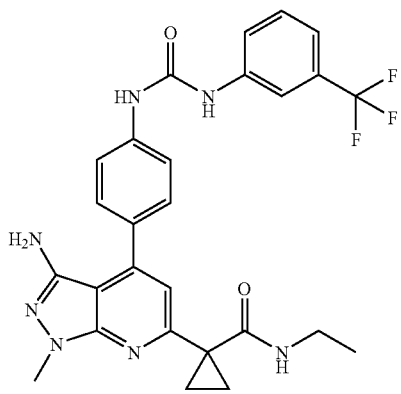

In analogy to GP 11, reaction of 430 mg Example Compound 1.3 (0.84 mmol, 1 eq.) with 0.7 ml ethylamine (2M in THF; 1.1 mmol, 1.3 eq.), 0.46 ml 4-methylmorpholine (5 eq.) and 1 ml 2,4,6-tripropyl-[1,3,5,2,4,6]trioxa-triphosphinane 2,4,6-trioxide (T3P; 2 eq.) in 25 ml DCM yielded 440 mg of the desired product (97% yield).

$^1$H-NMR (d$_6$-DMSO; 400 MHz): 9.23 (br. s, 1H); 9.15 (br. s, 1H); 8.05 (s, 1H); 7.74 (m, 1H); 7.67 (m, 2H); 7.61 (m, 1H); 7.53 (m, 3H); 7.33 (m, 1H); 6.84 (s, 1H); 4.67 (br. s, 2H); 3.79 (s, 3H); 3.11 (q, 2H); 1.37 (m, 2H); 1.31 (m, 2H); 1.00 (t, 3H).

Example Compound 1.6

Preparation of 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid isopropyl-amide

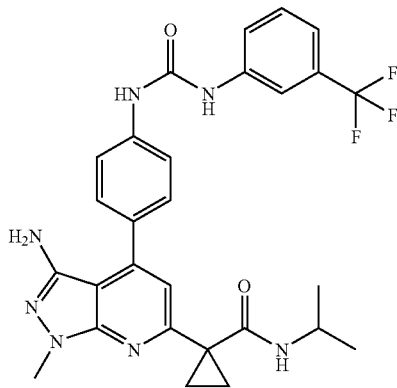

In analogy to GP 11, reaction of 205 mg Example Compound 1.3 (0.4 mmol, 1 eq.) with 0.07 ml isopropylamine (0.8 mmol, 2 eq.), 0.22 ml 4-methylmorpholine (5 eq.) and 0.47 ml 2,4,6-tripropyl-[1,3,5,2,4,6]trioxatriphosphinane 2,4,6-trioxide (T3P; 2 eq.) in 10 ml DCM yielded after purification with flash column chromatography 110 mg of the desired product (50% yield).

$^1$H-NMR (d$_6$-DMSO; 300 MHz): 9.16 (br. s, 1H); 9.07 (br. s, 1H); 8.04 (s, 1H); 7.89 (d, 1H); 7.66 (m, 2H); 7.60 (m, 1H); 7.53 (m, 3H); 7.32 (d, 1H); 6.80 (s, 1H); 4.67 (br. s, 2H); 3.96 (sept, 1H); 3.79 (s, 3H); 1.38 (m, 2H); 1.35 (m, 2H); 1.08 (d, 6H).

MS (ESI): [M+H]$^+$=552 (100%).

Example Compound 1.7

Preparation of 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid phenylamide

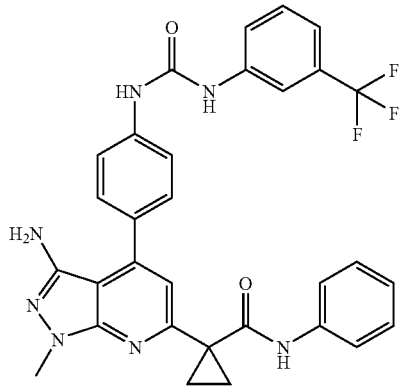

In analogy to GP 11, reaction of 202 mg Example Compound 1.3 (0.4 mmol, 1 eq.) with 36.85 mg aniline (0.4 mmol, 1 eq.), 0.22 ml 4-methylmorpholine (5 eq.) and 0.47 ml 2,4,6-tripropyl-[1,3,5,2,4,6]trioxatriphosphinane 2,4,6-trioxide (T3P; 2 eq.) in 9 ml DCM yielded after purification with flash column chromatography 123 mg of the desired product (53% yield).

$^1$H-NMR (d$_6$-DMSO; 300 MHz): 10.12 (s, 1H); 9.16 (br. s, 1H); 9.07 (br. s, 1H); 8.03 (s, 1H); 7.62 (m, 5H); 7.53 (m, 3H); 7.30 (m, 3H); 7.05 (m, 1H); 6.84 (s, 1H); 4.69 (br. s, 2H); 3.82 (s, 3H); 1.55 (m, 2H); 1.52 (m, 2H).

MS (ESI): [M+H]$^+$=586 (100%).

The following Example Compounds 1.8 to 1.15 were prepared in analogy to GP11 and the before mentioned Intermediates 1.4 to 1.7 by reacting Example Compound 1.3 with the respective amines:

| Example | Structure | Name | Analytical data |
|---|---|---|---|
| 1.8 | 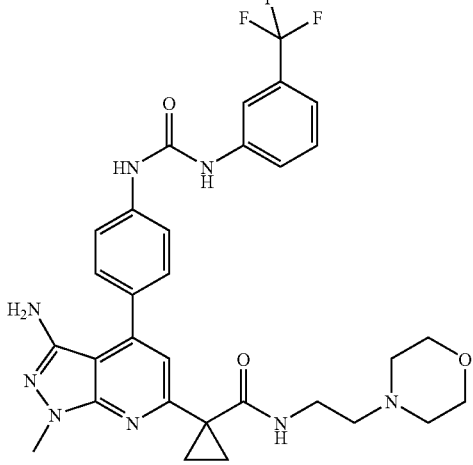 | 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid (2-morpholin-4-yl-ethyl)-amide | $^1$H-NMR (d$_6$-DMSO; 400 MHz): 9.18 (br. s, 1 H); 9.11 (br. s, 1 H); 8.04 (br. s, 1 H); 7.67 (d, 2 H); 7.60 (d, 1 H); 7.54 (m, 4 H); 7.33 (d, 1 H); 6.89 (s, 1 H); 4.69 (br. s, 2 H); 3.81 (s, 3 H); 3.37 (m, 4 H); 3.19 (q, 2 H); 2.33 (t, 2 H); 2.27 (br. s, 4 H); 1.39 (m, 2 H); 1.32 (m, 2 H) <br> MS (ESI): [M + H]$^+$ = 623 (100%) |
| 1.9 | 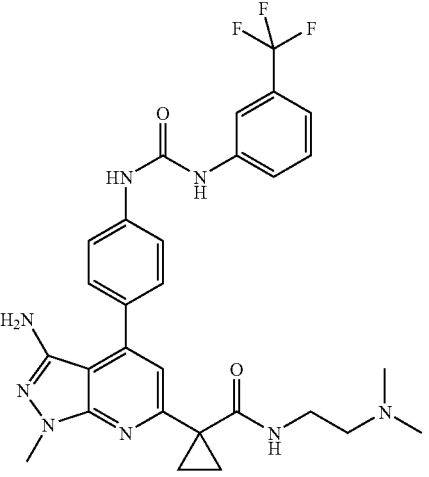 | 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid (2-dimethylamino-ethyl)-amide | $^1$H-NMR (d$_6$-DMSO; 400 MHz): 9.16 (br. s, 1 H); 9.09 (br. s, 1 H); 8.04 (br. s, 1 H); 7.99 (m, 1 H); 7.67 (d, 2 H); 7.60 (d, 1 H); 7.54 (m, 3 H); 7.33 (d, 1 H); 6.86 (s, 1 H); 4.69 (br. s, 2 H); 3.82 (s, 3 H); 3.20 (m, 2 H); 2.29 (m, 2 H); 2.09 (s, 6 H); 1.41 (m, 2 H); 1.34 (m, 2 H) <br> MS (ESI): [M + H]$^+$ = 581 (100%) |
| 1.10 | 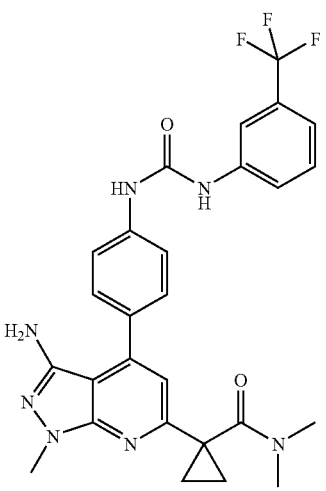 | 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid dimethylamide | $^1$H-NMR (d$_6$-DMSO; 400 MHz): 9.16 (br. s, 1 H); 9.09 (br. s, 1 H); 8.04 (s, 1 H); 7.66 (d, 2 H); 7.60 (d, 1 H); 7.53 (t, 1 H); 7.51 (d, 2 H); 7.33 (d, 1 H); 6.58 (s, 1 H); 4.67 (br. s, 2 H); 3.76 (s, 3 H); 2.91 (s, 3 H); 2.86 (s, 3 H); 1.54 (m, 2 H); 1.34 (m, 2 H) <br> MS (ESI): [M + H]$^+$ = 538 (100%) |

| Example | Structure | Name | Analytical data |
|---|---|---|---|
| 1.11 | 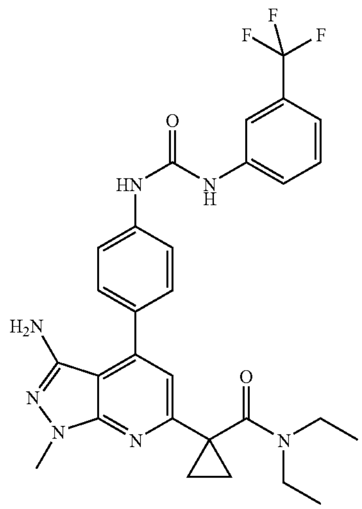 | 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid diethylamide | $^1$H-NMR (d$_6$-DMSO; 400 MHz): 9.15 (br. s, 1 H); 9.07 (br. s, 1 H); 8.04 (s, 1 H); 7.66 (d, 2 H); 7.60 (d, 1 H); 7.53 (t, 1 H); 7.49 (d, 2 H); 7.33 (d, 1 H); 6.62 (s, 1 H); 4.67 (br. s, 2 H); 3.76 (s, 3 H); 3.33 (q, 2 H); 3.30 (q, 2 H); 1.52 (m, 2 H); 1.33 (m, 2 H); 1.09 (t, 3 H); 0.86 (t, 3 H) MS (ESI): [M + H]$^+$ = 566 (100%) |
| 1.12 | 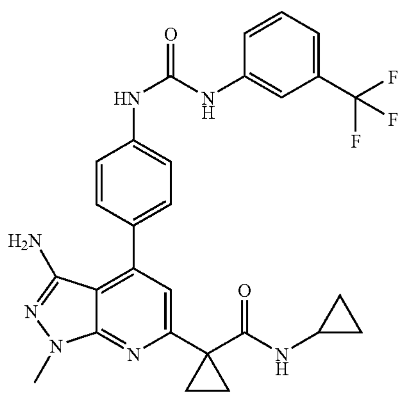 | 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid cyclopropylamide | $^1$H-NMR (d$_6$-DMSO; 300 MHz): 9.15 (br. s, 1 H); 9.07 (br. s, 1 H); 8.04 (s, 1 H); 7.91 (d, 1 H); 7.67 (d, 2 H); 7.61 (d, 1 H); 7.53 (t, 1 H); 7.52 (d, 2 H); 7.33 (d, 1 H); 6.78 (s, 1 H); 4.66 (br. s, 2 H); 3.78 (s, 3 H); 2.69 (m, 1 H); 1.37 (m, 2 H); 1.34 (m, 2 H); 0.59 (m, 2 H); 0.43 (m, 2 H). MS (ESI): [M + H]$^+$ = 550 (100%). |
| 1.13 | 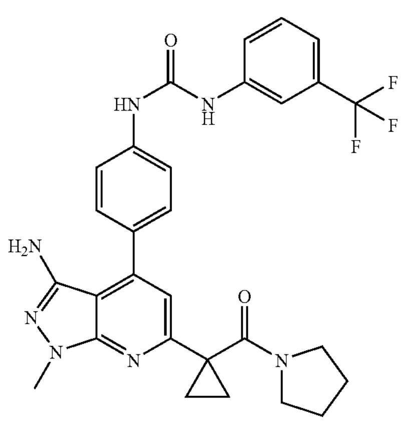 | 1-(4-{3-Amino-1-methyl-6-[1-(pyrrolidine-1-carbonyl)-cyclopropyl]-1H-pyrazolo[3,4-b]pyridin-4-yl}-phenyl)-3-(3-trifluoromethyl-phenyl)-urea | $^1$H-NMR (d$_6$-DMSO; 300 MHz): 9.18 (br. s, 1 H); 9.10 (br. s, 1 H); 8.04 (s, 1 H); 7.67 (d, 2 H); 7.61 (d, 1 H); 7.53 (t, 1 H); 7.50 (d, 2 H); 7.33 (m, 1 H); 6.63 (s, 1 H); 4.66 (br. s, 2 H); 3.76 (s, 3 H); 3.40 (m, 2 H); 3.19 (m, 2 H); 1.74 (m, 4 H); 1.50 (m, 2 H); 1.35 (m, 2 H). MS (ESI): [M + H]$^+$ = 564 (100%). |

-continued

| Example | Structure | Name | Analytical data |
|---|---|---|---|
| 1.14 | 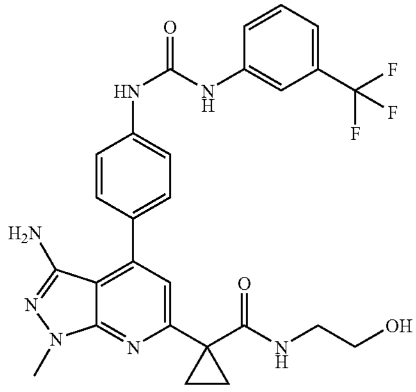 | 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid (2-hydroxy-ethyl)-amide | $^1$H-NMR ($d_6$-DMSO; 400 MHz): 9.35 (br. s, 1 H); 9.27 (br. s, 1 H); 8.05 (br. s, 1 H); 7.97 (t, 1 H); 7.68 (d, 2 H); 7.63 (d, 1 H); 7.54 (d, 2 H); 7.52 (t, 1 H); 7.32 (d, 1 H); 6.84 (s, 1 H); 4.69 (br. s, 2 H); 3.81 (s, 3 H); 3.42 (t, 2 H); 3.19 (t, 1 H); 3.18 (t, 1 H); 1.42 (m, 2 H); 1.33 (m, 2 H). MS (ESI): $[M + H]^+$ = 554 (100%). |
| 1.15 | 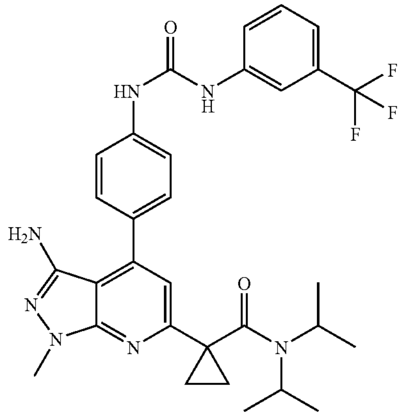 | 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid diisopropylamide | $^1$H-NMR ($d_6$-DMSO; 300 MHz): 9.17 (br. s, 1 H); 9.06 (br. s, 1 H); 8.04 (s, 1 H); 7.66 (d, 2 H); 7.60 (d, 1 H); 7.53 (t, 1 H); 7.48 (d, 2 H); 7.33 (d, 1 H); 6.66 (s, 1 H); 4.66 (br. s, 2 H); 4.26 (m, 1 H); 3.77 (s, 3 H); 3.40 (m, 1 H); 1.48 (m, 2 H); 1.38 (d, 6 H); 1.33 (m, 2 H); 0.89 (d, 6 H) MS (ESI): $[M + H]^+$ = 594 (100%) |

Example Compound 2.1

Preparation of 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid amide

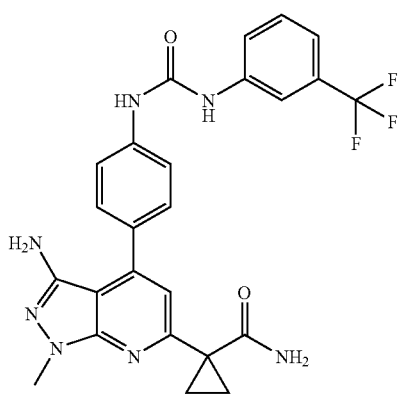

In analogy to *Synth. Comm.* 1990, 20, 1203, reaction of 148 mg Example Compound 1.2 (0.27 mmol, 1.4 eq.) with 0.39 ml sodium methoxide solution (0.5 M in MeOH, 0.2 mmol, 1 eq.) and 42.44 mg formamide (0.94 mmol, 4.8 eq.) in 2 ml DMF yielded after purification with preparative HPLC 21 mg of the desired product (15% yield).

$^1$H-NMR ($d_6$-DMSO; 300 MHz): 9.16 (br. s, 1H); 9.08 (br. s, 1H); 8.04 (s, 1H); 7.67 (m, 2H); 7.60 (m, 1H); 7.54 (m, 3H); 7.33 (m, 1H); 7.11 (br. s, 2H); 6.89 (s, 1H); 4.66 (br. s, 2H); 3.79 (s, 3H); 1.39 (m, 2H); 1.31 (m, 2H).

Example Compound 3.1

Preparation of 1-1-(3-Amino-1-methyl-4-{3-[3-(3-trifluoromethyl-phenyl)-ureido]-phenyl}-1H-pyrazolo[3,4-b]pyridin-6-yl)-cyclopropanecarboxylic acid ethyl ester

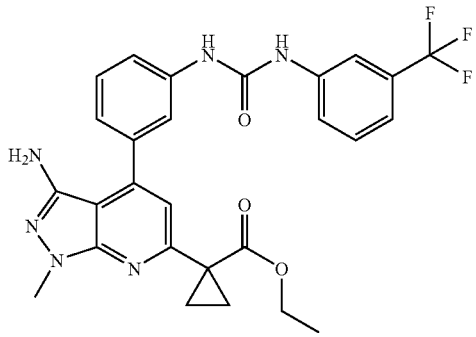

In analogy to GP 5, reaction of 1.7 g Intermediate 2.4 (2.65 mmol) with 420 µl methyl hydrazine (7.94 mmol, 3 eq.) in 75 mL 1-PrOH yielded 1.3 g of the pyrazolopyridine (91% yield).

$^1$H-NMR (d$_6$-DMSO; 400 MHz): 9.15 (s, 1H); 9.06 (s, 1H); 8.02 (s, 1H); 7.75 (s, 1H); 7.59 (d, 1H); 7.53 (m, 2H); 7.49 (t, 1H); 7.32 (d, 1H); 7.21 (d, 1H); 7.07 (s, 1H); 4.78 (br. s, 2H); 4.11 (q, 2H); 3.79 (s, 3H); 1.56 (s, 4H); 1.16 (t, 3H).

MS (ESI): [M+H]$^+$=539.

Example Compound 3.2

Preparation of 1-(3-Amino-1-methyl-4-{3-[3-(3-trifluoromethyl-phenyl)-ureido]-phenyl}-1H-pyrazolo[3,4-b]pyridin-6-yl)-cyclopropanecarboxylic acid

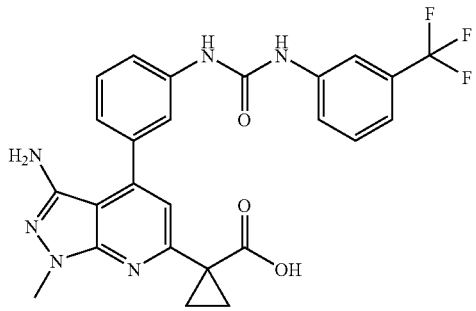

In analogy to GP 10, reaction of 1.3 g Example Compound 3.1 (2.41 mmol, 1 eq.) with 3.62 ml sodium hydroxide solution (3.62 mmol, 1.5 eq.) in 26 ml EtOH yielded the desired product (61% yield).

$^1$H-NMR (d$_6$-DMSO; 300 MHz): 12.60 (br. s, 1H); 9.13 (s, 1H); 9.05 (s, 1H); 8.00 (s, 1H); 7.71 (s, 1H); 7.61 (d, 1H); 7.55 (m, 2H); 7.49 (t, 1H); 7.32 (d, 1H); 7.21 (d, 1H); 7.08 (s, 1H); 4.76 (br. s, 2H); 3.80 (s, 3H); 1.54 (s, 2H); 1.52 (s, 2H).

MS (ESI): [M+H]$^+$=511.

Example Compound 3.3

Preparation of 1-(3-Amino-1-methyl-4-{3-[3-(3-trifluoromethyl-phenyl)-ureido]-phenyl}-1H-pyrazolo[3,4-b]pyridin-6-yl)-cyclopropanecarboxylic acid methylamide

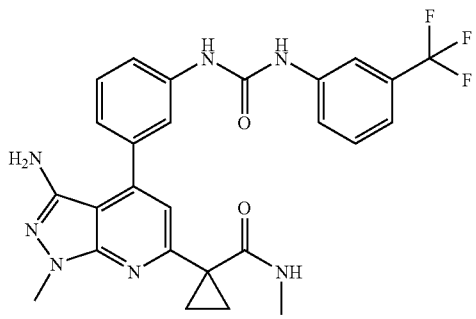

In analogy to GP 11, reaction of 200 mg Example Compound 3.2 (0.39 mmol, 1 eq.) with 0.29 ml methylamine (0.59 mmol, 1.5 eq.), 0.22 ml 4-methylmorpholine (5 eq.) and 0.46 ml 2,4,6-tripropyl-[1,3,5,2,4,6]trioxatriphosphinane 2,4,6-trioxide (T3P; 2 eq.) in 10 ml DCM yielded 200 mg of the desired product (97% yield).

$^1$H-NMR (d$_6$-DMSO; 400 MHz): 9.14 (s, 1H); 9.06 (s, 1H); 8.01 (s, 1H); 7.72 (s, 1H); 7.60 (d, 1H); 7.55 (d, 1H); 7.52 (t, 1H); 7.50 (d, 1H); 7.48 (d, 1H); 7.32 (d, 1H); 7.20 (d, 1H); 6.88 (s, 1H); 4.78 (br. s, 2H); 3.80 (s, 3H); 2.58 (d, 3H); 1.38 (m, 2H); 1.29 (m, 2H).

MS (ESI): [M+H]$^+$=524.

Example Compound 3.4

Preparation of 1-(3-Amino-1-methyl-4-{3-[3-(3-trifluoromethyl-phenyl)-ureido]-phenyl}-1H-pyrazolo[3,4-b]pyridin-6-yl)-cyclopropanecarboxylic acid dimethylamide

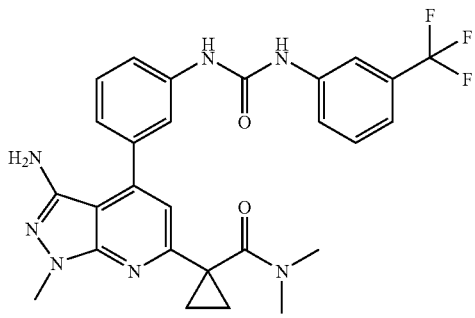

In analogy to GP 11, reaction of 200 mg Example Compound 3.2 (0.39 mmol, 1 eq.) with 0.29 ml dimethylamine (0.59 mmol, 1.5 eq.), 0.22 ml 4-methylmorpholine (5 eq.) and 0.46 ml 2,4,6-tripropyl-[1,3,5,2,4,6]trioxatriphosphinane 2,4,6-trioxide (T3P; 2 eq.) in 20 ml DCM yielded 165 mg of the desired product (78% yield).

$^1$H-NMR (d$_6$-DMSO; 400 MHz): 9.16 (s, 1H); 9.07 (s, 1H); 8.02 (s, 1H); 7.73 (s, 1H); 7.59 (d, 1H); 7.52 (m, 2H); 7.49 (t, 1H); 7.32 (d, 1H); 7.19 (d, 1H); 6.62 (s, 1H); 4.77 (br. s, 2H); 3.77 (s, 3H); 2.92 (s, 3H); 2.87 (s, 3H); 1.55 (m, 2H); 1.35 (m, 2H).

MS (ESI): [M+H]$^+$=538.

Example Compound 3.5

Preparation of 1-(3-Amino-1-methyl-4-{3-[3-(3-trifluoromethyl-phenyl)-ureido]-phenyl}-1H-pyrazolo[3,4-b]pyridin-6-yl)-cyclopropanecarboxylic acid cyclopropylamide

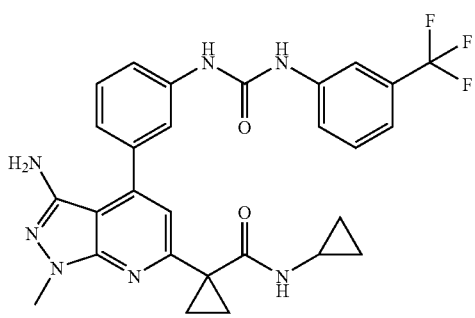

In analogy to GP 11, reaction of 250 mg Example Compound 3.2 (0.49 mmol, 1 eq.) with 37 mg cyclopropylamine (0.65 mmol, 1.33 eq.), 0.27 ml 4-methylmorpholine (5 eq.) and 0.58 ml 2,4,6-tripropyl-[1,3,5,2,4,6]trioxa-triphosphinane 2,4,6-trioxide (T3P; 2 eq.) in 15 ml DCM yielded 197 mg of the desired product (73% yield).

¹H-NMR (d₆-DMSO; 400 MHz): 9.15 (s, 1H); 9.06 (s, 1H); 8.02 (s, 1H); 7.90 (d, 1H); 7.75 (s, 1H); 7.59 (d, 1H); 7.50 (m, 2H); 7.48 (t, 1H); 7.31 (d, 1H); 7.17 (d, 1H); 6.81 (s, 1H); 4.75 (br. s, 2H); 3.78 (s, 3H); 2.69 (m, 1H); 1.37 (m, 2H); 1.34 (m, 2H); 0.57 (m, 2H); 0.45 (m, 2H).

Example Compound 4.1

Preparation of 1-(3-Amino-4-{4-[3-(2-fluoro-5-methyl-phenyl)-ureido]-phenyl}-1-methyl-1H-pyrazolo [3,4-b]pyridin-6-yl)-cyclopropanecarboxylic acid ethyl ester

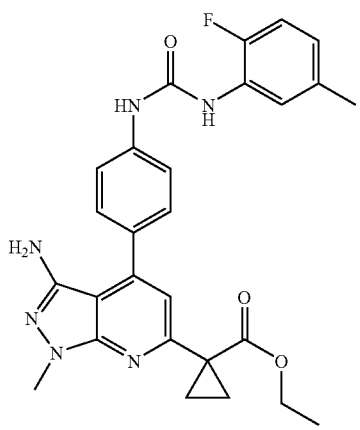

In analogy to GP 5, reaction of 1 g Intermediate 3.1 (1.65 mmol) with 0.26 ml methyl hydrazine (4.95 mmol, 3 eq.) in 50 mL 1-PrOH yielded 0.7 g of the pyrazolopyridine (84% yield).

¹H-NMR (d₆-DMSO; 400 MHz): 9.30 (s, 1H); 8.57 (m, 1H); 8.00 (dd, 1H); 7.65 (d, 2H); 7.55 (d, 2H); 7.12 (dd, 1H); 7.04 (s, 1H); 6.82 (m, 1H); 4.68 (br. s, 2H); 4.10 (q, 2H); 3.78 (s, 3H); 2.28 (s, 3H); 1.54 (s, 4H); 1.14 (t, 3H).

Example Compound 4.2

Preparation of 1-(3-Amino-4-{4-[3-(2-fluoro-5-methyl-phenyl)-ureido]-phenyl}-1-methyl-1H-pyrazolo [3,4-b]pyridin-6-yl)-cyclopropanecarboxylic acid

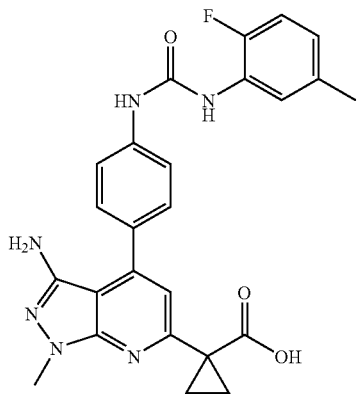

In analogy to GP 10, reaction of 0.7 g Example Compound 4.1 (1.39 mmol, 1 eq.) with 2.09 ml sodium hydroxide solution (2.09 mmol, 1.5 eq.) in 15 ml EtOH yielded 600 mg of the desired product (91% yield).

Example Compound 4.3

Preparation of 1-(4-[3-Amino-1-methyl-6-[1-(pyrrolidine-1-carbonyl)-cyclopropyl]-1H-pyrazolo[3,4-b] pyridin-4-yl-phenyl)-3-(2-fluoro-5-methyl-phenyl)-urea

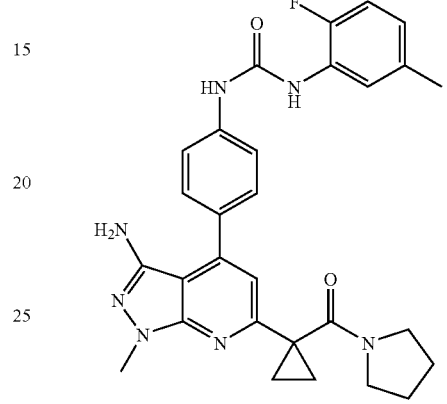

In analogy to GP 11, reaction of 200 mg Example Compound 4.2 (0.42 mmol, 1 eq.) with 0.052 ml pyrrolidine (0.63 mmol, 1.5 eq.), 0.23 ml 4-methylmorpholine (5 eq.) and 0.5 ml 2,4,6-tripropyl-[1,3,5,2,4,6]trioxatriphosphinane 2,4,6-trioxide (T3P; 2 eq.) in 15 ml DCM yielded 125 mg of the desired product (56% yield).

¹H-NMR (d₆-DMSO; 400 MHz): 9.31 (s, 1H); 8.57 (m, 1H); 8.00 (dd, 1H); 7.65 (d, 2H); 7.50 (d, 2H); 7.12 (dd, 1H); 6.82 (m, 1H); 6.62 (s, 1H); 4.66 (br. s, 2H); 3.76 (s, 3H); 3.39 (m, 2H); 3.18 (m, 2H); 2.28 (s, 3H); 1.74 (m, 4H); 1.49 (m, 2H); 1.35 (m, 2H).

Example Compound 4.4

Preparation of 1-(3-Amino-4-{4-[3-(2-fluoro-5-methyl-phenyl)-ureido]-phenyl}-1-methyl-1H-pyrazolo [3,4-b]pyridin-6-yl)-cyclopropanecarboxylic acid dimethylamide

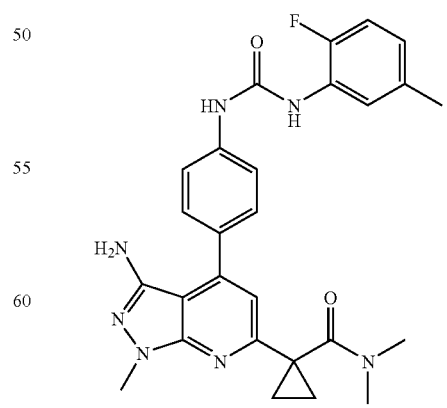

In analogy to GP 11, reaction of 200 mg Example Compound 4.2 (0.42 mmol, 1 eq.) with 0.32 ml dimethylamine (0.63 mmol, 1.5 eq.), 0.23 ml 4-methylmorpholine (5 eq.) and 0.5 ml 2,4,6-tripropyl-[1,3,5,2,4,6]trioxatriphosphinane 2,4,6-trioxide (T3P; 2 eq.) in 15 ml DCM yielded 136 mg of the desired product (64% yield).

$^1$H-NMR (d$_6$-DMSO; 300 MHz): 9.31 (s, 1H); 8.57 (m, 1H); 8.00 (dd, 1H); 7.65 (d, 2H); 7.51 (d, 2H); 7.12 (dd, 1H); 6.82 (m, 1H); 6.58 (s, 1H); 4.67 (br. s, 2H); 3.76 (s, 3H); 2.91 (s, 3H); 2.86 (s, 3H); 2.28 (s, 3H); 1.54 (m, 2H); 1.34 (m, 2H).

Example Compound 4.5

Preparation of 1-(3-Amino-4-{4-[3-(2-fluoro-5-methyl-phenyl)-ureido]-phenyl}-1-methyl-1H-pyrazolo[3,4-b]pyridin-6-yl)-cyclopropanecarboxylic acid cyclopropylamide

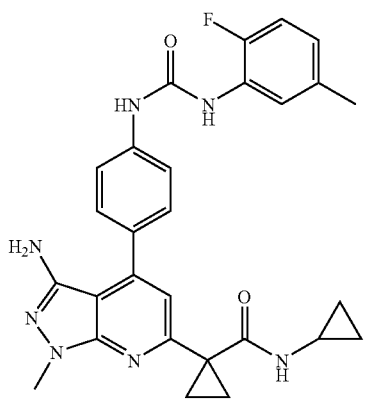

In analogy to GP 11, reaction of 200 mg Example Compound 4.2 (0.42 mmol, 1 eq.) with 36.1 mg cyclopropylamine (0.63 mmol, 1.5 eq.), 0.23 ml 4-methylmorpholine (5 eq.) and 0.5 ml 2,4,6-tripropyl-[1,3,5,2,4,6]trioxa-triphosphinane 2,4,6-trioxide (T3P; 2 eq.) in 15 ml DCM yielded 178 mg of the desired product (82% yield).

$^1$H-NMR (d$_6$-DMSO; 300 MHz): 9.31 (s, 1H); 8.58 (m, 1H); 8.00 (dd, 1H); 7.91 (d, 1H); 7.65 (d, 2H); 7.51 (d, 2H); 7.12 (dd, 1H); 6.82 (m, 1H); 6.78 (s, 1H); 4.67 (br. s, 2H); 3.78 (s, 3H); 2.70 (m, 1H); 2.28 (s, 3H); 1.37 (m, 2H); 1.33 (m, 2H); 0.59 (m, 2H); 0.43 (m, 2H).

Example Compound 5.1

Preparation of 1-[4-(3-Amino-6-cyclopropyl-1-methyl-1H-pyrazolo[3,4-b]pyridin-4-yl)-phenyl]-3-(3-trifluoromethyl-phenyl)-urea

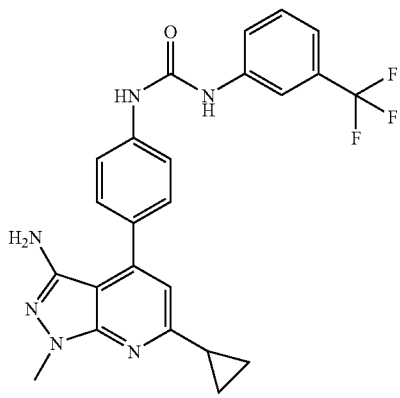

In analogy to GP 5, reaction of 1.42 g Intermediate 4.1 (2.49 mmol) with 0.4 mL methyl hydrazine (7.47 mmol, 3 eq.) in 90 mL 1-PrOH yielded 1.1 g of the pyrazolopyridine (95% yield).

$^1$H-NMR (d$_6$-DMSO; 300 MHz): 9.15 (s, 1H); 9.05 (s, 1H); 8.04 (s, 1H); 7.66 (d, 2H); 7.61 (d, 1H); 7.54 (d, 2H); 7.53 (t, 1H); 7.33 (d, 1H); 6.83 (s, 1H); 4.58 (br. s, 2H); 3.73 (s, 3H); 2.21 (m, 1H); 1.02 (m, 4H).

Example Compound 6.1

Preparation of 1-[4-(3-Amino-6-cyclobutyl-1-methyl-1H-pyrazolo[3,4-b]pyridin-4-yl)-phenyl]-3-(3-trifluoromethyl-phenyl)-urea

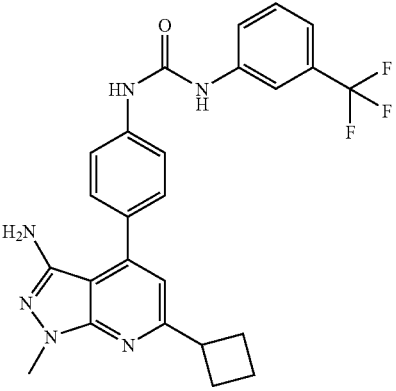

In analogy to GP 5, reaction of 755 mg Intermediate 4.5 (1.29 mmol) with 0.21 mL methyl hydrazine (3.88 mmol, 3 eq.) in 41 mL 1-PrOH yielded 490 mg of the pyrazolopyridine (79% yield).

$^1$H-NMR (d$_6$-DMSO; 400 MHz): 9.14 (s, 1H); 9.05 (s, 1H); 8.04 (s, 1H); 7.66 (d, 2H); 7.60 (d, 1H); 7.53 (d, 2H); 7.53 (t, 1H); 7.33 (d, 1H); 6.78 (s, 1H); 4.62 (br. s, 2H); 3.81 (s, 3H); 3.74 (m, 1H); 2.38 (m, 2H); 2.31 (m, 2H); 2.02 (m, 1H); 1.87 (m, 1H).

Example Compound 7.1

Preparation of 1-[4-(3-Amino-6-cyclohexyl-1-methyl-1H-pyrazolo[3,4-b]pyridin-4-yl)-phenyl]-3-(3-trifluoromethyl-phenyl)-urea

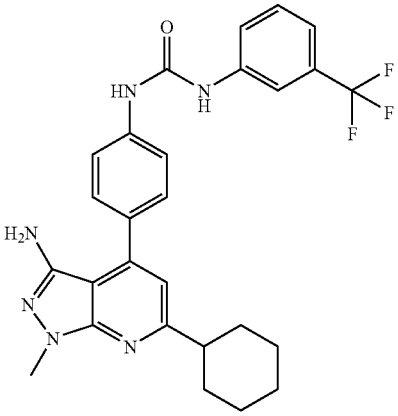

In analogy to GP 5, reaction of 2.04 g Intermediate 4.9 (3.33 mmol) with 0.53 mL methyl hydrazine (9.99 mmol, 3 eq.) in 105 mL 1-PrOH yielded 1.38 g of the pyrazolopyridine (81% yield).

$^1$H-NMR (d$_6$-DMSO; 400 MHz): 9.13 (s, 1H); 9.05 (s, 1H); 8.04 (s, 1H); 7.66 (d, 2H); 7.60 (d, 1H); 7.54 (d, 2H); 7.53 (t, 1H); 7.33 (d, 1H); 6.80 (s, 1H); 4.61 (br. s, 2H); 3.79 (s, 3H); 2.77 (m, 1H); 1.91 (m, 2H); 1.82 (m, 2H); 1.72 (m, 1H); 1.61 (m, 2H); 1.39 (m, 2H); 1.27 (m, 1H).

Example Compound 8.1

Preparation of 1-{4-[3-Amino-1-methyl-6-(2-phenyl-cyclopropyl)-1H-pyrazolo[3,4-b]pyridin-4-yl]-phenyl}-3-(3-trifluoromethyl-phenyl)-urea

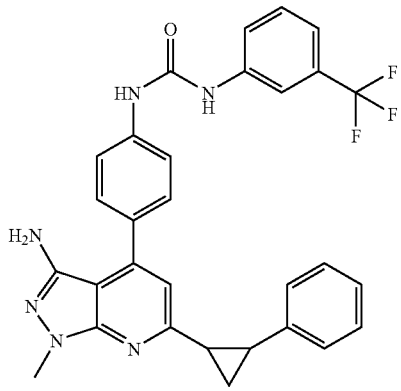

In analogy to GP 5, reaction of 659 mg Intermediate 4.13 (1.02 mmol) with 0.16 mL methyl hydrazine (3.06 mmol, 3 eq.) in 32 mL 1-PrOH yielded 415 mg of the pyrazolopyridine (75% yield).

$^1$H-NMR (d$_6$-DMSO; 400 MHz): 9.13 (s, 1H); 9.02 (s, 1H); 8.04 (s, 1H); 7.60 (d, 3H); 7.53 (t, 1H); 7.33 (d, 3H); 7.22 (d, 2H); 7.13 (t, 2H); 7.05 (t, 1H); 6.59 (s, 1H); 4.52 (br. s, 2H); 3.66 (s, 3H); 2.73 (m, 2H); 2.01 (m, 1H); 1.51 (m, 1H).

Example Compound 8.2

Preparation of [3-(3-Amino-1-methyl-4-{4-[3-(3-trifluoromethyl-phenyl)-ureido]-phenyl}-1H-pyrazolo[3,4-b]pyridin-6-yl)-2,2-dimethyl-cyclobutyl]-acetic acid methyl ester

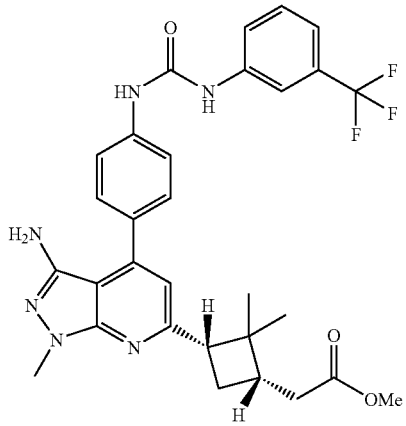

In analogy to GP 5, reaction of 1.85 g Intermediate 4.17 (2.7 mmol) with 0.44 ml methyl hydrazine (8.28 mmol, 3.06 eq.) in 100 mL 1-PrOH yielded 1.13 g of the pyrazolopyridine (72% yield).

$^1$H-NMR (d$_6$-DMSO; 300 MHz): 9.13 (s, 1H); 9.05 (s, 1H); 8.04 (s, 1H); 7.66 (d, 2H); 7.61 (m, 1H); 7.54 (d, 2H); 7.53 (m, 1H); 7.33 (m, 1H); 6.64 (s, 1H); 4.62 (br. s, 2H); 3.81 (s, 3H); 3.59 (s, 3H); 3.44 (m, 1H); 2.54 (m, 1H); 2.38 (m, 3H); 2.19 (m, 1H); 1.27 (s, 3H); 0.62 (s, 3H).

Example Compound 8.3

Preparation of [3-(3-Amino-1-methyl-4-{4-[3-(3-trifluoromethyl-phenyl)-ureido]-phenyl}-1H-pyrazolo[3,4-b]pyridin-6-yl)-2,2-dimethyl-cyclobutyl]-acetic acid

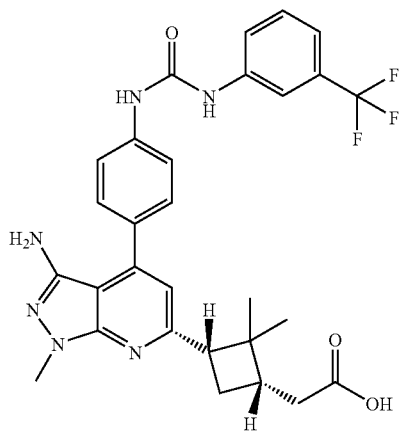

In analogy to GP 10, reaction of 407 mg Example Compound 8.2 (0.7 mmol, 1 eq.) with 1.05 ml sodium hydroxide solution (1.05 mmol, 1.5 eq.) in 17 ml EtOH yielded 384 mg of the desired product (97% yield).

$^1$H-NMR (d$_6$-DMSO; 300 MHz): 12.01 (br. s, 1H); 9.12 (s, 1H); 9.05 (s, 1H); 8.04 (s, 1H); 7.66 (d, 2H); 7.61 (m, 1H); 7.54 (d, 2H); 7.53 (m, 1H); 7.33 (m, 1H); 6.64 (s, 1H); 4.62 (br. s, 2H); 3.81 (s, 3H); 3.41 (m, 1H); 2.47-2.12 (m, 5H); 1.28 (s, 3H); 0.62 (s, 3H).

Example Compound 8.4

Preparation of 2-[3-(3-Amino-1-methyl-4-{4-[3-(3-trifluoromethyl-phenyl)-ureido]-phenyl}-1H-pyrazolo[3,4-b]pyridin-6-yl)-2,2-dimethyl-cyclobutyl]-N,N-dimethyl-acetamide

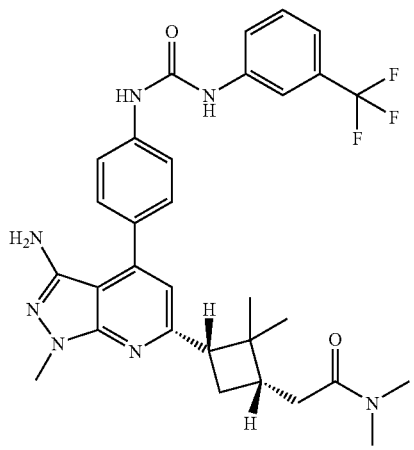

In analogy to GP 11, reaction of 369 mg Example Compound 8.3 (0.65 mmol, 1 eq.) with 0.49 ml dimethylamine (0.98 mmol, 1.5 eq.), 0.36 ml 4-methylmorpholine (5 eq.) and 0.77 ml 2,4,6-tripropyl-[1,3,5,2,4,6]trioxatriphosphinane 2,4,6-trioxide (T3P; 2 eq.) in 16.28 ml DCM yielded 181 mg of the desired product (31% yield).

$^1$H-NMR (d$_6$-DMSO; 300 MHz): 9.14 (s, 1H); 9.06 (s, 1H); 8.04 (s, 1H); 7.66 (d, 2H); 7.61 (m, 1H); 7.54 (d, 2H); 7.52 (m, 1H); 7.33 (m, 1H); 6.63 (s, 1H); 4.62 (br. s, 2H); 3.81 (s, 3H); 3.44 (m, 1H); 2.98 (s, 3H); 2.81 (s, 3H); 2.44 (m, 1H); 2.33 (m, 3H); 2.16 (m, 1H); 1.28 (s, 3H); 0.62 (s, 3H).

Example Compound 8.5

Preparation of 2-[3-(3-Amino-1-methyl-4-{4-[3-(3-trifluoromethyl-phenyl)-ureido]-phenyl}-1H-pyrazolo[3,4-b]pyridin-6-yl)-2,2-dimethyl-cyclobutyl]-N-cyclopropyl-acetamide

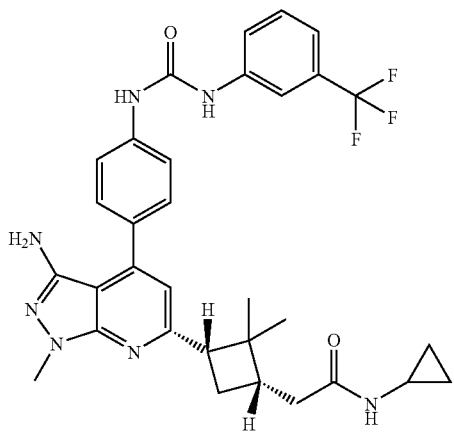

In analogy to GP 11, reaction of 691 mg Example Compound 8.3 (1.22 mmol, 1 eq.) with 0.17 ml cyclopropylamine (2.44 mmol, 2 eq.), 0.67 ml 4-methylmorpholine (5 eq.) and 1.44 ml 2,4,6-tripropyl-[1,3,5,2,4,6]trioxa-triphosphinane 2,4,6-trioxide (T3P; 2 eq.) in 38.46 ml DCM yielded 354 mg of the desired product (48% yield).

$^1$H-NMR (d$_6$-DMSO; 300 MHz): 9.13 (s, 1H); 9.06 (s, 1H); 8.04 (s, 1H); 7.84 (d, 1H); 7.66 (d, 2H); 7.61 (m, 1H); 7.54 (d, 2H); 7.52 (m, 1H); 7.33 (m, 1H); 6.61 (s, 1H); 4.61 (br. s, 2H); 3.81 (s, 3H); 3.31 (m, 1H); 2.58 (m, 1H); 2.44-1.95 (m, 5H); 1.25 (s, 3H); 0.61 (s, 3H); 0.59 (m, 2H); 0.36 (m, 2H).

The following exemplary compounds 9.1 to 9.50 of the present invention are accessible applying procedures described above using the respective isocyanates for urea formation and methyl hydrazine in the cyclization step (see GP 4 and GP 5):

Example 9.1

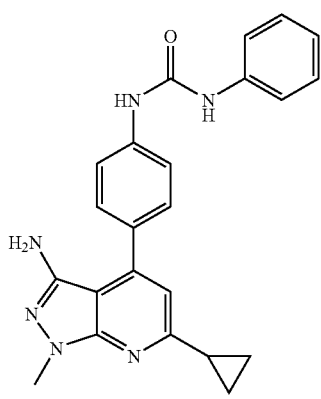

Example 9.2

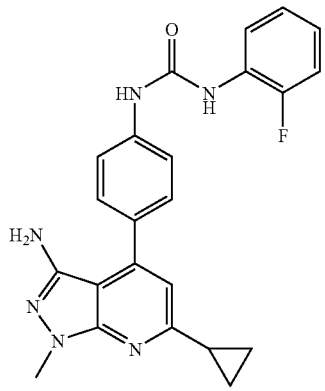

Example 9.3

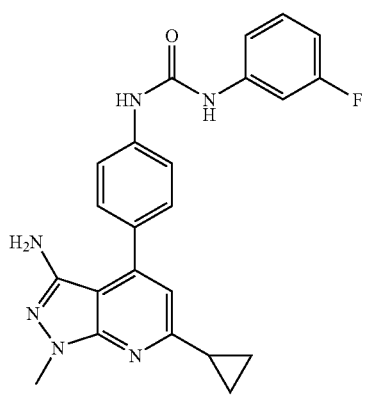

Example 9.4

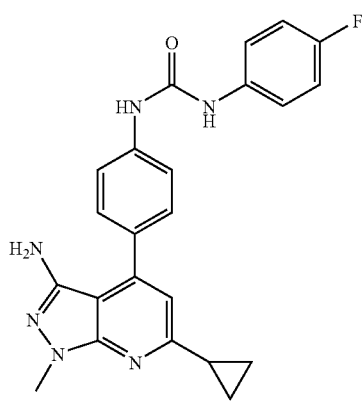

Example 9.5

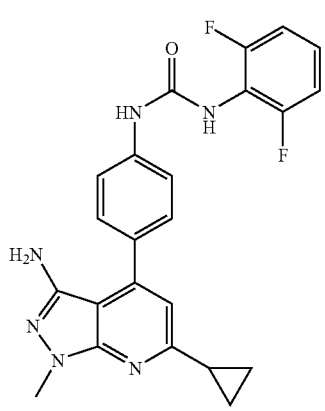

Example 9.6
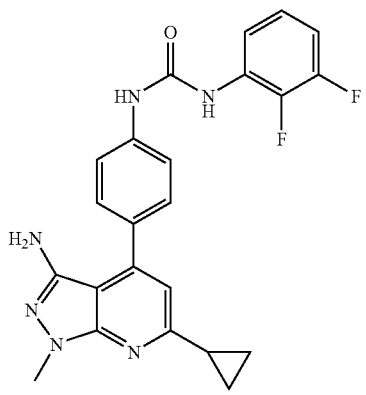
Example 9.7
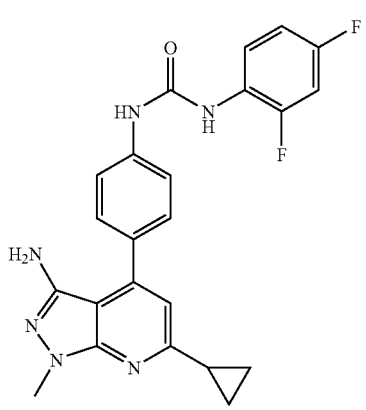
Example 9.8
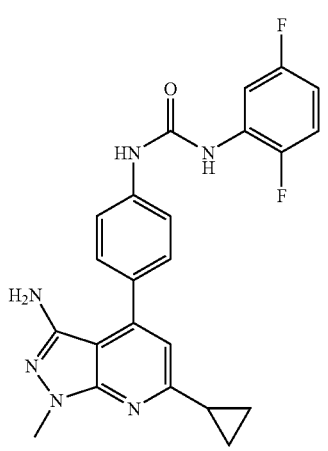
Example 9.9
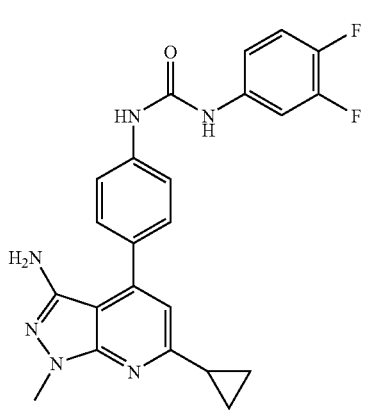
Example 9.10
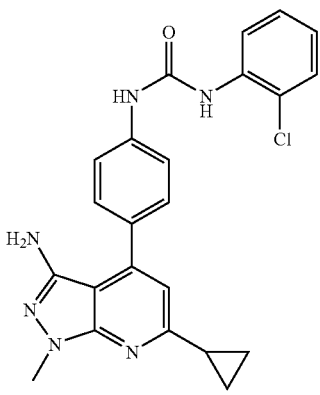
Example 9.11
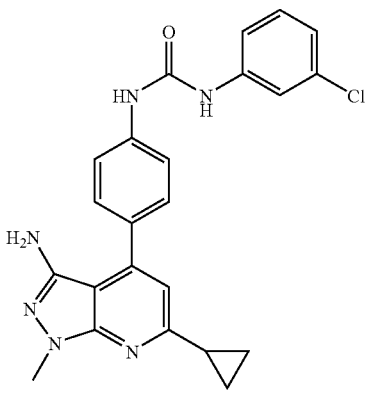
Example 9.12
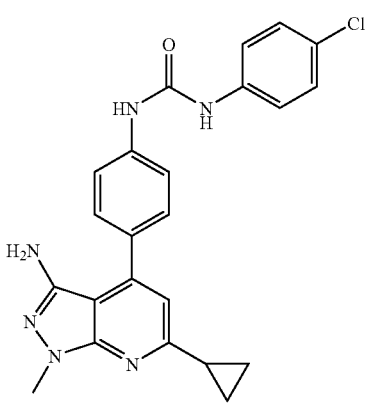
Example 9.13
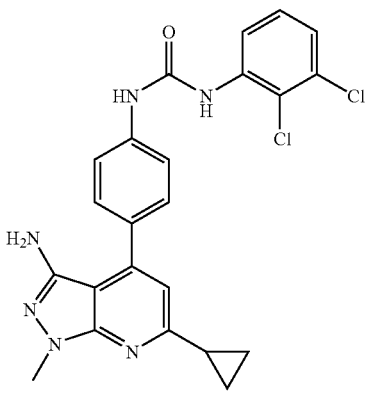

-continued
Example 9.14
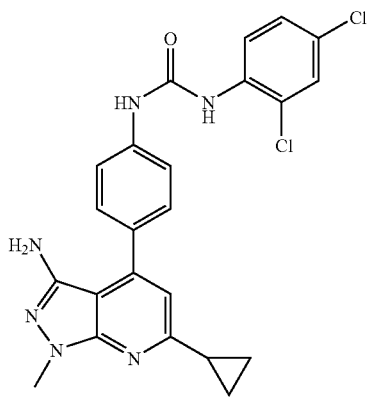
Example 9.15
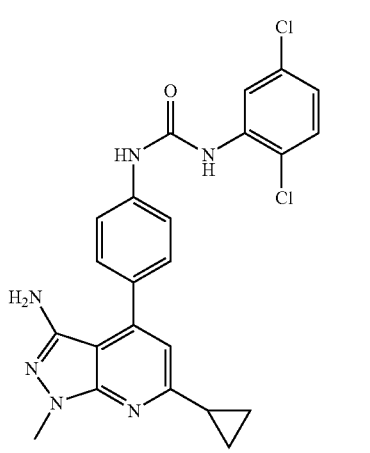
Example 9.16
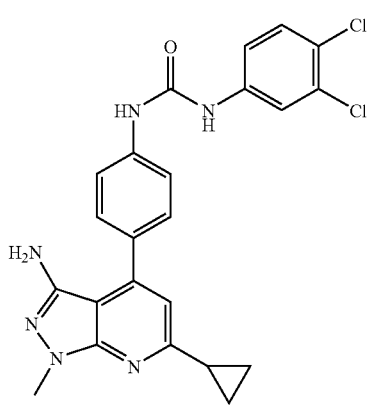
Example 9.17
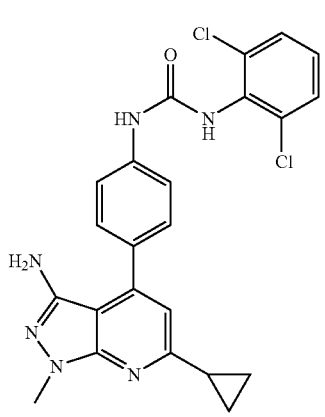
-continued
Example 9.18
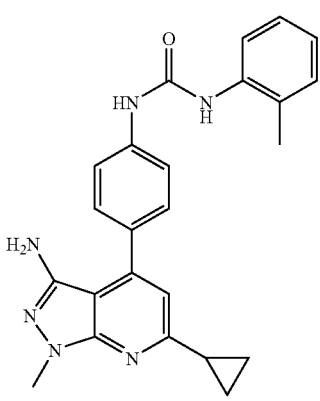
Example 9.19
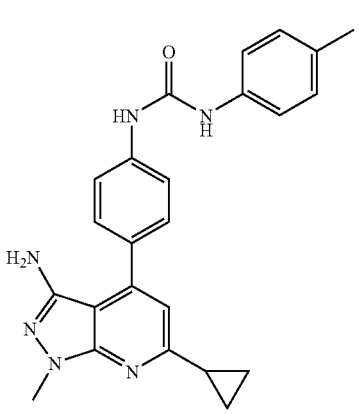
Example 9.20
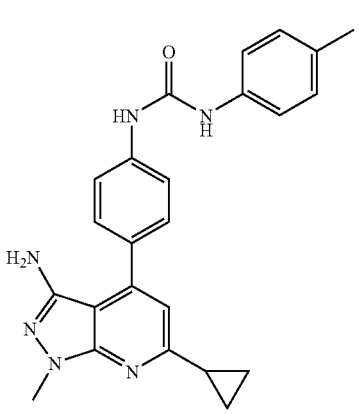
Example 9.21
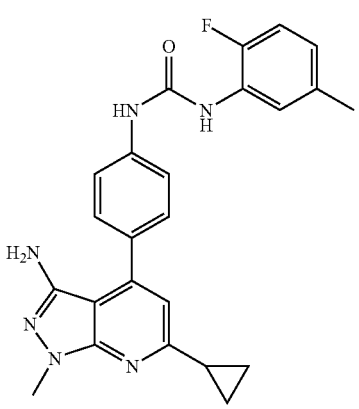

-continued
Example 9.22
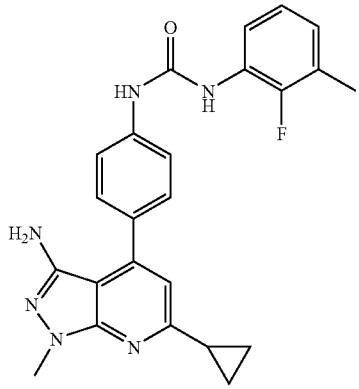
Example 9.23
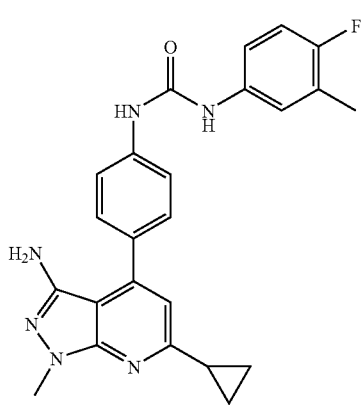
Example 9.24
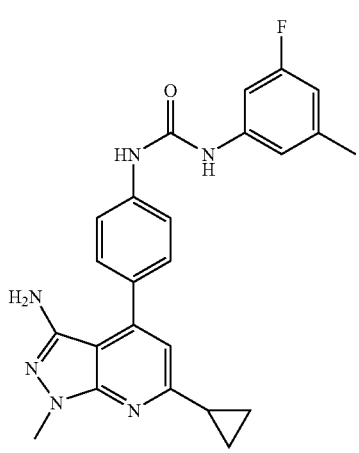
Example 9.25
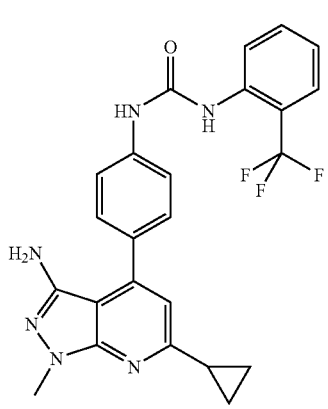
-continued
Example 9.26
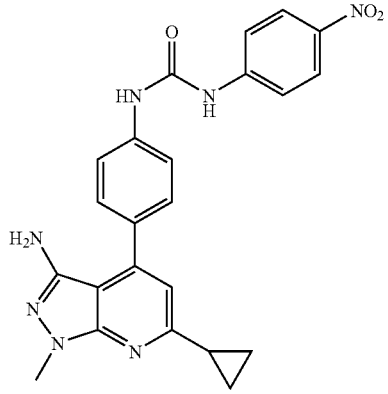
Example 9.27
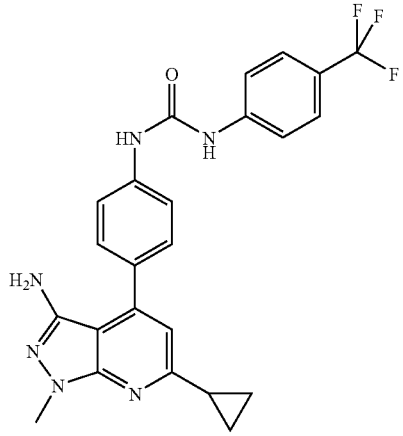
Example 9.28
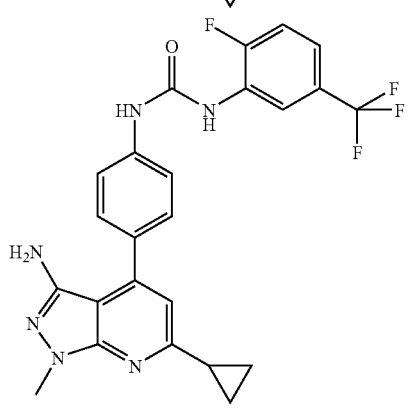
Example 9.29

-continued
Example 9.30
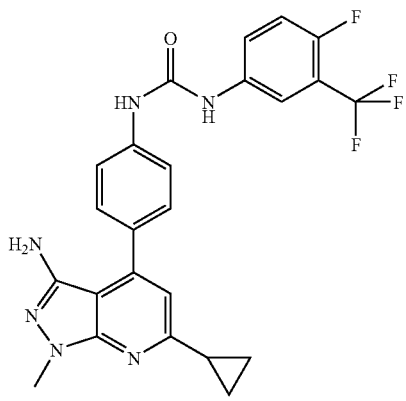
Example 9.31
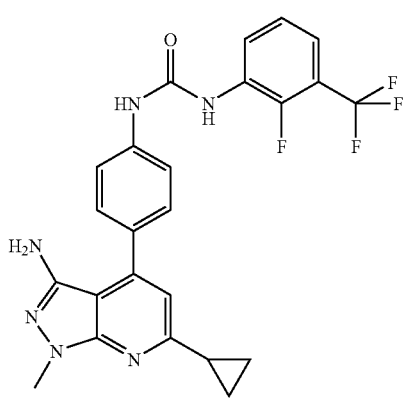
Example 9.32
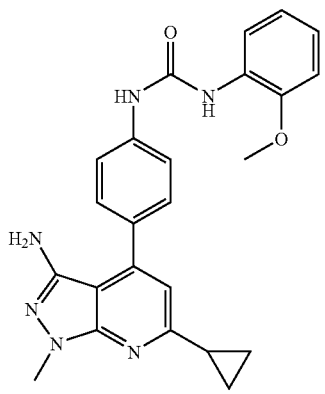
Example 9.33
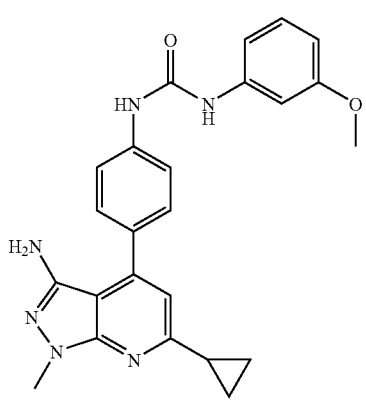
-continued
Example 9.34
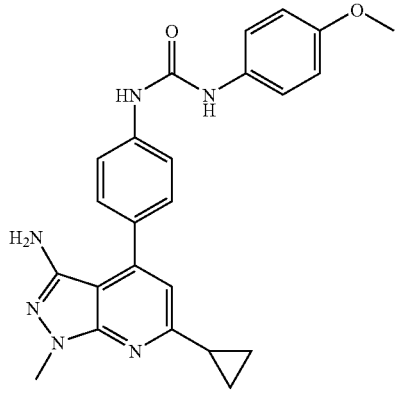
Example 9.35
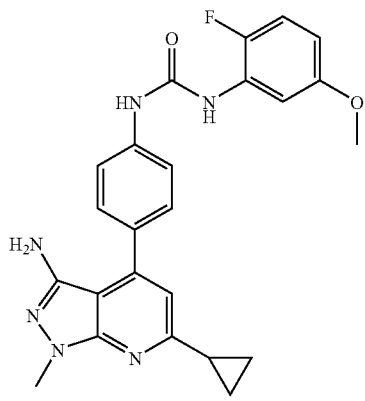
Example 9.36
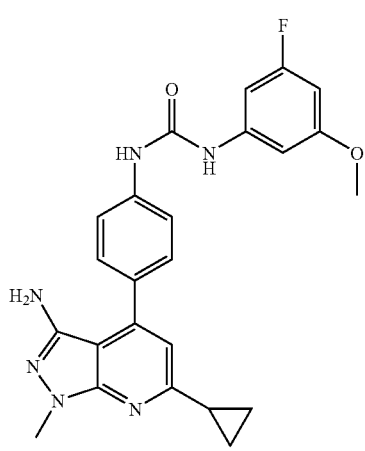
Example 9.37
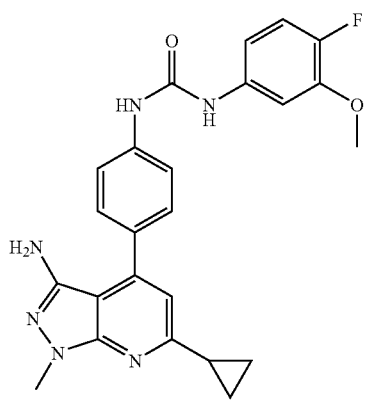

Example 9.38
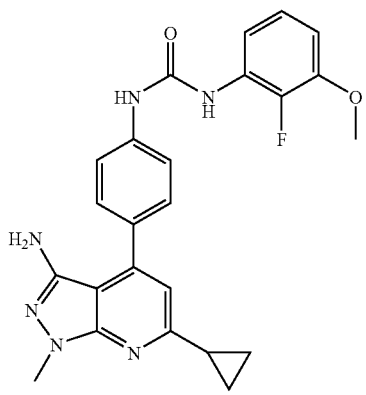
Example 9.39
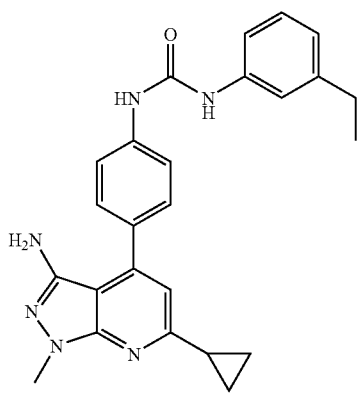
Example 9.40
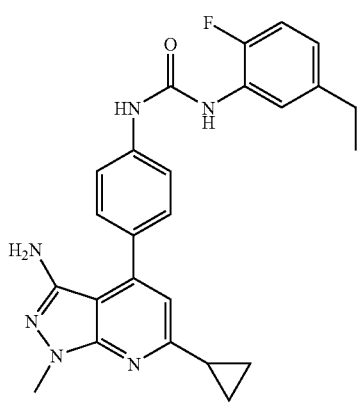
Example 9.41
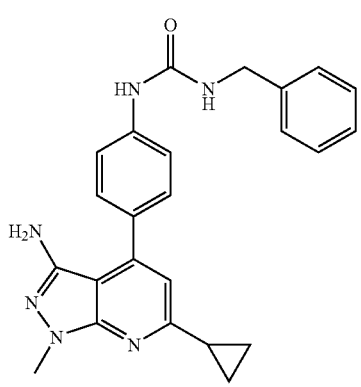
Example 9.42
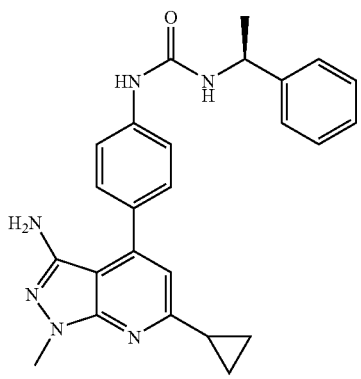
Example 9.43
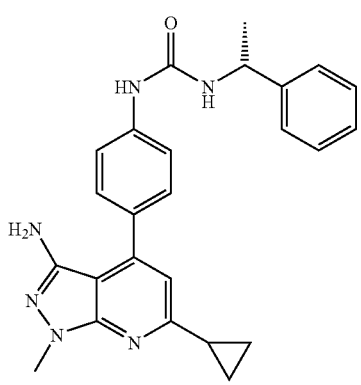
Example 9.44
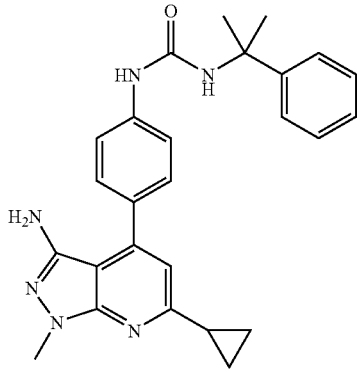
Example 9.45
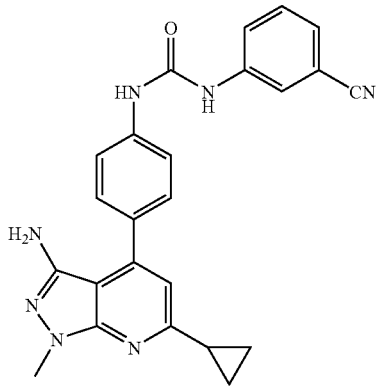

-continued
Example 9.46
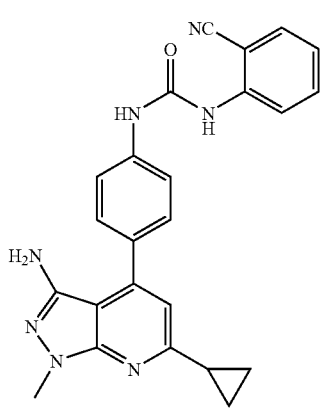
Example 9.47
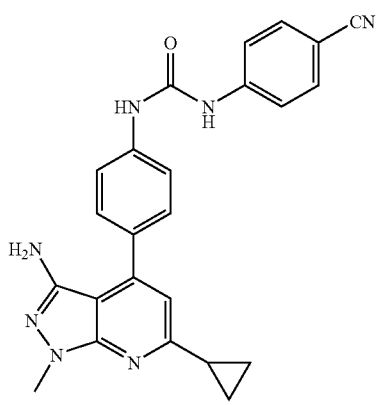
Example 9.48
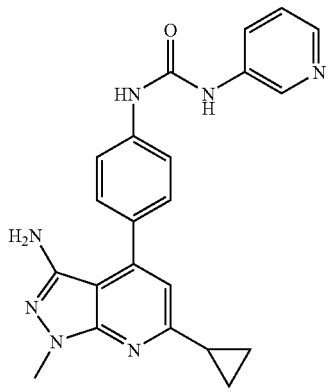
Example 9.49
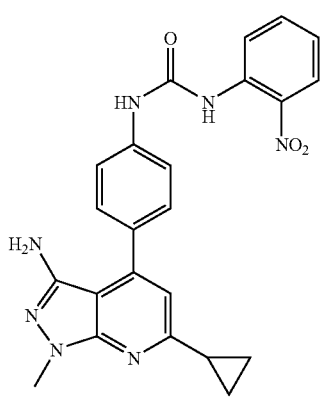
-continued
Example 9.50
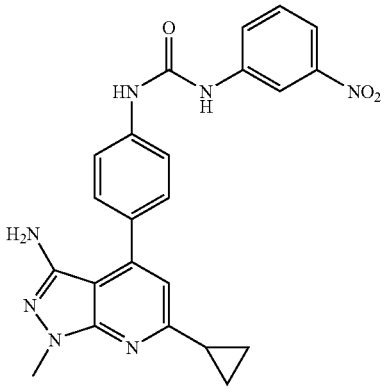
The following exemplary compounds 10.1 to 10.25 of the present invention are accessible applying procedures described above including triphosgene-mediated urea formation (see Scheme 2 and GP 7) from the respective anilines and subsequent cyclization with methyl hydrazine:
Example 10.1
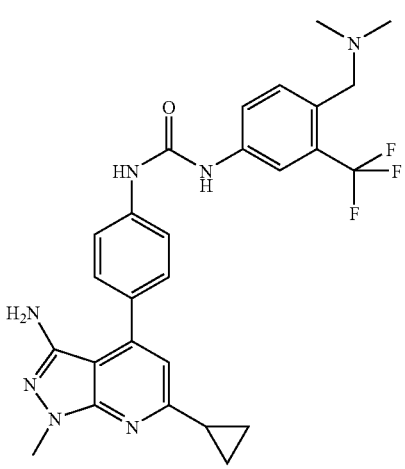
Example 10.2
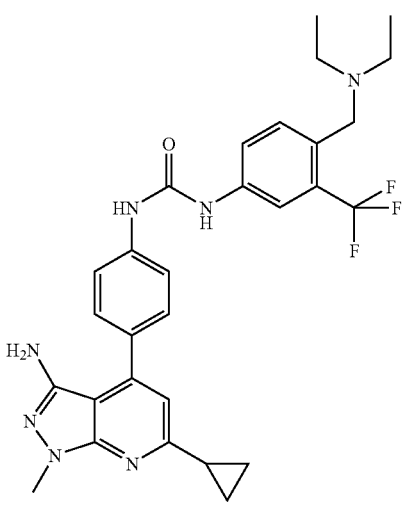

-continued
Example 10.3
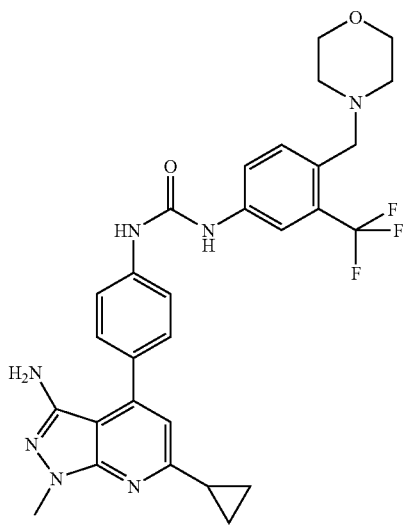
Example 10.4
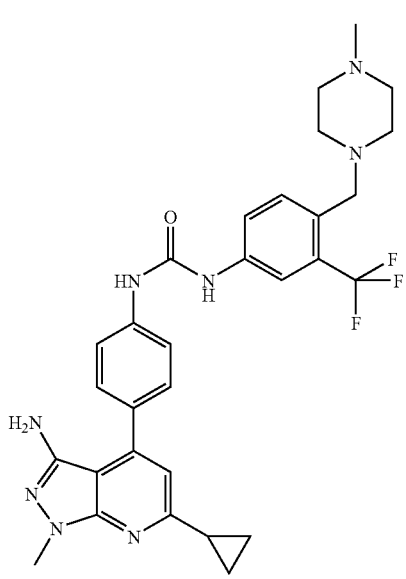
Example 10.5
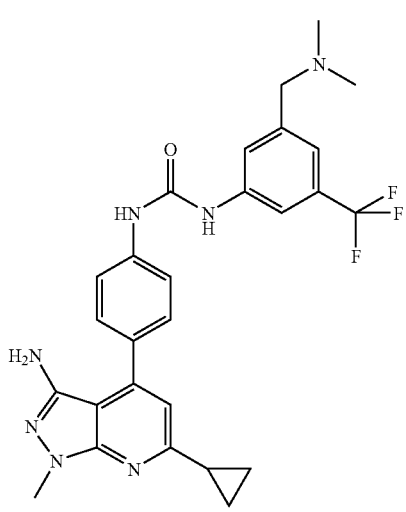
-continued
Example 10.6
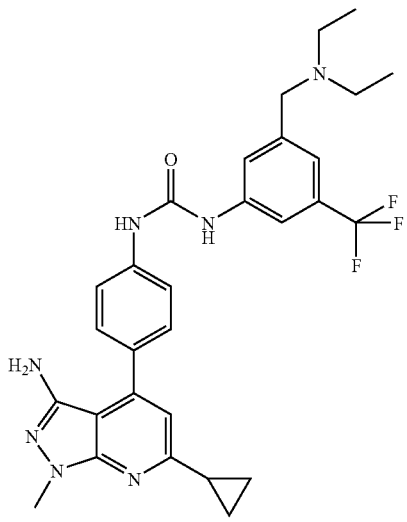
Example 10.7
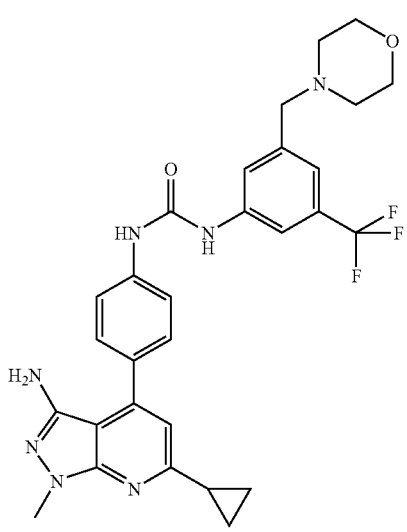
Example 10.8
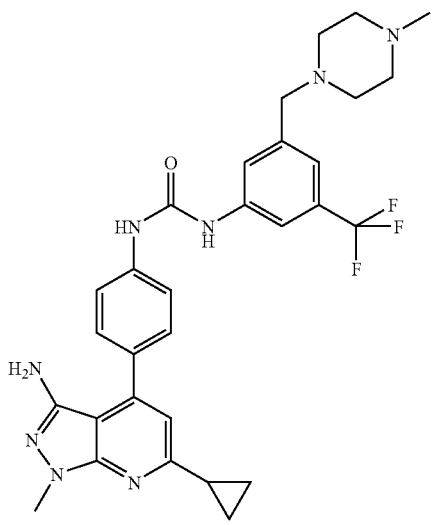

-continued
Example 10.9
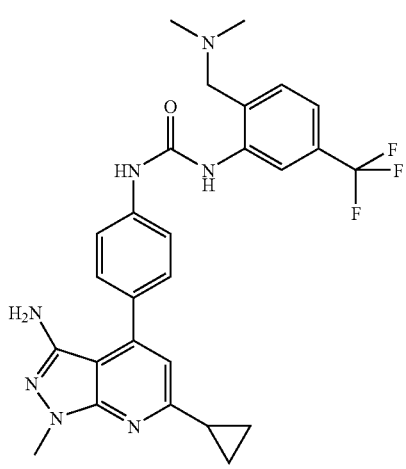
Example 10.10
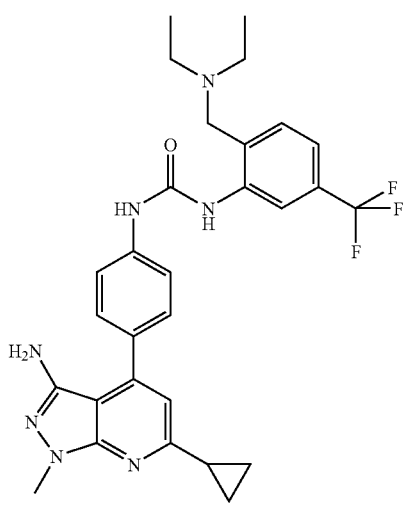
Example 10.11
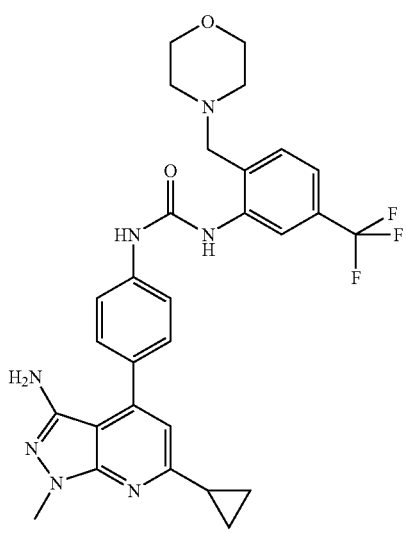
-continued
Example 10.12
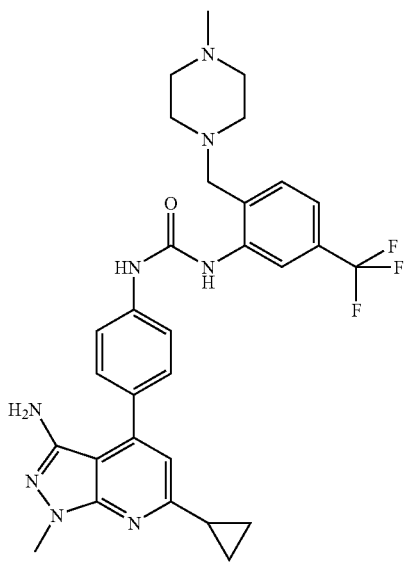
Example 10.13
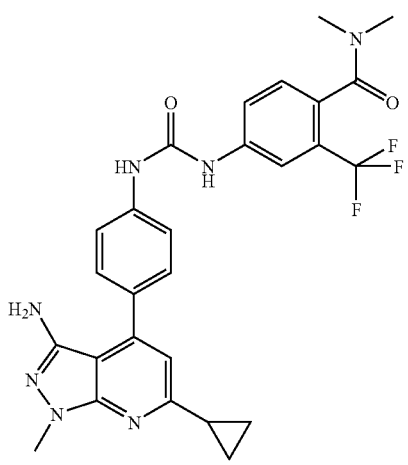
Example 10.14
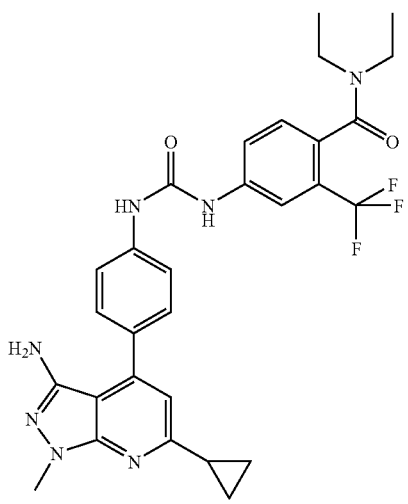

-continued
Example 10.15
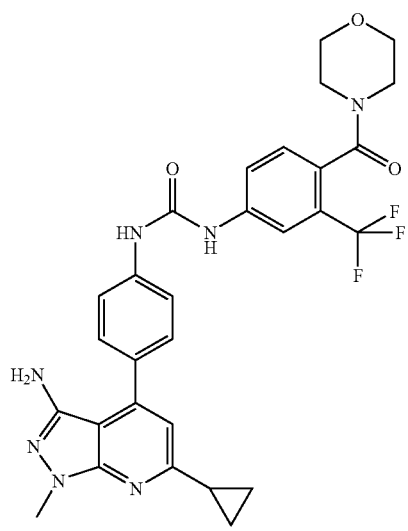
Example 10.16
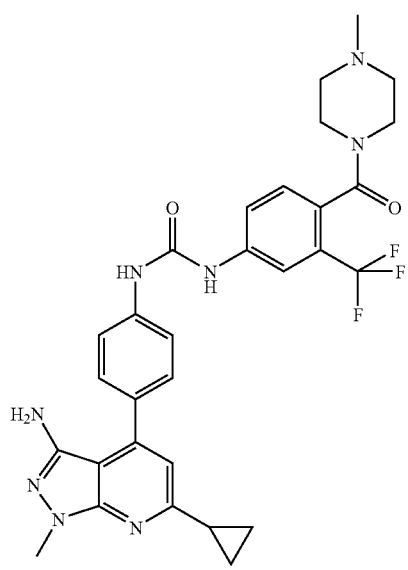
Example 10.17
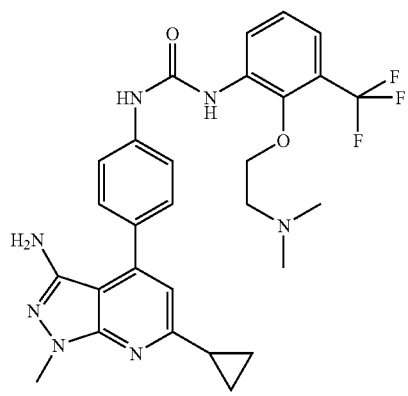
-continued
Example 10.18
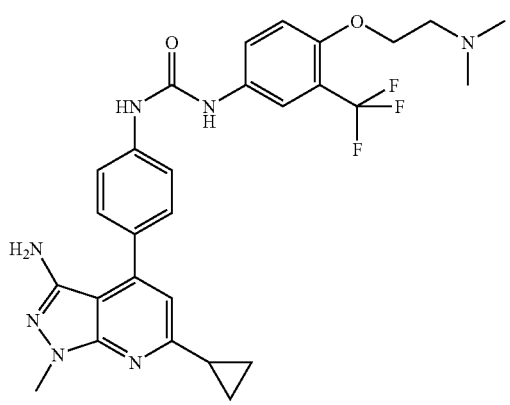
Example 10.19
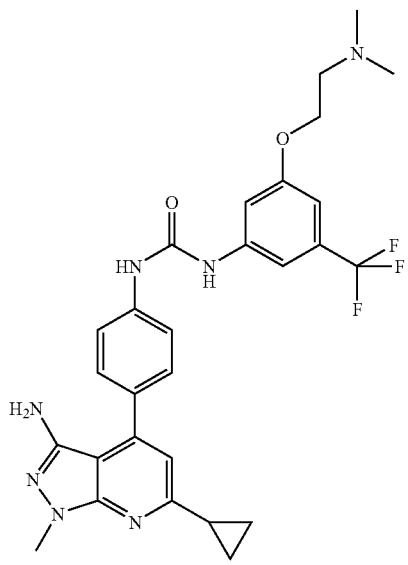
Example 10.20
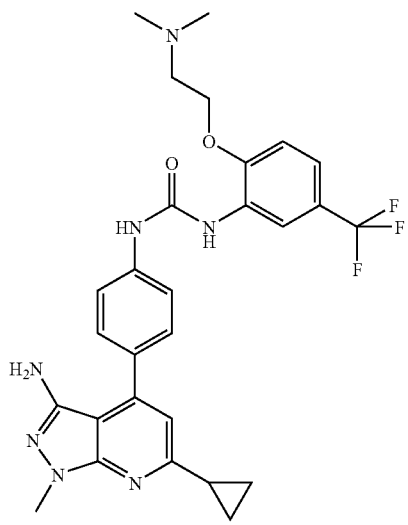

-continued

Example 10.21
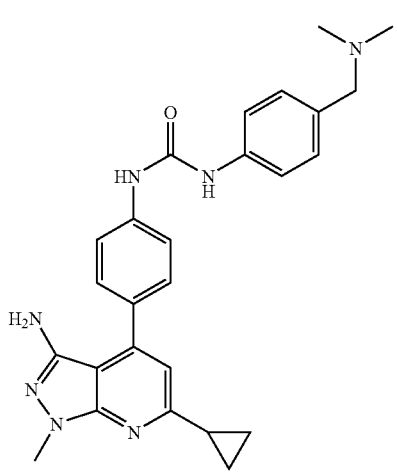

Example 10.22
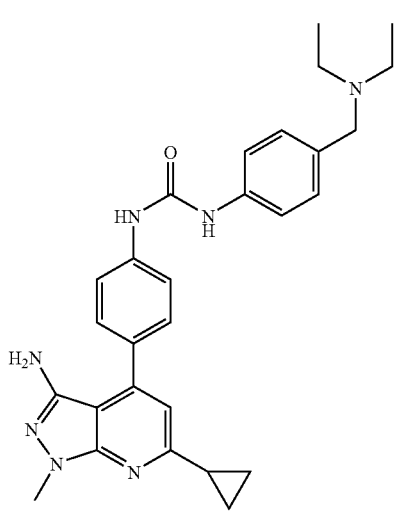

Example 10.23
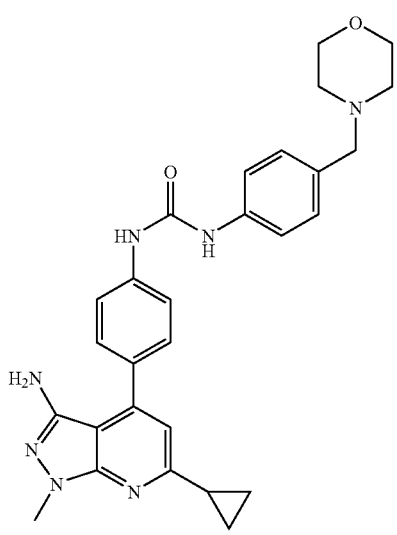

Example 10.24
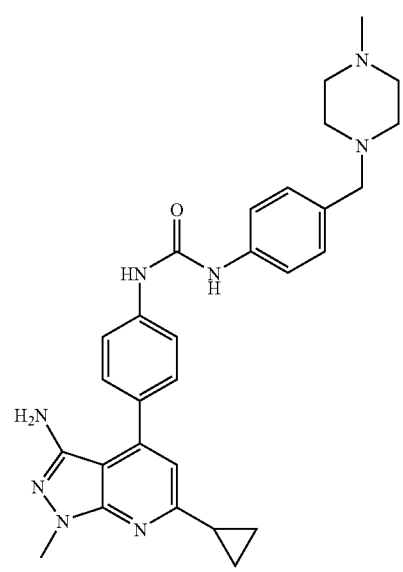

Example 10.25
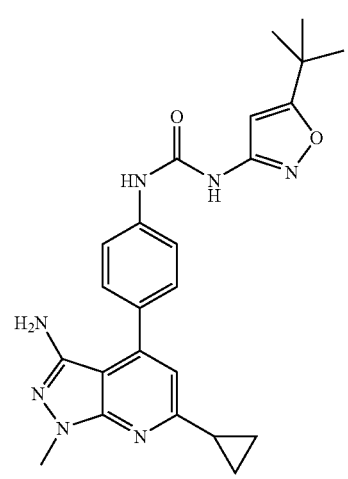

The following exemplary compounds 11.1 to 11.18 of the present invention are accessible applying procedures described above using the respective isocyanates or anilines for urea formation and higher substituted hydrazines in the cyclization step or cyclization with hydrazine hydrate and subsequent alkylation as described in GP 6 (see Scheme 4).

Example 11.1
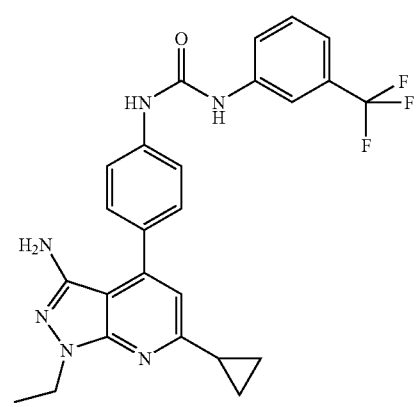

-continued
Example 11.2
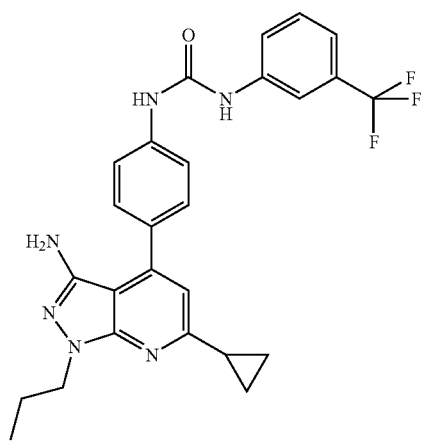
Example 11.3
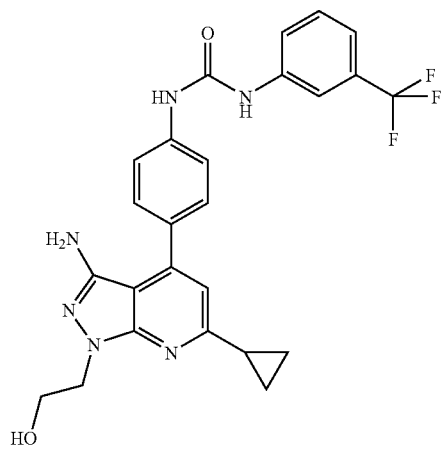
Example 11.4
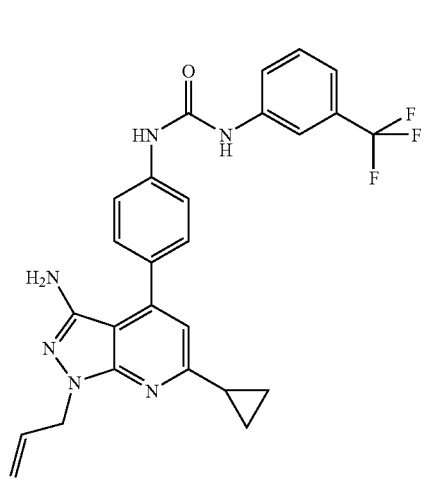
-continued
Example 11.5
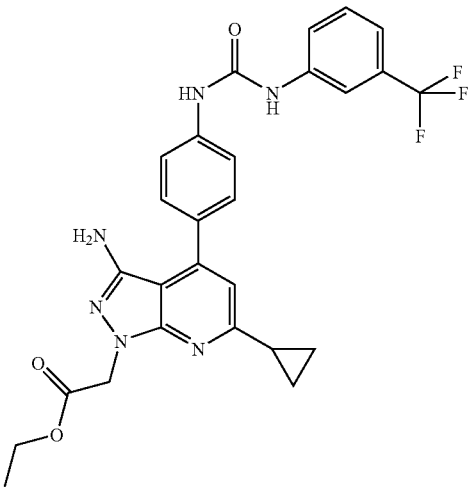
Example 11.6
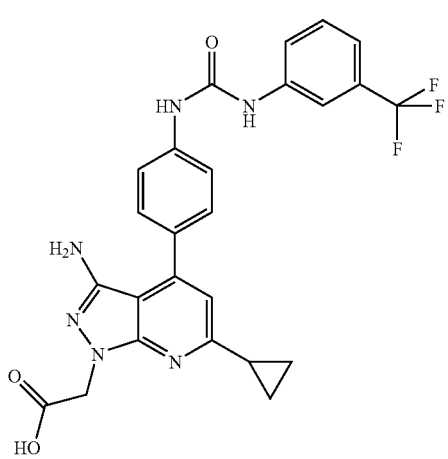
Example 11.7
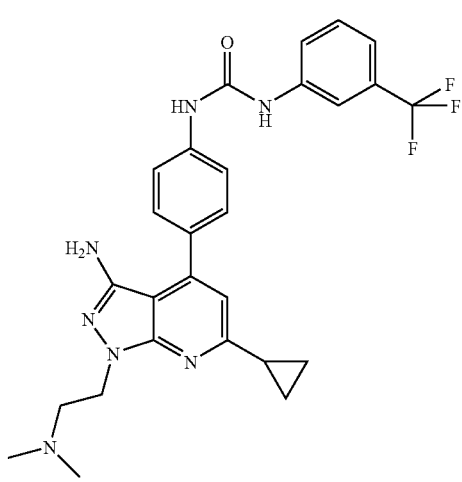

-continued
Example 11.8
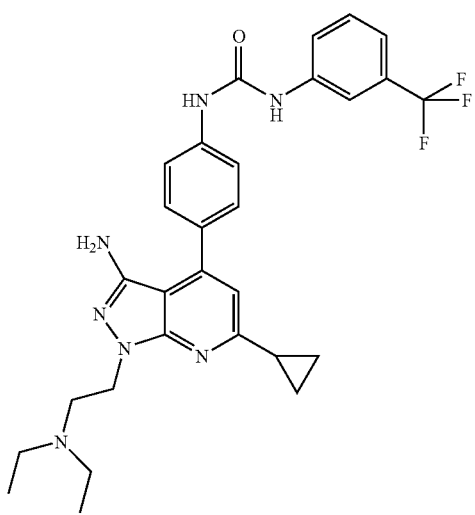
Example 11.9
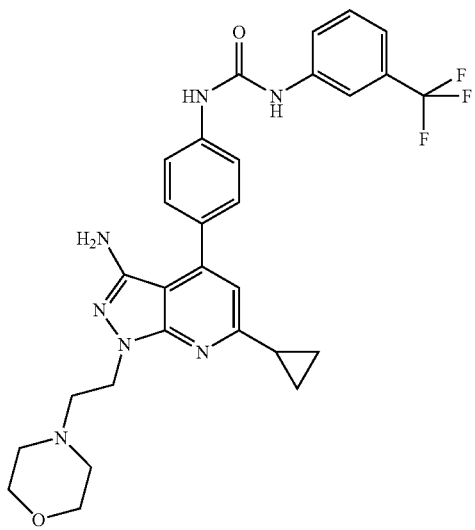
Example 11.10
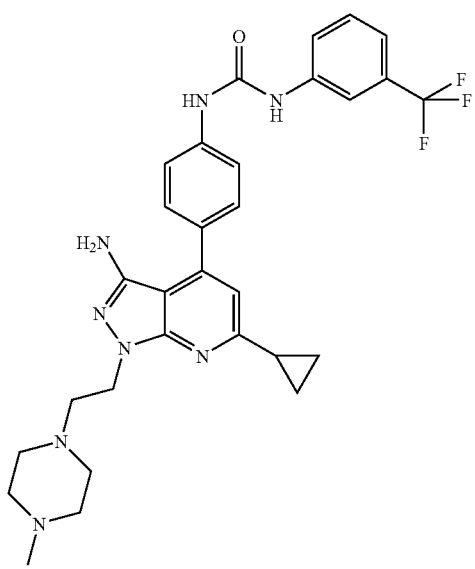
-continued
Example 11.11
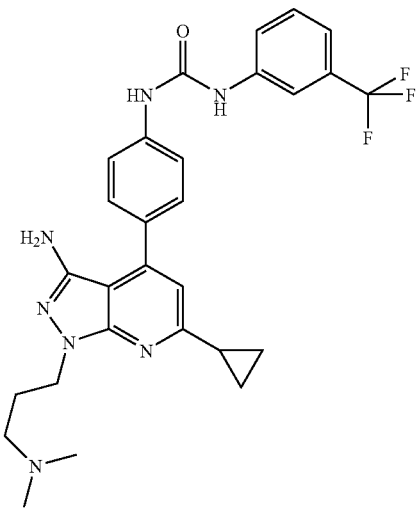
Example 11.12
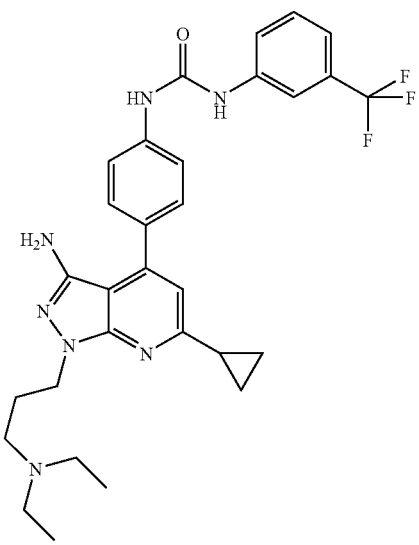
Example 11.13
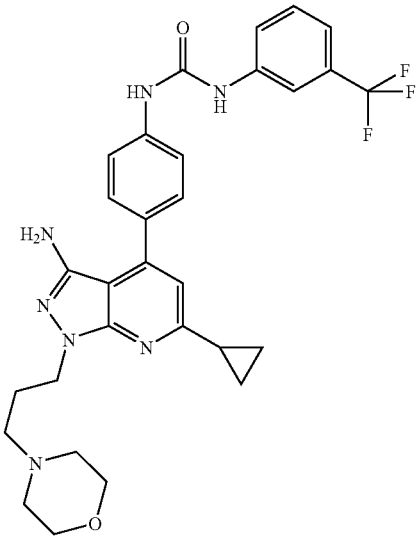

Example 11.14
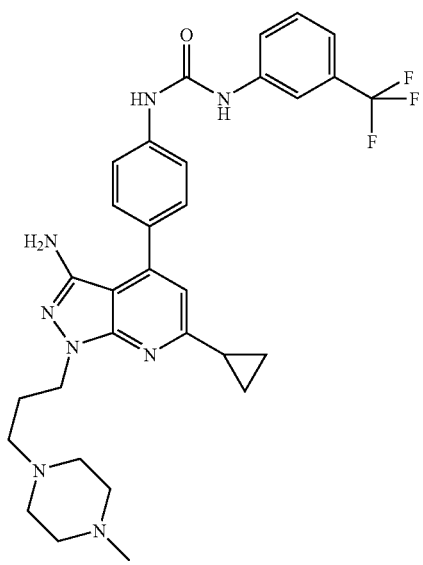
Example 11.17
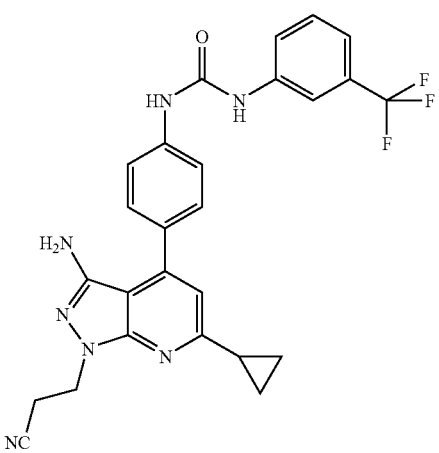
Example 11.15
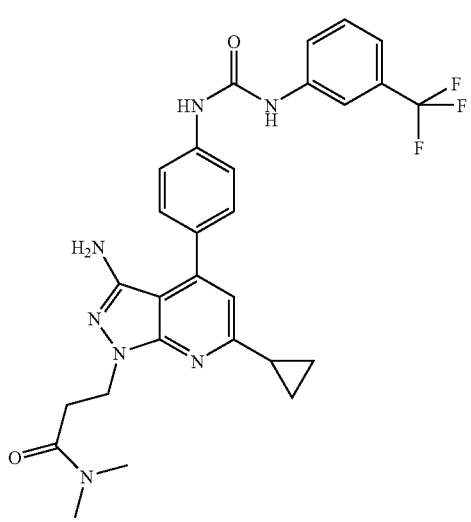
Example 11.18
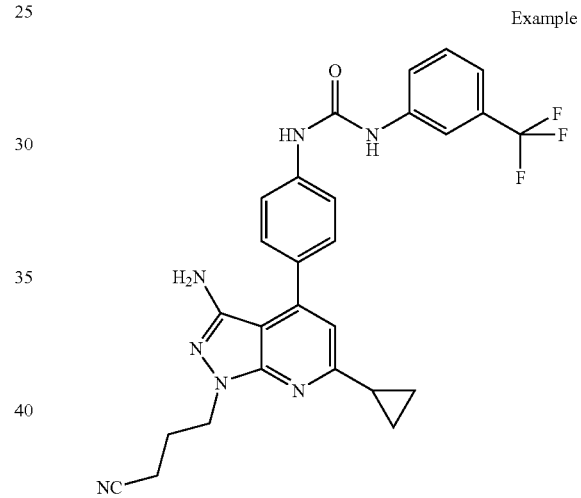
The following exemplary compounds 12.1 to 12.17 of the present invention are accessible applying processes described above starting from substrate 2a (see Scheme 6):
Example 11.16
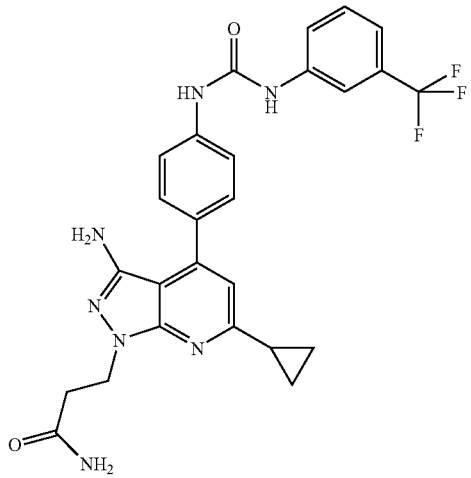
Example 12.1
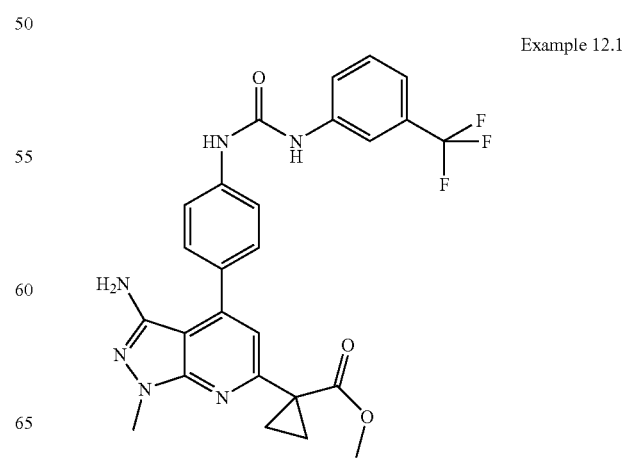

Example 12.2
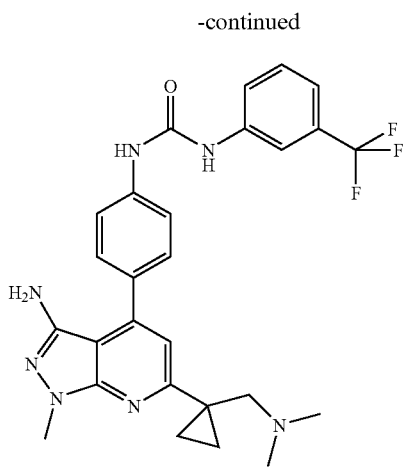
Example 12.3
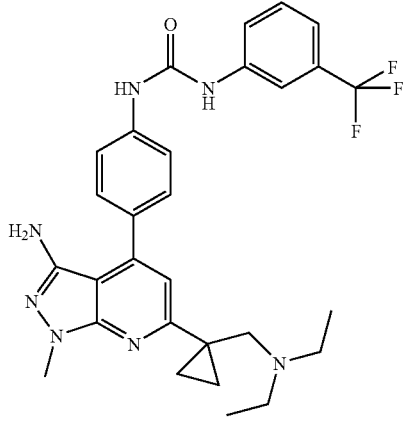
Example 12.4
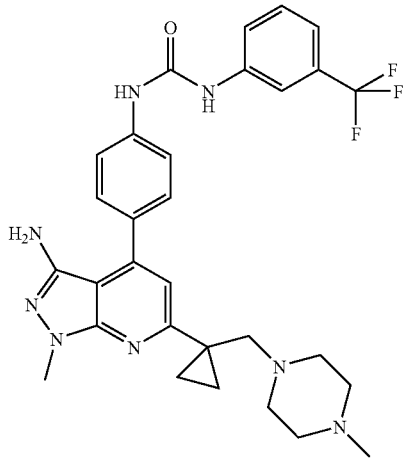
Example 12.5
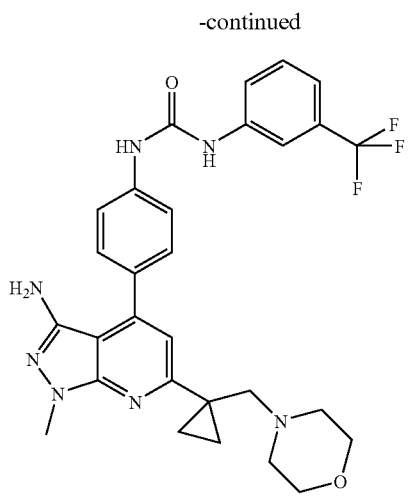
Example 12.6
Example 12.7
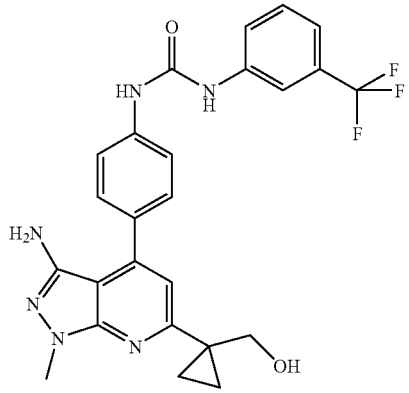

-continued
Example 12.8
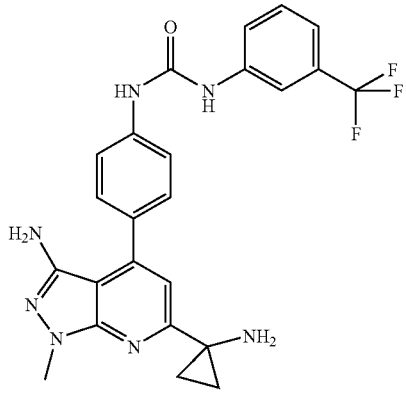
Example 12.9
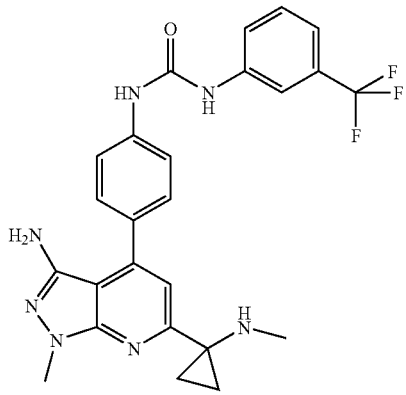
Example 12.10
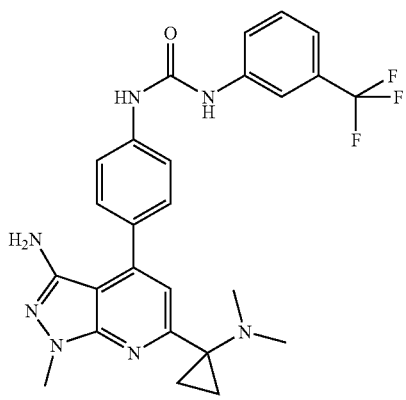
Example 12.11
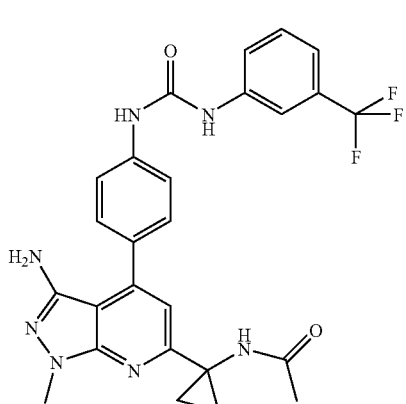
-continued
Example 12.12
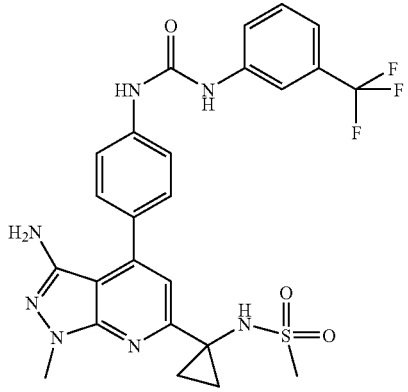
Example 12.13
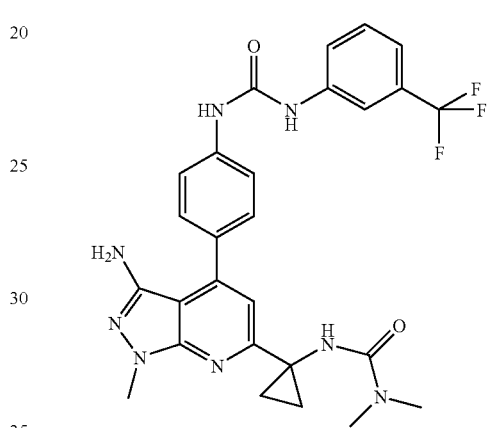
Example 12.14
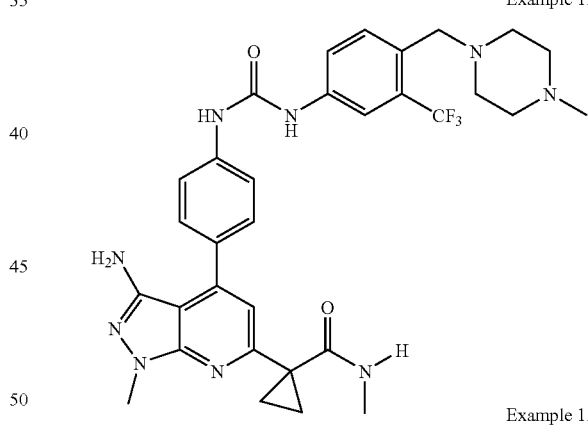
Example 12.15
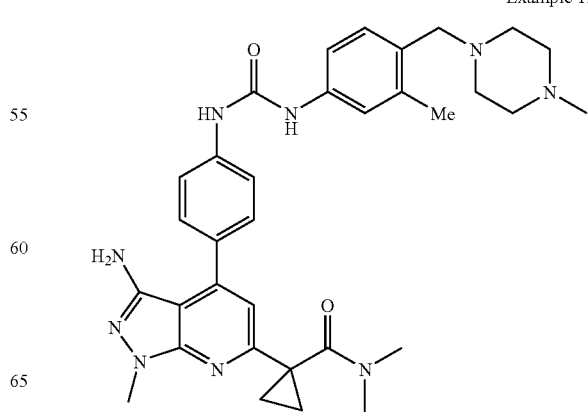

Example 12.16
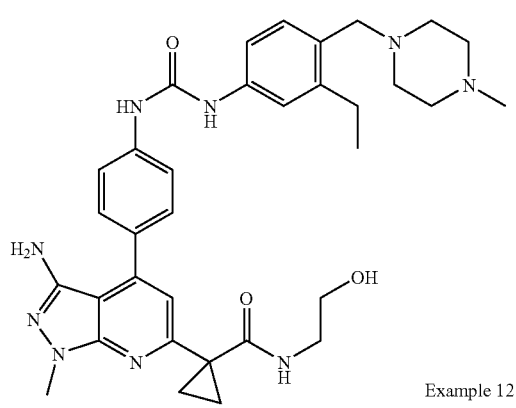
Example 12.17
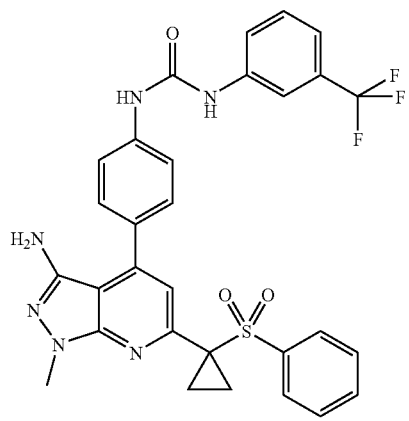
The following exemplary compounds 13.1 to 13.28 of the present invention are accessible by substituting the urea formation step as described before by sulphonamide formation as described in GP 8 or alternatively amide formation GP 9:
Example 13.1
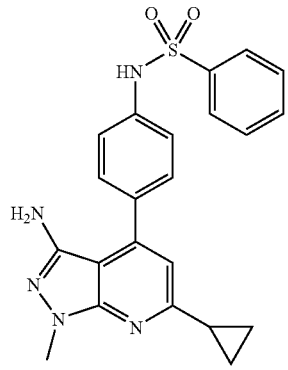
Example 13.2
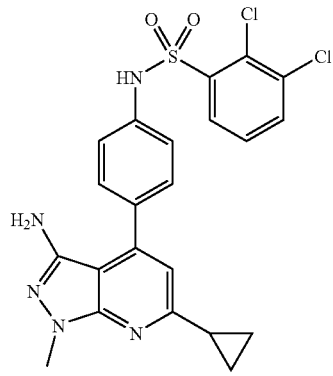
Example 13.3
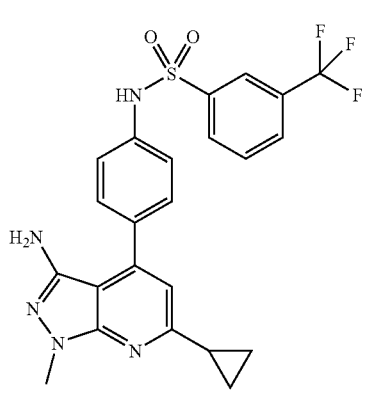
Example 13.4
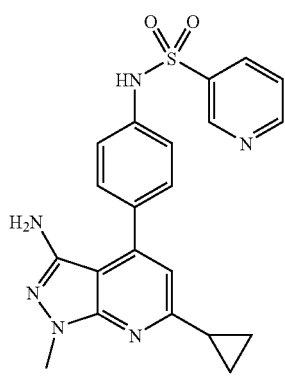
Example 13.5
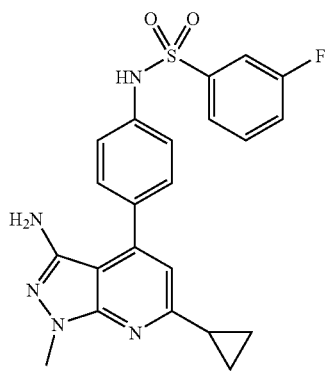
Example 13.6
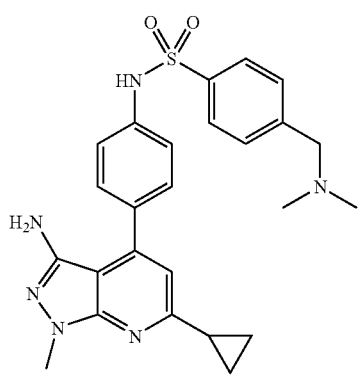

-continued
Example 13.7
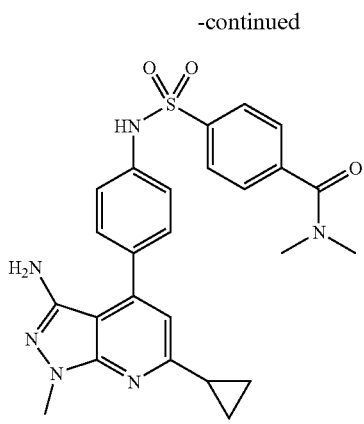
Example 13.8
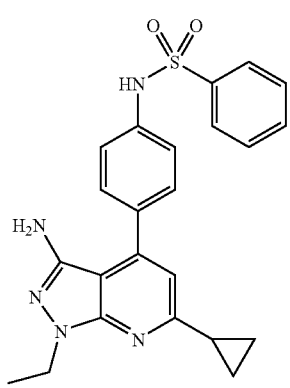
Example 13.9
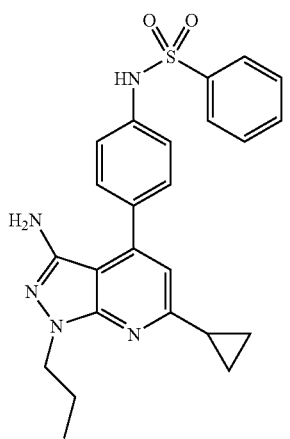
-continued
Example 13.10
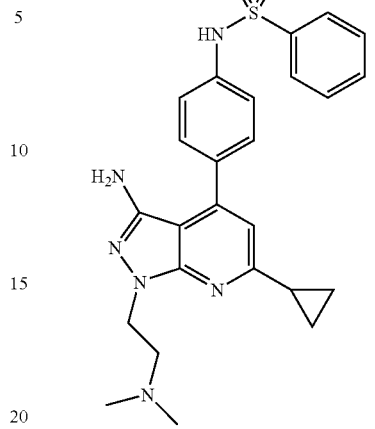
Example 13.11
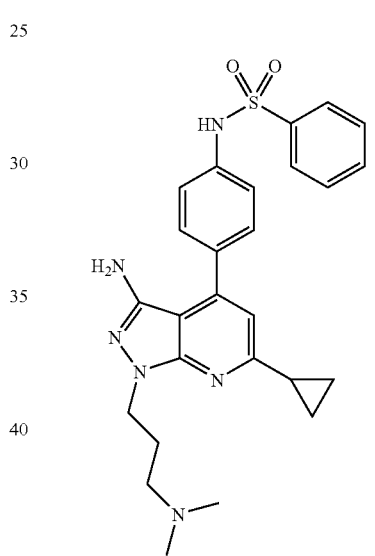
Example 13.12
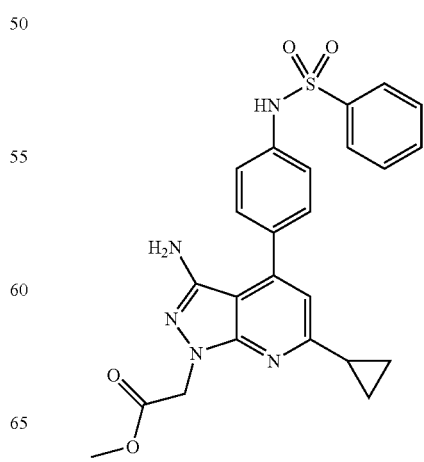

121
-continued
Example 13.13
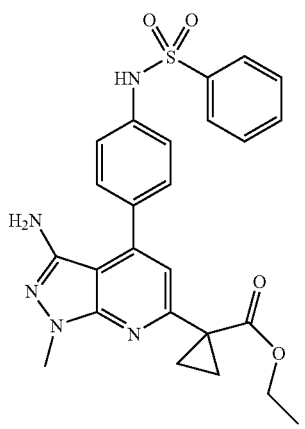
Example 13.14
Example 13.15
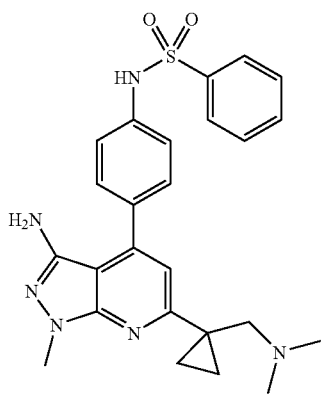
Example 13.16
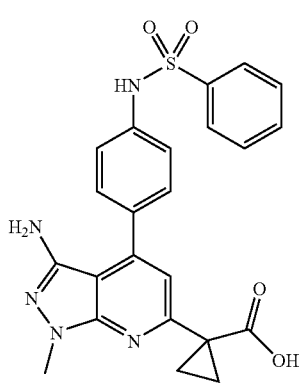
122
-continued
Example 13.17
Example 13.18
Example 13.19
Example 13.20

-continued
Example 13.21
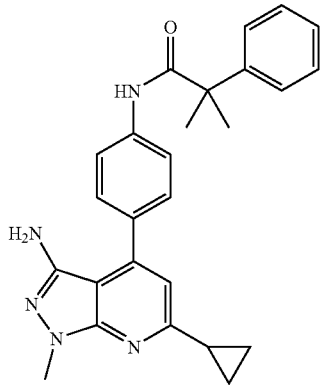
Example 13.22
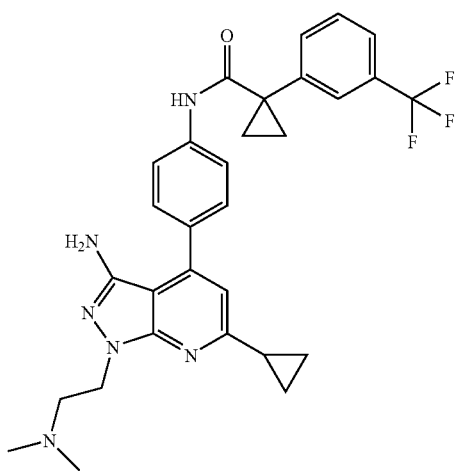
Example 13.23
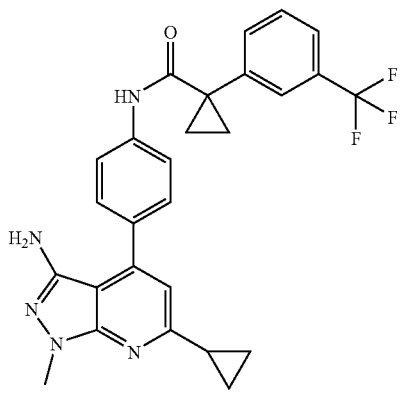
Example 13.24
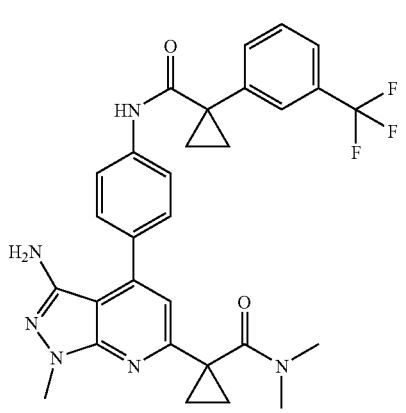
-continued
Example 13.25
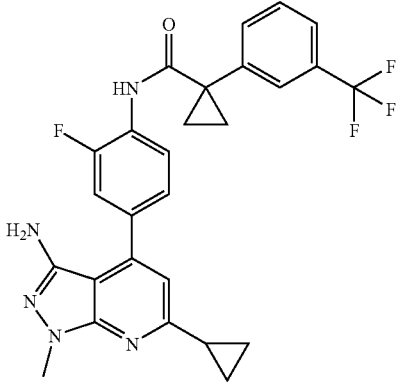
Example 13.26
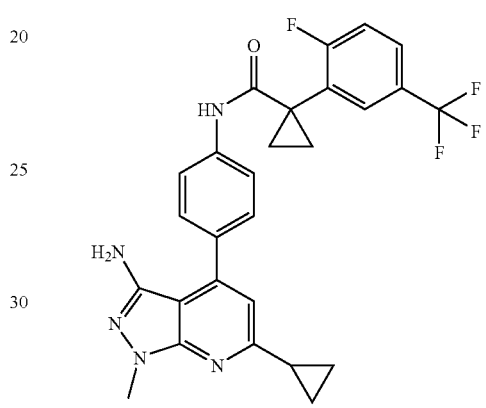
Example 13.27
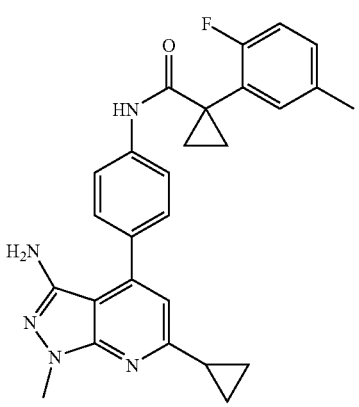
Example 13.28
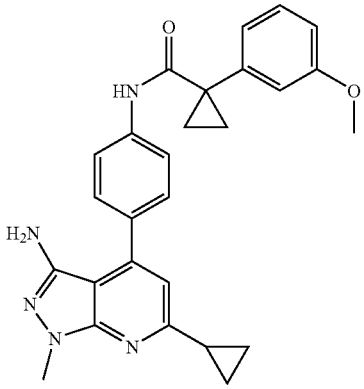

Biological Data

Assay 1: Tie2 ELISA Assay

Cellular activity of compounds of the present invention as inhibitors of Tie2 kinase activity was measured employing a Tie2 ELISA assay as described in the following paragraphs. Herein CHO cell-cultures, which are stably transfected by known techniques with Tie2 using DHFR deficiency as selection marker, are stimulated by angiopoietin-2. The specific autophosphorylation of Tie2 receptors is quantified with a sandwich-ELISA using anti-Tie2 antibodies for catch and anti-phosphotyrosine antibodies coupled to HRP for detection.

Materials:
  96 well tissue culture plate, sterile, Greiner
  96 well FluoroNunc plate MaxiSorp Surface C, Nunc
  96 well plate polypropylene for compound dilution in DMSO
  CHO Tie2/DHFR (transfected cells)
  PBS−; PBS++, DMSO
  MEM alpha Medium with Glutamax-I without Ribonucleosides and
    Deoxyribonucleosides (Gibco #32561-029)
    with 10% FCS after dialysis! and 1% PenStrep
  Lysis buffer: 1 Tablet "Complete" protease inhibitor
    1 cap Vanadate (1 mL>40 mg/mL; working solution 2 mM)
    ad 50 mL with Duschl-Puffer
    pH 7.6
  Anti-Tie2-antibody 1: 425 in Coating Buffer pH 9.6
    Stock solution: 1.275 mg/mL>working.: 3 µg/mL
  PBST: 2 bottles PBS(10×)+10 ml Tween, fill up with VE-water
  RotiBlock 1: 10 in VE-water
  Anti-Phosphotyrosine HRP-Conjugated 1:10000 in 3% TopBlock
    3% TopBlock in PBST
  BM Chemiluminescence ELISA Substrate (POD)
    solution B1: 100 solution A
  SF9 cell culture medium
  Ang2-Fc in SF9 cell culture medium Cell Experiment:
  Dispense $5\times10^4$ cells/well/98 µL in 96 well tissue culture plate
  Incubate at 37° C./5% $CO_2$
  After 24 h add compounds according to desired concentrations
  Add also to control and stimulated values without compounds 2 µL DMSO
  And mix for a few min at room temperature
  Add 100 µL Ang2-Fc to all wells except control, which receives insect medium
  Incubate 20 min at 37° C.
  Wash 3× with PBS++
  Add 100 µl Lysis buffer/well and shake a couple of min at room temperature
  Store lysates at 20° C. before utilizing for the ELISA Performance of Sandwich-ELISA
  Coat 96 well FluoroNunc Plate MaxiSorp Surface C with anti-Tie2 mAb
    1: 425 in Coating buffer pH 9.6; 100 µL/well overnight at 4° C.
  Wash 2× with PBST
  Block plates with 250 µL/well RotiBlock 1: 10 in VE-water
  Incubate for 2 h at room temperature or overnight at 4° C. shaking
  Wash 2× in PBST
  Add thawed lysates to wells and incubate overnight shaking at 4° C.
  Wash 2× with PBST
  Add 100 µL/well anti-Phosphotyrosine HRP-Conjugated 1: 10000 in 3% TopBlock (3% TopBlock in PBST) and incubate overnight under shaking
  Wash 6× with PBST
  Add 100 µL/well BM Chemiluminescence ELISA Substrate (POD)
  solutions 1 und 2 (1:100)
  Determine luminescence with the LumiCount.

Assay 2: Tie-2-Kinase HTRF-Assay without Kinase Preactivation

Tie2-inhibitory activity of compounds of the present invention was quantified employing two Tie2 HTRF assay as described in the following paragraphs.

A recombinant fusion protein of GST and the intracellular domains of Tie-2, expressed in insect cells (Hi-5) and purified by Glutathion-Sepharose affinity chromatography was used as kinase. Alternatively, commercially available GST-Tie2-fusion protein (Upstate Biotechnology, Dundee, Scotland) can be used As substrate for the kinase reaction the biotinylated peptide biotin-Ahx-EPKDDAYPLYSDFG (C-terminus in amid form) was used which can be purchased e.g. from the company Biosynthan GmbH (Berlin-Buch, Germany). Detection of phosphorylated product is achieved specifically by a trimeric detection complex consisting of the phosphorylated substrate, streptavidin-XLent (SA-XLent) which binds to biotin, and Europium Cryptate-labeled anti-phosphotyrosine antibody PT66 which binds to phosphorylated tyrosine.

Tie-2 (3.5 ng/measurement point) was incubated for 60 min at 22° C. in the presence of 10 µM adenosine-tri-phosphate (ATP) and 1 µM substrate peptide (biotin-Ahx-EPKDDAYPLYSDFG-$NH_2$) with different concentrations of test compounds (0 µM and concentrations in the range 0.001-20 µM) in 5 µl assay buffer [50 mM Hepes/NaOH pH 7, 10 mM $MgCl_2$, 0.5 mM $MnCl_2$, 1.0 mM dithiothreitol, 0.01% NP40, protease inhibitor mixture ("Complete w/o EDTA" from Roche, 1 tablet per 2.5 ml), 1% (v/v) dimethylsulphoxide]. The reaction was stopped by the addition of 5 µl of an aqueous buffer (25 mM Hepes/NaOH pH 7.5, 0.28% (w/v) bovine serum albumin) containing EDTA (90 mM) and the HTRF (Homogeneous Time Resolved Fluorescence) detection reagents streptavidine-XLent (0.2 µM, from Cis Biointernational, Marcoule, France) and PT66-Eu-Chelate (0.3 ng/µl; a europium-chelate labelled anti-phospho-tyrosine antibody from Perkin Elmer).

The resulting mixture was incubated 1 h at 22° C. to allow the binding of the biotinylated phosphorylated peptide to the streptavidine-XLent and the PT66-Eu-Chelate. Subsequently the amount of phosphorylated substrate peptide was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate peptide. The data were normalised (enzyme reaction without inhibitor=0% inhibition, all other assay components but no enzyme=100% inhibition) and $IC_{50}$ values were calculated by a 4 parameter fit using an inhouse software.

Assay 3: Tie-2-Kinase HTRF-Assay with Kinase Preactivation

A recombinant fusion protein of GST and the intracellular domains of Tie-2, expressed in insect cells (Hi-5) and purified by Glutathion-Sepharose affinity chromatography was used as kinase. As substrate for the kinase reaction the biotinylated peptide biotin-Ahx-EPKDDAYPLYSDFG (C-terminus in amid form) was used which can be purchased e.g. from the company Biosynthan GmbH (Berlin-Buch, Germany).

For activation, Tie-2 was incubated at a conc. 12.5 ng/µl of for 20 min at 22° C. in the presence of 250 µM adenosine-tri-phosphate (ATP) in assay buffer [50 mM Hepes/NaOH pH 7, 10 mM $MgCl_2$, 0.5 mM $MnCl_2$, 1.0 mM dithiothreitol, 0.01% NP40, protease inhibitor mixture ("Complete w/o EDTA" from Roche, 1 tablet per 2.5 ml)].

For the subsequent kinase reaction, the preactivated Tie-2 (0.5 ng/measurement point) was incubated for 20 min at 22° C. in the presence of 10 µM adenosine-tri-phosphate (ATP) and 1 µM substrate peptide (biotin-Ahx-EPKDDAYPLYS-DFG-$NH_2$) with different concentrations of test compounds (0 µM and concentrations in the range 0.001-20 µM) in 5 µl assay buffer [50 mM Hepes/NaOH pH 7, 10 mM $MgCl_2$, 0.5 mM $MnCl_2$, 0.1 mM sodium ortho-vanadate, 1.0 mM dithiothreitol, 0.01% NP40, protease inhibitor mixture ("Complete w/o EDTA" from Roche, 1 tablet per 2.5 ml), 1% (v/v) dimethylsulphoxide]. The reaction was stopped by the addition of 5 µl of an aqueous buffer (25 mM Hepes/NaOH pH 7.5, 0.28% (w/v) bovine serum albumin) containing EDTA (90 mM) and the HTRF (Homogeneous Time Resolved Fluorescence) detection reagents streptavidine-XLent (0.2 µM, from C is Biointernational, Marcoule, France) and PT66-Eu-Chelate (0.3 ng/µl; a europium-chelate labelled anti-phospho-tyrosine antibody from Perkin Elmer).

The resulting mixture was incubated 1 h at 22° C. to allow the binding of the biotinylated phosphorylated peptide to the streptavidine-XLent and the PT66-Eu-Chelate. Subsequently the amount of phosphorylated substrate peptide was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate peptide. The data were normalised (enzyme reaction without inhibitor=0% inhibition, all other assay components but no enzyme=100% inhibition) and $IC_{50}$ values were calculated by a 4 parameter fit using an inhouse software.

Assay 4: cKIT-Kinase HTRF-Assay c-Kit-inhibitory activity of compounds of the present invention was quantified employing the c-kit HTRF assay as described in the following paragraphs. GST-tagged recombinant kinase domain of the human c-kit expressed in SF-9 cells was used as kinase. As substrate for the kinase reaction biotinylated poly-(Glu,Tyr) (Cis biointernational, France) was used.

c-Kit was incubated for 30 min at 22° C. in the presence of different concentrations of test compounds in 5 µl assay buffer [50 mM Hepes/NaOH pH 7.0, 1 mM $MgCl_2$, 5 mM $MnCl_2$, 1.0 mM dithiothreitol, 0.1 mM sodium ortho-vanadate, 10 µM adenosine-tri-phosphate (ATP), 1.3 µg/ml substrate, 0.001% (v/v) Nonidet-P40 (Sigma), 1% (v/v) dimethylsulfoxide]. The concentration of c-kit was adjusted depending of the activity of the enzyme lot and was chosen appropriate to have the assay in the linear range. The reaction was stopped by the addition of 5 µl of a solution of HTRF detection reagents (0.1 µM streptavidine-XLent and 1 nM PT66-Eu-Chelate, an europium-chelate labelled anti-phospho-tyrosine antibody from Perkin Elmer) in an aqueous EDTA-solution (80 mM EDTA, 0.2% (w/v) bovine serum albumin in 50 mM HEPES/NaOH pH 7.0).

The resulting mixture was incubated 1 h at 22° C. to allow the binding of the biotinylated phosphorylated peptide to the streptavidine-XLent and the PT66-Eu-Chelate. Subsequently the amount of phosphorylated substrate was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition) and IC50 values were calculated by a 4 parameter fit using an inhouse software.

Compounds of the present invention possess enzymatic and cellular activity as potent inhibitors of Tie2. Surprisingly, it was found that the compounds of the present invention differ from closest prior art compounds (see below) in their selectivity profile, for example in their significantly less potent inhibition of ckit kinase activity. Therefore, compounds of the present invention exert their kinase inhibitory activity primarily on endothelial cells whereas closest prior art compounds exert their activity on both endothelial as well as non-endothelial cells. As off-target-cell activity increases the risk of therapeutic side effects, especially in long-term treatment applications, compounds of the present invention having a selectivity profile significantly differing from prior art compounds are a much-needed extension of the small-molecule armament of potent Tie2 inhibitors for the treatment of diseases of dysregulated vascular growth or diseases which are accompanied with dysregulated vascular growth.

For benchmarking purposes, the following prior art compounds were profiled in the above described assays. The selection of compounds was guided by the availability of enabling descriptions in the corresponding patent documents, e.g. the actually exemplified structural space in WO2006/050109 being limited to pyrazolopyridines unsubstituted at the 6 position.

TABLE

| Prior art compounds | | | |
|---|---|---|---|
| Entry | Structure | Name | Source |
| PA1 | | 1-[4-(3-Amino-1H-indazol-4-yl)-phenyl]-3-(2-fluoro-5-methyl-phenyl)-urea | WO 2004/113404 (Example 5; Abt869) |
| PA2 | | 1-[4-(3-Amino-1H-pyrazolo[3,4-b]pyridin-4-yl)-phenyl]-3-(3-trifluoromethyl-phenyl)-urea | WO 2006/050109 (Example 19) |
| PA3 | | 1-[4-(3-Amino-1H-pyrazolo[3,4-b]pyridin-4-yl)-phenyl]-3-(2-fluoro-5-methyl-phenyl)-urea | WO 2006/050109 (Example 15) |
| PA4 | | 1-[4-(3-Amino-1-methyl-1H-pyrazolo[3,4-b]pyridin-4-yl)-phenyl]-3-(3-trifluoromethyl-phenyl)-urea | WO 2006/050109 (Example 43) |

TABLE-continued

Prior art compounds

| Entry | Structure | Name | Source |
|---|---|---|---|
| PA5 | 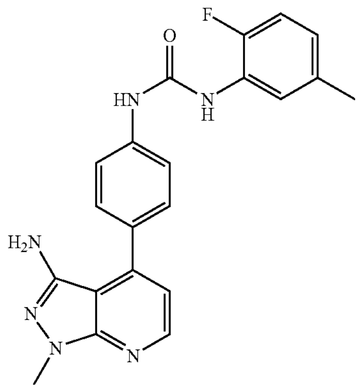 | 1-[4-(3-Amino-1-methyl-1H-pyrazolo[3,4-b]pyridin-4-yl)-phenyl]-3-(2-fluoro-5-methyl-phenyl)-urea | WO 2006/050109 (not exemplified) |
| PA6 | 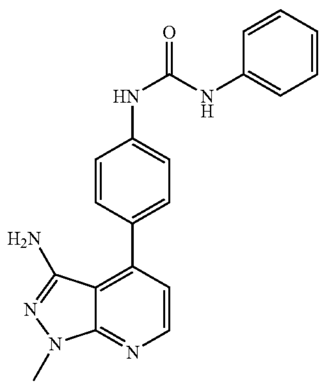 | 1-[4-(3-Amino-1-methyl-1H-pyrazolo[3,4-b]pyridin-4-yl)-phenyl]-3-phenyl-urea | WO 2006/050109 (not exemplified) |

Activity data are given in the following Table. The $IC_{50}$ values were converted to $pIC_{50}$ values, i.e. $-\log IC_{50}$ in molar concentration.

TABLE

Biological Data

| Example No. | Tie 2 activity (assay 1) | Tie 2 activity (assay 2) | cKit activity (assay 4) | Selectivity vs. cKit |
|---|---|---|---|---|
| 1.1 | ++ | ++ | + | 4 |
| 1.2 | +++ | +++ | + | >30 |
| 1.4 | ++ | +++ | ++ | 9 |
| 1.5 | ++ | +++ | + | >100 |
| 1.6 | +++ | +++ | + | >100 |
| 1.7 | ++ | ++ | + | 7 |
| 1.8 | +++ | ++ | + | 15 |
| 1.9 | ++ | +++ | ++ | 10 |
| 1.10 | +++ | +++ | + | 12 |
| 1.11 | +++ | +++ | + | 24 |
| 1.12 | +++ | +++ | + | >100 |
| 1.13 | +++ | +++ | + | >100 |
| 1.14 | ++ | +++ | ++ | 11 |
| 2.1 | +++ | +++ | ++ | 6 |
| 4.3 | +++ | +++ | + | >100 |
| 4.4 | +++ | +++ | + | 15 |
| 6.1 | +++ | +++ | + | 20 |
| 7.1 | +++ | +++ | ++ | 9 |
| 8.2 | +++ | +++ | + | 30 |
| 8.4 | | +++ | + | 19 |
| PA1 | +++ | +++ | +++ | 0.85 |
| PA2 | +++ | +++ | +++ | 0.67 |
| PA3 | ++ | +++ | +++ | 0.26 |
| PA4 | +++ | +++ | ++ | 1.6 |
| PA5 | +++ | ++ | +++ | 0.5 |
| PA6 | + | + | +++ | 0.06 |

+ stands for $pIC_{50}$ 5.0-6.0
++ stands for $pIC_{50}$ 6.0-7.0
+++ stands for $pIC_{50} \geq 7.0$
Selectivity vs. cKit: $IC_{50}$ assay 4/$IC_{50}$ assay 2

General Remarks

It is believed that one skilled in the art, using the preceding information and information available in the art, can utilize the present invention to its fullest extent. It should be apparent to one of ordinary skill in the art that changes and modifications can be made to this invention without departing from the spirit or scope of the invention as it is set forth herein. All publications, applications and patents cited above are incorporated herein by reference.

The topic headings set forth above and below are meant as guidance where certain information can be found in the application, but are not intended to be the only source in the application where information on such topic can be found.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 06090108.9, filed Jun. 13, 2006 and European application No. 07090024.6, and U.S. Provisional Application Ser. No. 60/816,624, filed Jun. 27, 2006 and U.S. Provisional Application Ser. No. 60/891,103 filed Feb. 22, 2007, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula (I):

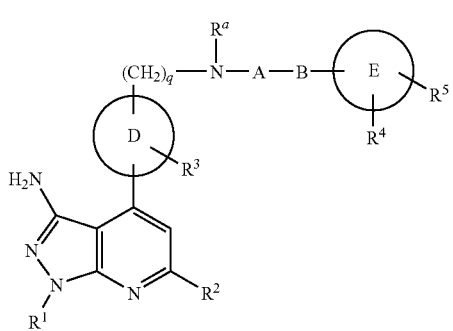

in which:
$R^1$ represents —C(O)$R^b$ or is selected from the group consisting of $C_1$-$C_6$-alkyl, $C_2$-$C_6$-alkenyl, $C_2$-$C_6$-alkynyl, $C_3$-$C_{10}$-cycloalkyl, and $C_3$-$C_{10}$-heterocycloalkyl, which are unsubstituted or substituted one or more times, independently from each other, with $R^6$;

$R^2$ represents a $C_3$-$C_{10}$-cycloalkyl optionally substituted with $R^7$;

$R^3$ is selected from the group consisting of hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen, and cyano;

$R^4$, $R^5$, $R^6$, $R^7$, $R^8$ independently from each other, are selected from the group consisting of hydrogen, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)$R^b$, —S(O)$_2R^b$, —O$R^c$, —N$R^{d1}R^{d2}$, and —OP(O)(O$R^c$)$_2$, wherein $C_1$-$C_6$-alkyl, $C_3$-$C_{10}$-heterocycloalkyl and $C_3$-$C_{10}$-cycloalkyl of $R^4$, $R^5$, $R^6$, and $R^7$, are optionally substituted one or more times with $R^8$, and wherein $C_1$-$C_6$-alkyl, $C_3$-$C_{10}$-heterocycloalkyl and $C_3$-$C_{10}$-cycloalkyl of $R^8$, are optionally substituted once with $R^8$;

$R^a$ is selected from the group consisting of hydrogen and $C_1$-$C_6$-alkyl;

$R^b$ is selected from the group consisting of hydroxyl, —O$R^c$, —S$R^c$, —N$R^{d1}R^{d2}$, aryl and $C_1$-$C_6$-alkyl;

$R^c$ is selected from the group consisting of hydrogen, —C(O)$R^b$, $C_1$-$C_6$-alkyl, $C_1$-$C_6$-haloalkyl, $C_3$-$C_{10}$-cycloalkyl, and $C_3$-$C_{10}$-heterocycloalkyl, wherein $C_1$-$C_6$-alkyl, $C_1$-$C_6$-haloalkyl, $C_3$-$C_{10}$-cycloalkyl, and $C_3$-$C_{10}$-heterocycloalkyl are optionally substituted one or more times, in the same way or differently, with hydroxyl, halogen, aryl, or —N$R^{d1}R^{d2}$, and wherein $C_1$-$C_6$-alkyl, $C_1$-$C_6$-haloalkyl, $C_3$-$C_{10}$-cycloalkyl, and $C_3$-$C_{10}$-heterocycloalkyl are optionally substituted once with —O$R^c$, or —OP(O)(O$R^c$)$_2$;

$R^{d1}$, $R^{d2}$ independently from each other are selected from the group consisting of hydrogen, $C_1$-$C_6$-alkyl, $C_3$-$C_{10}$-cycloalkyl, $C_3$-$C_{10}$-heterocycloalkyl, aryl, heteroaryl, —C(O)$R^c$, —S(O)$_2R^b$, and —C(O)N$R^{d1}R^{d2}$, wherein $C_1$-$C_6$-alkyl, $C_3$-$C_{10}$-cycloalkyl, and $C_3$-$C_{10}$-heterocycloalkyl are optionally substituted one or more times, in the same way or differently, with halogen, hydroxy or an —O$R^c$, —C(O)$R^b$, —S(O)$_2R^b$, or —OP(O)(O$R^c$)$_2$ group, and wherein $C_1$-$C_6$-alkyl, $C_3$-$C_{10}$-cycloalkyl, and $C_3$-$C_{10}$-heterocycloalkyl are optionally substituted once with an —N$R^{d1}R^{d2}$ group; or $R^{d1}$ and $R^{d2}$ together with the nitrogen atom to which they are attached, form a 3 to 10 membered heterocycloalkyl ring, which ring is optionally interrupted one or more times, the same way or differently, by NH, N$R^{d1}$, oxygen or sulphur, and is optionally interrupted one or more times, the same way or differently, with a —C(O)—, —S(O)—, and/or —S(O)$_2$— group, and optionally contains one or more double bonds;

A is selected from the group consisting of —C(O)—, —C(S)—, —C(=N$R^a$)—, —C(O)N$R^a$—, —C(=N$R^a$)N$R^a$—, —S(O)$_2$—, —S(O)(=N$R^a$)—, —S(=N$R^a$)$_2$—, —C(S)N$R^a$—, —C(O)C(O)—, —C(O)C(O)N$R^a$—, —C(O)N$R^aC$(O)—, —C(S)N$R^aC$(O)—, and —C(O)N$R^aC$(S)—;

B is a bond or a group selected from the group consisting of $C_1$-$C_6$-alkylene, $C_3$-$C_{10}$-cycloalkylene, and $C_3$-$C_{10}$-heterocycloalkylene;

D, E are, independently from each other, arylene or heteroarylene; and q represents an integer of 0, 1, or 2;

or a salt or an N-oxide thereof, wherein, when one or more of $R^a$, $R^b$, $R^c$, $R^{d1}$, $R^{d2}$ and $R^8$ are present in one position in the molecule as well as in one or more further positions in the molecule, said $R^a$, $R^b$, $R^c$, $R^{d1}$, $R^{d2}$ or $R^8$ have, independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

2. The compound according to claim 1, wherein:

$R^1$ represents —C(O)$R^b$ or is selected from the group consisting of $C_1$-$C_6$-alkyl, $C_2$-$C_6$-alkenyl, $C_2$-$C_6$-alkynyl, $C_3$-$C_{10}$-cycloalkyl, and $C_3$-$C_{10}$-heterocycloalkyl, which are unsubstituted or substituted one or more times, independently from each other, with $R^6$;

$R^2$ represents a $C_3$-$C_{10}$-cycloalkyl optionally substituted with $R^7$;

$R^3$ is selected from the group consisting of hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen, and cyano;

$R^4$, $R^5$, $R^6$, $R^7$, $R^8$ independently from each other, are selected from the group consisting of hydrogen, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)$R^b$, —S(O)$_2R^b$, —O$R^c$, —N$R^{d1}R^{d2}$, and —OP(O)(O$R^c$)$_2$, wherein $C_1$-$C_6$-alkyl,

135

$C_3$-$C_{10}$-heterocycloalkyl and $C_3$-$C_{10}$-cycloalkyl of $R^4$, $R^5$, $R^6$, and $R^7$, are optionally substituted one or more times with $R^8$, and wherein $C_1$-$C_6$-alkyl, $C_3$-$C_{10}$-heterocycloalkyl and $C_3$-$C_{10}$-cycloalkyl of $R^8$, are optionally substituted once with $R^8$;

$R^a$ is selected from the group consisting of hydrogen and $C_1$-$C_6$-alkyl;

$R^b$ is selected from the group consisting of hydroxyl, —$OR^c$, —$SR^c$, —$NR^{d1}R^{d2}$, aryl and $C_1$-$C_6$-alkyl;

$R^c$ is selected from the group consisting of hydrogen, —$C(O)R^b$, $C_1$-$C_6$-alkyl, $C_1$-$C_6$-haloalkyl, $C_3$-$C_{10}$-cycloalkyl, and $C_3$-$C_{10}$-heterocycloalkyl, wherein $C_1$-$C_6$-alkyl, $C_1$-$C_6$-haloalkyl, $C_3$-$C_{10}$-cycloalkyl, and $C_3$-$C_{10}$-heterocycloalkyl are optionally substituted one or more times, in the same way or differently, with hydroxyl, halogen, aryl, or —$NR^{d1}R^{d2}$, and wherein $C_1$-$C_6$-alkyl, $C_1$-$C_6$-haloalkyl, $C_3$-$C_{10}$-cycloalkyl, and $C_3$-$C_{10}$-heterocycloalkyl are optionally substituted once with —$OR^c$, or —$OP(O)(OR^c)_2$;

$R^{d1}$, $R^{d2}$ independently from each other are selected from the group consisting of hydrogen, $C_1$-$C_6$-alkyl, $C_3$-$C_{10}$-cycloalkyl, $C_3$-$C_{10}$-heterocycloalkyl, aryl, heteroaryl, —$C(O)R^c$, —$S(O)_2R^b$, and —$C(O)NR^{d1}R^{d2}$, wherein $C_1$-$C_6$-alkyl, $C_3$-$C_{10}$-cycloalkyl, and $C_3$-$C_{10}$-heterocycloalkyl are optionally substituted one or more times, in the same way or differently, with halogen, hydroxy or an —$OR^c$, —$C(O)R^b$, —$S(O)_2R^b$, or —$OP(O)(OR^c)_2$ group, and wherein $C_1$-$C_6$-alkyl, $C_3$-$C_{10}$-cycloalkyl, and $C_3$-$C_{10}$-heterocycloalkyl are optionally substituted once with an —$NR^{d1}R^{d2}$ group; or $R^{d1}$ and $R^{d2}$ together with the nitrogen atom to which they are attached, form a 3 to 10 membered heterocycloalkyl ring, which ring is optionally interrupted one or more times, the same way or differently, by NH, $NR^{d1}$, oxygen or sulphur, and is optionally interrupted one or more times, the same way or differently, with a —$C(O)$—, —$S(O)$—, and/or —$S(O)_2$— group, and optionally contains one or more double bonds;

A is selected from the group consisting of —$C(O)$—, —$C(O)NR^a$—, —$S(O)_2$—, —$C(S)NR^a$—, —$C(O)C(O)$—, —$C(O)C(O)NR^a$—, —$C(O)NR^aC(O)$—, —$C(S)NR^aC(O)$—, and —$C(O)NR^aC(S)$—;

B is a bond or a group selected from the group consisting of $C_1$-$C_6$-alkylene, $C_3$-$C_{10}$-cycloalkylene, and $C_3$-$C_{10}$-heterocycloalkylene;

D is phenylene;

E is phenylene or 5- or 6-membered heteroarylene; and q represents an integer of 0 or 1;

wherein, when one or more of $R^a$, $R^b$, $R^{d1}$, $R^{d2}$ and $R^8$ are present in one position in the molecule as well as in one or more further positions in the molecule, said $R^a$, $R^b$, $R^c$, $R^{d1}$, $R^{d2}$ or $R^8$ have, independently from each other, the same meanings as defined above in said first position in the molecule and in said second or further positions in the molecule, it being possible for the two or more occurrences of $R^a$, $R^b$, $R^c$, $R^{d1}$, $R^{d2}$, or $R^8$ within a single molecule to be identical or different.

3. The compound according to claim 1, wherein:

$R^1$ represents —$C(O)R^b$ or is selected from the group consisting of $C_1$-$C_6$-alkyl, $C_3$-$C_{10}$-cycloalkyl, and $C_3$-$C_{10}$-heterocycloalkyl, which are unsubstituted or substituted one or more times, independently from each other, with $R^6$;

$R^2$ represents a $C_3$-$C_{10}$-cycloalkyl optionally substituted with $R^7$;

136

$R^3$ is selected from the group consisting of hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen, and cyano;

$R^4$, $R^5$, $R^6$, $R^7$, $R^8$ independently from each other, are selected from the group consisting of hydrogen, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —$C(O)R^b$, —$S(O)_2R^b$, —$OR^c$, —$NR^{d1}R^{d2}$, and —$OP(O)(OR^c)_2$, wherein $C_1$-$C_6$-alkyl, $C_3$-$C_{10}$-heterocycloalkyl and $C_3$-$C_{10}$-cycloalkyl of $R^4$, $R^5$, $R^6$, and $R^7$, are optionally substituted one or more times with $R^8$, and wherein $C_1$-$C_6$-alkyl, $C_3$-$C_{10}$-heterocycloalkyl and $C_3$-$C_{10}$-cycloalkyl of $R^8$, are optionally substituted once with $R^8$;

$R^a$ is selected from the group consisting of hydrogen and $C_1$-$C_6$-alkyl;

$R^b$ is selected from the group consisting of hydroxyl, —$OR^c$, —$SR^c$, —$NR^{d1}R^{d2}$, aryl and $C_1$-$C_6$-alkyl;

$R^c$ is selected from the group consisting of hydrogen, —$C(O)R^b$, $C_1$-$C_6$-alkyl, $C_1$-$C_6$-haloalkyl, $C_3$-$C_{10}$-cycloalkyl, and $C_3$-$C_{10}$-heterocycloalkyl, wherein $C_1$-$C_6$-alkyl, $C_1$-$C_6$-haloalkyl, $C_3$-$C_{10}$-cycloalkyl, and $C_3$-$C_{10}$-heterocycloalkyl are optionally substituted one or more times, in the same way or differently, with hydroxyl, halogen, aryl, or —$NR^{d1}R^{d2}$, and wherein $C_1$-$C_6$-alkyl, $C_1$-$C_6$-haloalkyl, $C_3$-$C_{10}$-cycloalkyl, and $C_3$-$C_{10}$-heterocycloalkyl are optionally substituted once with —$OR^c$, or —$OP(O)(OR^c)_2$;

$R^{d1}$, $R^{d2}$ independently from each other are selected from the group consisting of hydrogen, $C_1$-$C_6$-alkyl, $C_3$-$C_{10}$-cycloalkyl, $C_3$-$C_{10}$-heterocycloalkyl, aryl, heteroaryl, —$C(O)R^c$, —$S(O)_2R^b$, and —$C(O)NR^{d1}R^{d2}$, wherein $C_1$-$C_6$-alkyl, $C_3$-$C_{10}$-cycloalkyl, $C_3$-$C_{10}$-heterocycloalkyl are optionally substituted one or more times, in the same way or differently, with halogen, hydroxy or an —$OR^c$, —$C(O)R^b$, —$S(O)_2R^b$, or —$OP(O)(OR^c)_2$ group, and wherein $C_1$-$C_6$-alkyl, $C_3$-$C_{10}$-cycloalkyl, and $C_3$-$C_{10}$-heterocycloalkyl are optionally substituted once with an —$NR^{d1}R^{d2}$ group; or $R^{d1}$ and $R^{d2}$ together with the nitrogen atom to which they are attached, form a 3 to 10 membered heterocycloalkyl ring, which ring is optionally interrupted one or more times, the same way or differently, by NH, $NR^{d1}$, oxygen or sulphur, and is optionally interrupted one or more times, the same way or differently, with a —$C(O)$—, —$S(O)$—, and/or —$S(O)_2$— group, and optionally contains one or more double bonds;

A is selected from the group consisting of —$C(O)$—, —$C(O)NR^a$—, and —$S(O)_2$—;

B is a bond or a group selected from the group consisting of $C_1$-$C_6$-alkylene, and $C_3$-$C_{10}$-cycloalkylene;

D is para-phenylene;

E is phenylene or 5- or 6-membered heteroarylene; and q represents an integer of 0 or 1; wherein, when one or more of $R^a$, $R^b$, $R^c$, $R^{d1}$, $R^{d2}$ and $R^8$ are present in one position in the molecule as well as in one or more further positions in the molecule, said $R^a$, $R^b$, $R^c$, $R^{d1}$, $R^{d2}$ or $R^8$ have, independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

4. The compound according to claim 1, wherein:

$R^1$ represents —$C(O)R^b$ or is selected from the group consisting of $C_1$-$C_6$-alkyl, $C_3$-$C_6$-cycloalkyl, and $C_3$-$C_6$- heterocycloalkyl, which are unsubstituted or substituted one or more times, independently from each other, with $R^6$;

$R^2$ represents a $C_3$-$C_6$-cycloalkyl optionally substituted with $R^7$;

$R^3$ is selected from the group consisting of hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen, and cyano;

$R^4$ is selected from the group consisting of hydrogen, $C_1$-$C_6$-alkyl, $C_1$-$C_6$-haloalkyl, $C_1$-$C_6$-haloalkoxy, hydroxy, amino, halogen, cyano, nitro, and —$OR^c$, wherein $C_1$-$C_6$-alkyl is optionally substituted one or more times with $R^8$;

$R^5$ is selected from the group consisting of hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, cyano, nitro, —$C(O)R^b$, —$S(O)_2R^b$, —$OR^c$, and —$NR^{d1}R^{d2}$, wherein $C_1$-$C_6$-alkyl and $C_3$-$C_6$-heterocycloalkyl are optionally substituted one or more times with $R^8$;

$R^6$ is selected from the group consisting of hydrogen, $C_3$-$C_6$-heterocycloalkyl, $C_1$-$C_6$-haloalkoxy, aryl, hydroxy, amino, cyano, —$C(O)R^b$, —$S(O)_2R^b$, —$OR^c$, and —$NR^{d1}R^{d2}$, wherein $C_3$-$C_6$-heterocycloalkyl is optionally substituted one or more times with $R^8$;

$R^7$ is selected from the group consisting of hydrogen, $C_1$-$C_6$-alkyl, $C_3$-$C_6$-heterocycloalkyl, $C_1$-$C_6$-haloalkyl, $C_1$-$C_6$-haloalkoxy, aryl, hydroxy, amino, cyano, —$C(O)R^b$, —$S(O)_2R^b$, —$OR^c$, and —$NR^{d1}R^{d2}$, wherein $C_1$-$C_6$-alkyl and $C_3$-$C_6$-heterocycloalkyl are optionally substituted one or more times with $R^8$;

$R^8$ is selected from the group consisting of $C_1$-$C_6$-haloalkoxy, hydroxy, amino, cyano, halogen, —$C(O)R^b$, —$S(O)_2R^b$, —$OR^c$, and —$NR^{d1}R^{d2}$;

$R^a$ is hydrogen;

$R^b$ is selected from the group consisting of —$OR^c$, —$NR^{d1}R^{d2}$, and $C_1$-$C_6$-alkyl;

$R^c$ is selected from the group consisting of hydrogen, $C_1$-$C_6$-alkyl, $C_3$-$C_6$-cycloalkyl, and $C_3$-$C_6$-heterocycloalkyl, wherein $C_1$-$C_6$-alkyl, $C_3$-$C_6$-cycloalkyl, and $C_3$-$C_6$-heterocycloalkyl are optionally substituted one or more times with —$NR^{d1}R^{d2}$, and wherein $C_1$-$C_6$-alkyl, $C_3$-$C_6$-cycloalkyl, and $C_3$-$C_6$-heterocycloalkyl are optionally substituted once with —$OR^c$;

$R^{d1}$, $R^{d2}$ independently from each other are selected from the group consisting of hydrogen, $C_1$-$C_6$-alkyl, $C_3$-$C_6$-cycloalkyl, or for a $C(O)R^c$ and —$C(O)NR^{d1}R^{d2}$, wherein $C_1$-$C_6$-alkyl and $C_3$-$C_6$-cycloalkyl are optionally substituted one or more times, in the same way or differently, with an —$OR^c$, or —$C(O)R^b$ group, and wherein $C_1$-$C_6$-alkyl and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, which ring is optionally interrupted one or more times, the same way or differently, by NH, $NR^{d1}$, or oxygen;

A is selected from the group consisting of —C(O)—, —$C(O)NR^a$—, and —$S(O)_2$—;

B is a bond or a group selected from the group consisting of $C_1$-$C_3$-alkylene, and $C_3$-cycloalkylene;

D is para-phenylene;

E is phenylene;

q represents an integer of 0;

wherein, when one or more of $R^a$, $R^b$, $R^c$, $R^{d1}$, $R^{d2}$ and $R^8$ are present in one position in the molecule as well as in one or more further positions in the molecule, said $R^a$, $R^b$, $R^c$, $R^{d1}$, $R^{d2}$ or $R^8$ have, independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

5. The compound according to claim 1, wherein:

$R^1$ represents —$C(O)R^b$ or is selected from the preferably consisting of $C_1$-$C_6$-alkyl, $C_3$-$C_6$-cycloalkyl, and $C_3$-$C_6$-heterocycloalkyl, which are unsubstituted or substituted one or more times, independently from each other, with $R^6$;

$R^2$ represents a $C_3$-$C_6$-cycloalkyl optionally substituted with $R^7$;

$R^3$ is selected from the group consisting of hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen, and cyano;

$R^4$ is selected from the group consisting of hydrogen, $C_1$-$C_6$-alkyl, $C_1$-$C_6$-haloalkyl, $C_1$-$C_6$-haloalkoxy, hydroxy, amino, halogen, cyano, nitro, and —$OR^c$, wherein $C_1$-$C_6$-alkyl is optionally substituted one or more times with $R^8$;

$R^5$ is selected from the group consisting of hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, cyano, nitro, —$C(O)R^b$, —$S(O)_2R^b$, —$OR^c$, and —$NR^{d1}R^{d2}$, wherein $C_1$-$C_6$-alkyl and $C_3$-$C_6$-heterocycloalkyl are optionally substituted one or more times with $R^8$;

$R^6$ is selected from the group consisting of hydrogen, $C_3$-$C_6$-heterocycloalkyl, $C_1$-$C_6$-haloalkoxy, hydroxy, amino, cyano, —$C(O)R^b$, —$S(O)_2R^b$, —$OR^c$, and —$NR^{d1}R^{d2}$, wherein $C_3$-$C_6$-heterocycloalkyl is optionally substituted one or more times with $R^8$;

$R^7$ is selected from the group consisting of hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, cyano, —$C(O)R^b$, —$S(O)_2R^b$, —$OR^c$, and —$NR^{d1}R^{d2}$, wherein $C_1$-$C_6$-alkyl and $C_3$-$C_6$-heterocycloalkyl are optionally substituted one or more times with $R^8$;

$R^8$ is selected from the group consisting of $C_1$-$C_6$-haloalkoxy, hydroxy, amino, cyano, halogen, —$C(O)R^b$, —$S(O)_2R^b$, —$OR^c$, and —$NR^{d1}R^{d2}$;

$R^a$ is hydrogen;

$R^b$ is selected from the group consisting of —$OR^c$, —$NR^{d1}R^{d2}$, and $C_1$-$C_6$-alkyl;

$R^c$ is selected from the group consisting of hydrogen, $C_1$-$C_6$-alkyl, $C_3$-$C_6$-cycloalkyl, and $C_3$-$C_6$-heterocycloalkyl, wherein $C_1$-$C_6$-alkyl, $C_3$-$C_6$-cycloalkyl, and $C_3$-$C_6$-heterocycloalkyl are optionally substituted one or more times with —$NR^{d1}R^{d2}$, and wherein $C_1$-$C_6$-alkyl, $C_3$-$C_6$-cycloalkyl, and $C_3$-$C_6$-heterocycloalkyl are optionally substituted once with —$OR^c$;

$R^{d1}$, $R^{d2}$ independently from each other are selected from the group consisting of hydrogen, $C_1$-$C_6$-alkyl, $C_3$-$C_6$-cycloalkyl, $C(O)R^c$ of and —$C(O)NR^{d1}R^{d2}$ group, wherein $C_1$-$C_6$-alkyl and $C_3$-$C_6$-cycloalkyl are optionally substituted one or more times, in the same way or differently, with an —$OR^c$ or —$C(O)R^b$ group, and wherein $C_1$-$C_6$-alkyl and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, which ring is optionally interrupted one or more times, the same way or differently, by NH, $NR^{d1}$, or oxygen;

A is —$C(O)NR^a$—;

B is a bond or a group selected from the group consisting of $C_1$-$C_3$-alkylene, and $C_3$-cycloalkylene;

D is para-phenylene;
E is phenylene;
q represents an integer of 0;
wherein, when one or more of $R^a$, $R^b$, $R^c$, $R^{d1}$, $R^{d2}$ and $R^8$ are present in one position in the molecule as well as in one or more further positions in the molecule, said $R^a$, $R^b$, $R^c$, $R^{d1}$, $R^{d2}$ or $R^8$ have, independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

6. The compound according to claim 1, wherein:
$R^1$ represents —C(O)$R^b$ or is selected from the group consisting of $C_1$-$C_6$-alkyl, $C_3$-$C_6$-cycloalkyl, and $C_3$-$C_6$-heterocycloalkyl, which are unsubstituted or substituted one or more times, independently from each other, with $R^6$;
$R^2$ represents cyclopropyl;
$R^3$ is selected from the group consisting of hydrogen, methyl, and fluoro;
$R^4$ is selected from the group consisting of hydrogen, $C_1$-$C_6$-alkyl, $C_1$-$C_6$-haloalkyl, $C_1$-$C_6$-haloalkoxy, hydroxy, amino, cyano, halogen, and —OR$^c$, wherein $C_1$-$C_6$-alkyl is optionally substituted one or more times with $R^8$;
$R^5$ is selected from the group consisting of hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, cyano, halogen, —C(O)$R^b$, —S(O)$_2R^b$, —OR$^c$, and —NR$^{d1}R^{d2}$, wherein $C_1$-$C_6$-alkyl and $C_3$-$C_6$-heterocycloalkyl are optionally substituted one or more times with $R^8$;
$R^6$ is selected from the group consisting of hydrogen, $C_3$-$C_6$-heterocycloalkyl, $C_1$-$C_6$-haloalkoxy, hydroxy, amino, cyano, —C(O)$R^b$, —S(O)$_2R^b$, —OR$^c$, and —NR$^{d1}R^{d2}$, wherein $C_3$-$C_6$-heterocycloalkyl is optionally substituted one or more times with $R^8$;
$R^8$ is selected from the group consisting of $C_1$-$C_6$-haloalkoxy, hydroxy, amino, cyano, halogen, —C(O)$R^b$, —S(O)$_2R^b$, —OR$^c$, and —NR$^{d1}R^{d2}$;
$R^a$ is hydrogen;
$R^b$ is selected from the group consisting of —OR$^c$, and —NR$^{d1}R^{d2}$;
$R^c$ is selected from the group consisting of hydrogen, $C_1$-$C_6$-alkyl, $C_3$-$C_6$-cycloalkyl, and $C_3$-$C_6$-heterocycloalkyl, wherein $C_1$-$C_6$-alkyl, $C_3$-$C_6$-cycloalkyl, and $C_3$-$C_6$-heterocycloalkyl are optionally substituted one or more times with —NR$^{d1}R^{d2}$, and wherein $C_1$-$C_6$-alkyl, $C_3$-$C_6$-cycloalkyl, and $C_3$-$C_6$-heterocycloalkyl are optionally substituted once with —OR$^c$;
$R^{d1}$, $R^{d2}$ independently from each other are selected from the group consisting of hydrogen, $C_1$-$C_6$-alkyl, $C_3$-$C_6$-cycloalkyl, or for a C(O)$R^c$ and —C(O)NR$^{d1}R^{d2}$ group, wherein $C_1$-$C_6$-alkyl and $C_3$-$C_6$-cycloalkyl are optionally substituted one or more times, in the same way or differently, with an —OR$^c$ or —C(O)$R^b$ group, and wherein $C_1$-$C_6$-alkyl and $C_3$-$C_6$-cycloalkyl are optionally substituted once with an —NR$^{d1}R^{d2}$ group; or,
$R^{d1}$ and $R^{d2}$ together with the nitrogen atom to which they are attached, form a 3 to 6 membered heterocycloalkyl ring, which ring is optionally interrupted one or more times, the same way or differently, by NH, NR$^{d1}$, or oxygen;
A is —C(O)NR$^a$—;
B is a bond or a group selected from the group consisting of $C_1$-$C_3$-alkylene, and $C_3$-cycloalkylene;
D is para-phenylene;
E is phenylene;
q represents an integer of 0;
wherein, when one or more of $R^a$, $R^b$, $R^c$, $R^{d1}$, $R^{d2}$ and $R^8$ are present in one position in the molecule as well as in one or more further positions in the molecule, said $R^a$, $R^b$, $R^c$, $R^{d1}$, $R^{d2}$ or $R^8$ have, independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

7. The compound according to claim 1, wherein:
$R^1$ is $C_1$-$C_6$-alkyl;
$R^2$ represents a $C_3$-$C_6$-cycloalkyl optionally substituted with $R^7$;
$R^3$ is selected from the group consisting of hydrogen, methyl, and fluoro;
$R^4$ is selected from the group consisting of hydrogen, $C_1$-$C_6$-alkyl, $C_1$-$C_6$-haloalkyl, $C_1$-$C_6$-haloalkoxy, hydroxy, amino, cyano, halogen, and —OR$^c$, wherein $C_1$-$C_6$-alkyl is optionally substituted one or more times with $R^8$;
$R^5$ is selected from the group consisting of hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, cyano, halogen, —C(O)$R^b$, —S(O)$_2R^b$, —OR$^c$, and —NR$^{d1}R^{d2}$, wherein $C_1$-$C_6$-alkyl and $C_3$-$C_6$-heterocycloalkyl are optionally substituted one or more times with $R^8$;
$R^7$ is selected from the group consisting of hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, cyano, —C(O)$R^b$, —S(O)$_2R^b$, —OR$^c$, and —NR$^{d1}R^{d2}$, wherein $C_1$-$C_6$-alkyl and $C_3$-$C_6$-heterocycloalkyl are optionally substituted one or more times with $R^8$;
$R^8$ is selected from the group consisting of $C_1$-$C_6$-haloalkoxy, hydroxy, amino, cyano, halogen, —C(O)$R^b$, —S(O)$_2R^b$, —OR$^c$, and —NR$^{d1}R^{d2}$;
$R^a$ is hydrogen;
$R^b$ is selected from the group consisting of —OR$^c$, and —NR$^{d1}R^{d2}$;
$R^c$ is selected from the group consisting of hydrogen, $C_1$-$C_6$-alkyl, $C_3$-$C_6$-cycloalkyl, and $C_3$-$C_6$-heterocycloalkyl, wherein $C_1$-$C_6$-alkyl, $C_3$-$C_6$-cycloalkyl, and $C_3$-$C_6$-heterocycloalkyl are optionally substituted one or more times with —NR$^{d1}R^{d2}$, and wherein $C_1$-$C_6$-alkyl, $C_3$-$C_6$-cycloalkyl, and $C_3$-$C_6$-heterocycloalkyl are optionally substituted once with —OR$^c$;
$R^{d1}$, $R^{d2}$ independently from each other are selected from the group consisting of hydrogen, $C_1$-$C_6$-alkyl, $C_3$-$C_6$-cycloalkyl, —C(O)$R^c$ and —C(O)NR$^{d1}R^{d2}$ group, wherein $C_1$-$C_6$-alkyl and $C_3$-$C_6$-cycloalkyl are optionally substituted one or more times, in the same way or differently, with an —OR$^c$ or —C(O)$R^b$ group, and wherein $C_1$-$C_6$-alkyl and $C_3$-$C_6$-cycloalkyl are optionally substituted once with an —NR$^{d1}R^{d2}$ group; or,
$R^{d1}$ and $R^{d2}$ together with the nitrogen atom to which they are attached, form a 3 to 6 membered heterocycloalkyl ring, which ring is optionally interrupted one or more times, the same way or differently, by NH, NR$^{d1}$, or oxygen;
A is —C(O)NR$^a$—;
B is a bond or a group selected from the group consisting of $C_1$-$C_3$-alkylene, and $C_3$-cycloalkylene;
D is para-phenylene;
E is phenylene;
q represents an integer of 0;

wherein, when one or more of $R^a$, $R^b$, $R^c$, $R^{d1}$, $R^{d2}$ and $R^8$ are present in one position in the molecule as well as in one or more further positions in the molecule, said $R^a$, $R^b$, $R^c$, $R^{d1}$, $R^{d2}$ or $R^8$ have, independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

8. The compound according to claim 1, wherein:
$R^1$ is $C_1$-$C_3$-alkyl;
$R^2$ is cyclopropyl;
$R^3$ is selected from the group consisting of hydrogen, methyl, and fluoro;
$R^4$ is selected from the group consisting of hydrogen, halogen, $C_1$-$C_3$-alkyl, of and $C_1$-$C_3$-haloalkyl;
$R^5$ is selected from the group consisting of hydrogen, $C_1$-$C_3$-alkyl, $C_1$-$C_3$-haloalkyl, $C_1$-$C_3$-haloalkoxy, halogen, —$OR^c$, and —$NR^{d1}R^{d2}$, wherein $C_1$-$C_3$-alkyl is optionally substituted by $R^8$;
$R^8$ is selected from the group consisting of —$OR^c$, and —$NR^{d1}R^{d2}$;
$R^a$ is hydrogen;
$R^c$ is selected from the group consisting of hydrogen, and $C_1$-$C_3$-alkyl, wherein $C_1$-$C_3$-alkyl is optionally substituted one or more times with —$NR^{d1}R^{d2}$, and wherein $C_1$-$C_3$-alkyl is optionally substituted once with —$OR^c$;
$R^{d1}$, $R^{d2}$ independently from each other are selected from the group consisting of hydrogen, and $C_1$-$C_3$-alkyl, wherein $C_1$-$C_3$-alkyl is optionally substituted one or more times with an —$OR^c$ group, and wherein $C_1$-$C_3$-alkyl is optionally substituted once with an —$NR^{d1}R^{d2}$ group; or,
$R^{d1}$ and $R^{d2}$ together with the nitrogen atom to which they are attached, form a 6 membered heterocycloalkyl ring, which ring is optionally interrupted one time, by NH, $NR^{d1}$, or oxygen;
A is —$C(O)NR^a$—;
B is a bond;
D is para-phenylene;
E is phenylene;
q represents an integer of 0;
wherein, when one or more of $R^a$, $R^b$, $R^c$, $R^{d1}$ and $R^8$ are present in one position in the molecule as well as in one or more further positions in the molecule, said $R^a$, $R^b$, $R^c$, $R^{d1}$ or $R^{d2}$ have, independently from each other, the same meanings as defined above in said first position in the molecule and in said second or further positions in the molecule, it being possible for the two or more occurrences of $R^a$, $R^b$, $R^c$, $R^{d1}$ or $R^{d2}$ within a single molecule to be identical or different.

9. The compound according to claim 1, wherein:
$R^1$ represents —$C(O)R^b$ or is selected from the group consisting of $C_1$-$C_6$-alkyl, $C_3$-$C_6$-cycloalkyl, and $C_3$-$C_6$-heterocycloalkyl, which are unsubstituted or substituted one or more times, independently from each other, with $R^6$;
$R^2$ represents a $C_3$-$C_6$-cycloalkyl optionally substituted with $R^7$;
$R^3$ is selected from the group consisting of hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen, and cyano;
$R^4$ is selected from the group consisting of hydrogen, $C_1$-$C_6$-alkyl, $C_1$-$C_6$-haloalkyl, $C_1$-$C_6$-haloalkoxy, hydroxy, amino, cyano, nitro, halogen, and —$OR^c$, wherein $C_1$-$C_6$-alkyl is optionally substituted one or more times with $R^8$;
$R^5$ is selected from the group consisting of hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, cyano, nitro, halogen, —$C(O)R^b$, —$S(O)_2R^b$, —$OR^c$, and —$NR^{d1}R^{d2}$, wherein $C_1$-$C_6$-alkyl and $C_3$-$C_6$-heterocycloalkyl are optionally substituted one or more times with $R^8$;
$R^6$ is selected from the group consisting of hydrogen, $C_3$-$C_6$-heterocycloalkyl, $C_1$-$C_6$-haloalkoxy, hydroxy, amino, cyano, —$C(O)R^b$, —$S(O)_2R^b$, —$OR^c$, and —$NR^{d1}R^{d2}$, wherein $C_3$-$C_6$-heterocycloalkyl is optionally substituted one or more times with $R^8$;
$R^7$ is selected from the group consisting of hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, cyano, —$C(O)R^b$, —$S(O)_2R^b$, —$OR^c$, and —$NR^{d1}R^{d2}$, wherein $C_1$-$C_6$-alkyl and $C_3$-$C_6$-heterocycloalkyl are optionally substituted one or more times with $R^8$;
$R^8$ is selected from the group consisting of $C_1$-$C_6$-haloalkoxy, hydroxy, amino, cyano, halogen, —$C(O)R^b$, —$S(O)_2R^b$, —$OR^c$, and —$NR^{d1}R^{d2}$;
$R^a$ is hydrogen;
$R^b$ is selected from the group consisting of —$OR^c$, —$NR^{d1}R^{d2}$, and $C_1$-$C_6$-alkyl;
$R^c$ is selected from the group consisting of hydrogen, $C_1$-$C_6$-alkyl, $C_3$-$C_6$-cycloalkyl, and $C_3$-$C_6$-heterocycloalkyl, wherein $C_1$-$C_6$-alkyl, $C_3$-$C_6$-cycloalkyl, and $C_3$-$C_6$-heterocycloalkyl are optionally substituted one or more times with —$NR^{d1}R^{d2}$, and wherein $C_1$-$C_6$-alkyl, $C_3$-$C_6$-cycloalkyl, and $C_3$-$C_6$-heterocycloalkyl are optionally substituted once with —$OR^c$;
$R^{d1}$, $R^{d2}$ independently from each other are selected from the group consisting of hydrogen, $C_1$-$C_6$-alkyl, $C_3$-$C_6$-cycloalkyl, $C(O)R^c$ of and —$C(O)NR^{d1}R^{d2}$ group, wherein $C_1$-$C_6$-alkyl and $C_3$-$C_6$-cycloalkyl are optionally substituted one or more times, the same way or differently, with an —$OR^c$ or —$C(O)R^b$ group, and wherein $C_1$-$C_6$-alkyl and $C_3$-$C_6$-cycloalkyl are optionally substituted once with an —$NR^{d1}R^{d2}$ group; or,
$R^{d1}$ and $R^{d2}$ together with the nitrogen atom to which they are attached, form a 3 to 6 membered heterocycloalkyl ring, which ring is optionally interrupted one or more times, the same way or differently, by NH, $NR^{d1}$, or oxygen;
A is —$C(O)$— or —$S(O)_2$—;
B is a bond or a group selected from the group consisting of $C_1$-$C_3$-alkylene, and $C_3$-cycloalkylene;
D is para-phenylene;
E is phenylene;
q represents an integer of 0;
wherein, when one or more of $R^a$, $R^b$, $R^c$, $R^{d1}$, $R^{d2}$ and $R^8$ are present in one position in the molecule as well as in one or more further positions in the molecule, said $R^a$, $R^b$, $R^c$, $R^{d1}$, $R^{d2}$ or $R^8$ have, independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

10. The compound according to claim 1, wherein:
$R^1$ represents —$C(O)R^b$ or is selected from the group consisting of $C_1$-$C_6$-alkyl, $C_3$-$C_6$-cycloalkyl, and $C_3$-$C_6$-heterocycloalkyl, which are unsubstituted or substituted one or more times, independently from each other, with $R^6$;
$R^2$ represents cyclopropyl;
$R^3$ is selected from the group consisting of hydrogen, methyl, and fluoro;

$R^4$ is selected from the group consisting of hydrogen, $C_1$-$C_6$-alkyl, $C_1$-$C_6$-haloalkyl, $C_1$-$C_6$-haloalkoxy, hydroxy, amino, cyano, halogen, and —$OR^c$, wherein $C_1$-$C_6$-alkyl is optionally substituted one or more times with $R^8$;

$R^5$ is selected from the group consisting of hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, cyano, halogen, —$C(O)R^b$, —$S(O)_2R^b$, —$OR^c$, and —$NR^{d1}R^{d2}$, wherein $C_1$-$C_6$-alkyl and $C_3$-$C_6$-heterocycloalkyl are optionally substituted one or more times with $R^8$;

$R^6$ is selected from the group consisting of hydrogen, $C_3$-$C_6$-heterocycloalkyl, $C_1$-$C_6$-haloalkoxy, hydroxy, amino, cyano, —$C(O)R^b$, —$S(O)_2R^b$, —$OR^c$, and —$NR^{d1}R^{d2}$, wherein $C_3$-$C_6$-heterocycloalkyl is optionally substituted one or more times with $R^8$;

$R^8$ is selected from the group consisting of $C_1$-$C_6$-haloalkoxy, hydroxy, amino, cyano, halogen, —$C(O)R^b$, —$S(O)_2R^b$, —$OR^c$, and —$NR^{d1}R^{d2}$;

$R^a$ is hydrogen;

$R^b$ is selected from the group consisting of —$OR^c$, and —$NR^{d1}R^{d2}$;

$R^c$ is selected from the group consisting of hydrogen, $C_1$-$C_6$ alkyl, $C_3$-$C_6$-cycloalkyl, and $C_3$-$C_6$-heterocycloalkyl, wherein $C_1$-$C_6$-alkyl, $C_3$-$C_6$-cycloalkyl, and $C_3$-$C_6$-heterocycloalkyl are optionally substituted one or more times with —$NR^{d1}R^{d2}$, and wherein $C_1$-$C_6$-alkyl, $C_3$-$C_6$-cycloalkyl, and $C_3$-$C_6$-heterocycloalkyl are optionally substituted once with —$OR^c$;

$R^{d1}$, $R^{d2}$ independently from each other are selected from the group consisting of hydrogen, $C_1$-$C_6$-alkyl, $C_3$-$C_6$-cycloalkyl, —$C(O)R^c$ and —$C(O)NR^{d1}R^{d2}$ group, wherein $C_1$-$C_6$-alkyl and $C_3$-$C_6$-cycloalkyl are optionally substituted one or more times, in the same way or differently, with an —$OR^c$ or —$C(O)R^b$ group, and wherein $C_1$-$C_6$-alkyl and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, which ring is optionally interrupted one or more times, the same way or differently, by NH, $NR^{d1}$, or oxygen;

A is —C(O)— or —$S(O)_2$—;

B is a bond or a group selected from the group consisting of $C_1$-$C_3$-alkylene, and $C_3$-cycloalkylene;

D is para-phenylene;

E is phenylene;

q represents an integer of 0;

wherein, when one or more of $R^a$, $R^b$, $R^c$, $R^{d1}$, $R^{d2}$ and $R^8$ are present in one position in the molecule as well as in one or more further positions in the molecule, said $R^a$, $R^b$, $R^c$, $R^{d1}$, $R^{d2}$ or $R^8$ have, independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

11. The compound according to claim 1, wherein:

$R^1$ is $C_1$-$C_6$-alkyl;

$R^2$ represents a $C_3$-$C_6$-cycloalkyl optionally substituted with $R^7$;

$R^3$ is selected from the group consisting of hydrogen, methyl, and fluoro;

$R^4$ is selected from the group consisting of hydrogen, $C_1$-$C_6$-alkyl, $C_1$-$C_6$-haloalkyl, $C_1$-$C_6$-haloalkoxy, hydroxy, amino, cyano, halogen, and —$OR^c$, wherein $C_1$-$C_6$-alkyl is optionally substituted one or more times with $R^8$;

$R^5$ is selected from the group consisting of hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, cyano, halogen, —$C(O)R^b$, $S(O)_2R^b$, —$OR^c$, and —$NR^{d1}R^{d2}$, wherein $C_1$-$C_6$-alkyl and $C_3$-$C_6$-heterocycloalkyl are optionally substituted one or more times with $R^8$;

$R^7$ is selected from the group consisting of hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, cyano, —$C(O)R^b$, —$S(O)_2R^b$, —$OR^c$, and —$NR^{d1}R^{d2}$, wherein $C_1$-$C_6$-alkyl and $C_3$-$C_6$-heterocycloalkyl are optionally substituted one or more times with $R^8$;

$R^8$ is selected from the group consisting of $C_1$-$C_6$-haloalkoxy, hydroxy, amino, cyano, halogen, —$C(O)R^b$, —$S(O)_2R^b$, —$OR^c$, and —$NR^{d1}R^{d2}$;

$R^a$ is hydrogen;

$R^b$ is selected from the group consisting of —$OR^c$, and —$NR^{d1}R^{d2}$;

$R^c$ is selected from the group consisting of hydrogen, $C_1$-$C_6$-alkyl, $C_3$-$C_6$-cycloalkyl, and $C_3$-$C_6$-heterocycloalkyl, wherein $C_1$-$C_6$-alkyl, $C_3$-$C_6$-cycloalkyl, and $C_3$-$C_6$-heterocycloalkyl are optionally substituted one or more times with —$NR^{d1}R^{d2}$, and wherein $C_1$-$C_6$-alkyl, $C_3$-$C_6$-cycloalkyl, and $C_3$-$C_6$-heterocycloalkyl are optionally substituted once with —$OR^c$;

$R^{d1}$, $R^{d2}$ independently from each other are selected from the group consisting of hydrogen, $C_1$-$C_6$-alkyl, $C_3$-$C_6$-cycloalkyl, —$C(O)R^c$ and —$C(O)NR^{d1}R^{d2}$ group, wherein $C_1$-$C_6$-alkyl and $C_3$-$C_6$-cycloalkyl are optionally substituted one or more times, in the same way or differently, with an —$OR^c$ or —$C(O)R^b$ group, and wherein $C_1$-$C_6$-alkyl and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, which ring is optionally interrupted one or more times, the same way or differently, by NH, $NR^{d1}$, or oxygen;

A is —C(O)— or —$S(O)_2$—;

B is a bond or a group selected from the group consisting of $C_1$-$C_3$-alkylene, and $C_3$-cycloalkylene;

D is para-phenylene;

E is phenylene;

q represents an integer of 0;

wherein, when one or more of $R^a$, $R^b$, $R^c$, $R^{d1}$, $R^{d2}$ and $R^8$ are present in one position in the molecule as well as in one or more further positions in the molecule, said $R^a$, $R^b$, $R^c$, $R^{d1}$, $R^{d2}$ or $R^8$ have, independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

12. The compound according to claim 1, wherein:

$R^1$ is $C_1$-$C_3$-alkyl;

$R^2$ is cyclopropyl;

$R^3$ is selected from the group consisting of hydrogen, methyl, and fluoro;

$R^4$ is selected from the group consisting of hydrogen, halogen, $C_1$-$C_3$-alkyl, and $C_1$-$C_3$-haloalkyl;

$R^5$ is selected from the group consisting of hydrogen, $C_1$-$C_3$-alkyl, $C_1$-$C_3$-haloalkyl, $C_1$-$C_3$-haloalkoxy, halogen, —$OR^c$, and —$NR^{d1}R^{d2}$, wherein $C_1$-$C_3$-alkyl is optionally substituted by $R^8$;

R⁸ is selected from the group consisting of —ORᶜ, and —NR^{d1}R^{d2};

Rᵃ is hydrogen;

Rᶜ is selected from the group consisting of hydrogen, and C₁-C₃-alkyl, wherein C₁-C₃-alkyl is optionally substituted one or more times with —NR^{d1}R^{d2}, and wherein C₁-C₃-alkyl is optionally substituted once with —ORᶜ;

R^{d1}, R^{d2} independently from each other are selected from the group consisting of hydrogen, and C₁-C₃-alkyl, wherein C₁-C₃-alkyl is optionally substituted one or more times with an —ORᶜ group, and wherein C₁-C₃-alkyl is optionally substituted once with an —NR^{d1}R^{d2} group; or, R^{d1} and R^{d2} together with the nitrogen atom to which they are attached, form a 6 membered heterocycloalkyl ring, which ring is optionally interrupted one time, by NH, NR^{d1}, or oxygen;

A is —C(O)—;

B is C₁-alkylene or C₃-cycloalkylene;

D is para-phenylene;

E is phenylene;

q represents an integer of 0;

wherein, when one or more of Rᵃ, Rᵇ, Rᶜ, R^{d1} and R⁸ are present in one position in the molecule as well as in one or more further positions in the molecule, said Rᵃ, Rᵇ, Rᶜ, R^{d1} or R^{d2} have, independently from each other, the same meanings as defined above in said first position in the molecule and in said second or further positions in the molecule, it being possible for the two or more occurrences of Rᵃ, Rᵇ, Rᶜ, R^{d1} or R^{d2} within a single molecule to be identical or different.

13. A compound selected from the group consisting of:

1-{3-Amino-1-methyl-4-[4-(3-phenyl-ureido)-phenyl]-1H-pyrazolo[3,4-b]pyridin-6-yl}-cyclopropanecarboxylic acid ethyl ester;

1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid ethyl ester;

1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid;

1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid methylamide;

1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid ethylamide;

1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid isopropylamide;

1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid phenylamide;

1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid (2-morpholin-4-yl-ethyl)-amide;

1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid (2-dimethylamino-ethyl)-amide;

1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid dimethylamide;

1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid diethylamide;

1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid cyclopropylamide;

1-(4-{3-Amino-1-methyl-6-[1-(pyrrolidine-1-carbonyl)-cyclopropyl]-1H-pyrazolo[3,4-b]pyridin-4-yl}-phenyl)-3-(3-trifluoromethyl-phenyl)-urea;

1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid (2-hydroxy-ethyl)-amide;

1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid amide;

1-(3-Amino-1-methyl-4-{3-[3-(3-trifluoromethyl-phenyl)-ureido]-phenyl}-1H-pyrazolo[3,4-b]pyridin-6-yl)-cyclopropanecarboxylic acid ethyl ester;

1-(3-Amino-1-methyl-4-{3-[3-(3-trifluoromethyl-phenyl)-ureido]-phenyl}-1H-pyrazolo[3,4-b]pyridin-6-yl)-cyclopropanecarboxylic acid;

1-(3-Amino-1-methyl-4-{3-[3-(3-trifluoromethyl-phenyl)-ureido]-phenyl}-1H-pyrazolo[3,4-b]pyridin-6-yl)-cyclopropanecarboxylic acid methylamide;

1-(3-Amino-1-methyl-4-{3-[3-(3-trifluoromethyl-phenyl)-ureido]-phenyl}-1H-pyrazolo[3,4-b]pyridin-6-yl)-cyclopropanecarboxylic acid dimethylamide;

1-(3-Amino-1-methyl-4-{3-[3-(3-trifluoromethyl-phenyl)-ureido]-phenyl}-1H-pyrazolo[3,4-b]pyridin-6-yl)-cyclopropanecarboxylic acid cyclopropylamide;

1-(3-Amino-4-{4-[3-(2-fluoro-5-methyl-phenyl)-ureido]-phenyl}-1-methyl-1H-pyrazolo[3,4-b]pyridin-6-yl)-cyclopropanecarboxylic acid ethyl ester;

1-(3-Amino-4-{4-[3-(2-fluoro-5-methyl-phenyl)-ureido]-phenyl}-1-methyl-1H-pyrazolo[3,4-b]pyridin-6-yl)-cyclopropanecarboxylic acid;

1-(3-Amino-4-{4-[3-(2-fluoro-5-methyl-phenyl)-ureido]-phenyl}-1-methyl-1H-pyrazolo[3,4-b]pyridin-6-yl)-cyclopropanecarboxylic acid methylamide;

1-(4-{3-Amino-1-methyl-6-[1-(pyrrolidine-1-carbonyl)-cyclopropyl]-1H-pyrazolo[3,4-b]pyridin-4-yl}-phenyl)-3-(2-fluoro-5-methyl-phenyl)-urea 1-(3-Amino-4-{4-[3-(2-fluoro-5-methyl-phenyl)-ureido]-phenyl}-1-methyl-1H-pyrazolo[3,4-b]pyridin-6-yl)-cyclopropanecarboxylic acid dimethylamide;

1-(3-Amino-4-{4-[3-(2-fluoro-5-methyl-phenyl)-ureido]-phenyl}-1-methyl-1H-pyrazolo[3,4-b]pyridin-6-yl)-cyclopropanecarboxylic acid cyclopropylamide;

1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid diisopropylamide;

1-[4-(3-Amino-6-cyclopropyl-1-methyl-1H-pyrazolo[3,4-b]pyridin-4-yl)-phenyl]-3-(3-trifluoromethyl-phenyl)-urea;

1-[4-(3-Amino-6-cyclobutyl-1-methyl-1H-pyrazolo[3,4-b]pyridin-4-yl)-phenyl]-3-(3-trifluoromethyl-phenyl)-urea;

1-[4-(3-Amino-6-cyclohexyl-1-methyl-1H-pyrazolo[3,4-b]pyridin-4-yl)-phenyl]-3-(3-trifluoromethyl-phenyl)-urea;

1-{4-[3-Amino-1-methyl-6-(2-phenyl-cyclopropyl)-1H-pyrazolo[3,4-b]pyridin-4-yl]-phenyl}-3-(3-trifluoromethyl-phenyl)-urea;

[3-(3-Amino-1-methyl-4-{4-[3-(3-trifluoromethyl-phenyl)-ureido]-phenyl}-1H-pyrazolo[3,4-b]pyridin-6-yl)-2,2-dimethyl-cyclobutyl]-acetic acid methyl ester;

[3-(3-Amino-1-methyl-4-{4-[3-(3-trifluoromethyl-phenyl)-ureido]-phenyl}-1H-pyrazolo[3,4-b]pyridin-6-yl)-2,2-dimethyl-cyclobutyl]-acetic acid;

2-[3-(3-Amino-1-methyl-4-{4-[3-(3-trifluoromethyl-phenyl)-ureido]-phenyl}-1H-pyrazolo[3,4-b]pyridin-6-yl)-2,2-dimethyl-cyclobutyl]-N,N-dimethyl-acetamide; and 2-[3-(3-Amino-1-methyl-4-{4-[3-(3-trifluoromethyl-phenyl)-ureido]-phenyl}-1H-pyrazolo[3,4-b]pyridin-6-yl)-2,2-dimethyl-cyclobutyl]-N-cyclopropyl-acetamide.

14. A method of preparing a compound of formula (I) according to claim 1, comprising reacting a compound of formula 6:

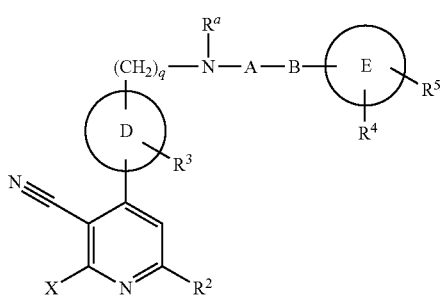

6 in which X represents a leaving group and A, B, D, E, $R^a$, $R^2$, $R^3$, $R^4$, $R^5$ and q are as defined for the compound of formula (I), with a substituted hydrazine of formula 6':

$H_2N-NHR^1$, 6' in which $R^1$ is as defined for the compound of formula (I), thereby providing a compound of formula (I):

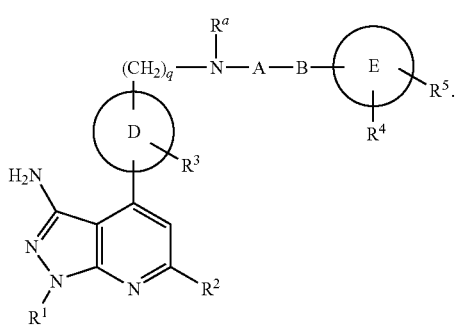

I

15. A method of preparing a compound of formula (I) according to claim 1, comprising reacting a compound of formula 10:

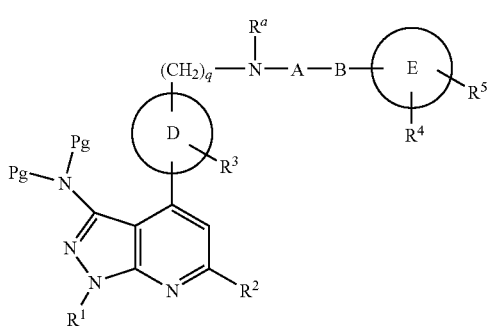

10 in which Pg represents a protecting group, and A, B, D, E, $R^a$, $R^1$, $R^2$, $R^3$, $R^4$, $R^5$ and q are as defined for the compound of formula (I), to be deprotected, thereby providing a compound of formula (I):

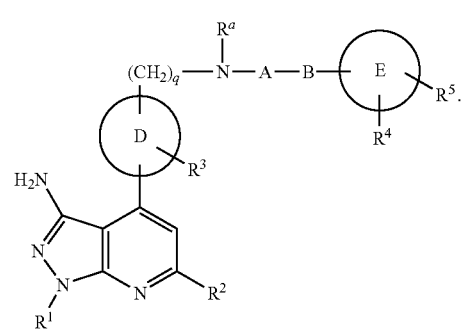

I

16. A method of preparing a compound of formula (I) according to claim 1, comprising reacting a compound of formula 11:

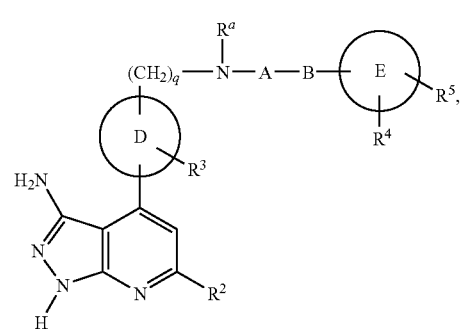

11 in which A, B, D, E, $R^a$, $R^2$, $R^3$, $R^4$, $R^5$ and q are as defined for the compound of formula (I), with a compound of formula 11':

X'—$R^1$ 11', in which $R^1$ is defined as for the compound of formula (I), and X' is a leaving group thereby providing a compound of general formula (I):

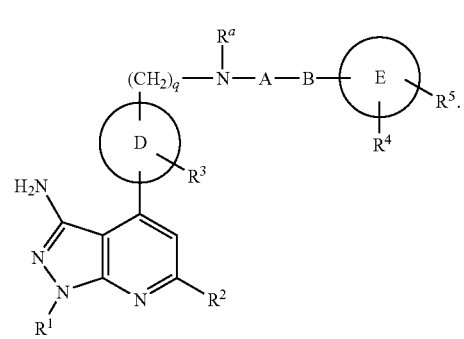

I

17. A method of preparing a compound of formula (I) according to claim 1, comprising reacting a compound of formula Ib:

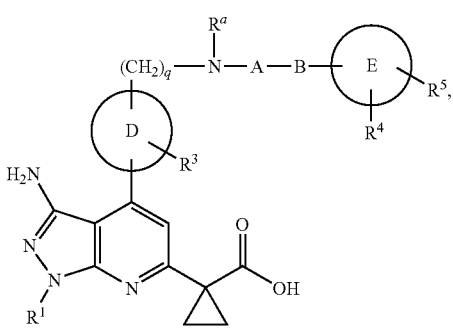

in which A, B, D, E, $R^a$, $R^1$, $R^3$, $R^4$, $R^5$ and q are as defined for the compound of formula (I),
with a compound of general formula 14:

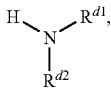

in which $R^{d1}$ and $R^{d2}$ are as defined for the compound of formula (I), thereby providing a compound of formula Ic:

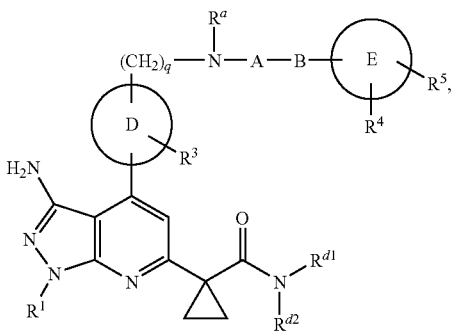

in which A, B, D, E, $R^a$, $R^1$, $R^3$, $R^4$, $R^5$, $R^{d1}$, $R^{d2}$ and q are as defined for the compound of formula (I).

18. A pharmaceutical composition comprising a compound of formula (I) according to claim 1, or a pharmaceutically acceptable salt or an N-oxide thereof, and a pharmaceutically-acceptable diluent or carrier.

19. The compound according to claim 1, wherein $R^2$ represents a $C_3$-$C_6$-cycloalkyl.

20. The compound according to claim 1, wherein $R^2$ represents a $C_3$-cycloalkyl.

21. The compound according to claim 1, or a pharmaceutically acceptable salt thereof.

22. The compound according to claim 1, or a pharmaceutically acceptable N-oxide thereof.

23. A compound selected from the group consisting of:
1-{3-Amino-1-methyl-4-[4-(3-phenyl-ureido)-phenyl]-1H-pyrazolo[3,4-b]pyridin-6-yl}-cyclopropanecarboxylic acid ethyl ester;
1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid ethyl ester;
1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid;
1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid methylamide;
1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid ethylamide;
1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid isopropylamide;
1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid phenylamide;
1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid (2-morpholin-4-yl-ethyl)-amide;
1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid (2-dimethylamino-ethyl)-amide;
1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid dimethylamide;
1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid diethylamide;
1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid cyclopropylamide;
1-(4-{3-Amino-1-methyl-6-[1-(pyrrolidine-1-carbonyl)-cyclopropyl]-1H-pyrazolo[3,4-b]pyridin-4-yl}-phenyl)-3-(3-trifluoromethyl-phenyl)-urea;
1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid (2-hydroxy-ethyl)-amide;
1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid amide;
1-(3-Amino-1-methyl-4-{3-[3-(3-trifluoromethyl-phenyl)-ureido]-phenyl}-1H-pyrazolo[3,4-b]pyridin-6-yl)-cyclopropanecarboxylic acid ethyl ester;
1-(3-Amino-1-methyl-4-{3-[3-(3-trifluoromethyl-phenyl)-ureido]-phenyl}-1H-pyrazolo[3,4-b]pyridin-6-yl)-cyclopropanecarboxylic acid;
1-(3-Amino-1-methyl-4-{3-[3-(3-trifluoromethyl-phenyl)-ureido]-phenyl}-1H-pyrazolo[3,4-b]pyridin-6-yl)-cyclopropanecarboxylic acid methylamide;
1-(3-Amino-1-methyl-4-{3-[3-(3-trifluoromethyl-phenyl)-ureido]-phenyl}-1H-pyrazolo[3,4-b]pyridin-6-yl)-cyclopropanecarboxylic acid dimethylamide;
1-(3-Amino-1-methyl-4-{3-[3-(3-trifluoromethyl-phenyl)-ureido]-phenyl}-1H-pyrazolo[3,4-b]pyridin-6-yl)-cyclopropanecarboxylic acid cyclopropylamide;
1-(3-Amino-4-{4-[3-(2-fluoro-5-methyl-phenyl)-ureido]-phenyl}-1-methyl-1H-pyrazolo[3,4-b]pyridin-6-yl)-cyclopropanecarboxylic acid ethyl ester;
1-(3-Amino-4-{4-[3-(2-fluoro-5-methyl-phenyl)-ureido]-phenyl}-1-methyl-1H-pyrazolo[3,4-b]pyridin-6-yl)-cyclopropanecarboxylic acid;

1-(3-Amino-4-{4-[3-(2-fluoro-5-methyl-phenyl)-ureido]-phenyl}-1-methyl-1H-pyrazolo[3,4-b]pyridin-6-yl)-cyclopropanecarboxylic acid methylamide;
1-(4-{3-Amino-1-methyl-6-[1-(pyrrolidine-1-carbonyl)-cyclopropyl]-1H-pyrazolo[3,4-b]pyridin-4-yl}-phenyl)-3-(2-fluoro-5-methyl-phenyl)-urea
1-(3-Amino-4-{4-[3-(2-fluoro-5-methyl-phenyl)-ureido]-phenyl}-1-methyl-1H-pyrazolo[3,4-b]pyridin-6-yl)-cyclopropanecarboxylic acid dimethylamide;
1-(3-Amino-4-{4-[3-(2-fluoro-5-methyl-phenyl)-ureido]-phenyl}-1-methyl-1H-pyrazolo[3,4-b]pyridin-6-yl)-cyclopropanecarboxylic acid cyclopropylamide;
1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid diisopropylamide;
1-[4-(3-Amino-6-cyclopropyl-1-methyl-1H-pyrazolo[3,4-b]pyridin-4-yl)-phenyl]-3-(3-trifluoromethyl-phenyl)-urea;
1-[4-(3-Amino-6-cyclobutyl-1-methyl-1H-pyrazolo[3,4-b]pyridin-4-yl)-phenyl]-3-(3-trifluoromethyl-phenyl)-urea;
1-[4-(3-Amino-6-cyclohexyl-1-methyl-1H-pyrazolo[3,4-b]pyridin-4-yl)-phenyl]-3-(3-trifluoromethyl-phenyl)-urea;
1-{4-[3-Amino-1-methyl-6-(2-phenyl-cyclopropyl)-1H-pyrazolo[3,4-b]pyridin-4-yl]-phenyl}-3-(3-trifluoromethyl-phenyl)-urea;
[3-(3-Amino-1-methyl-4-{4-[3-(3-trifluoromethyl-phenyl)-ureido]-phenyl}-1H-pyrazolo[3,4-b]pyridin-6-yl)-2,2-dimethyl-cyclobutyl]-acetic acid methyl ester;
[3-(3-Amino-1-methyl-4-{4-[3-(3-trifluoromethyl-phenyl)-ureido]-phenyl}-1H-pyrazolo[3,4-b]pyridin-6-yl)-2,2-dimethyl-cyclobutyl]-acetic acid;
2-[3-(3-Amino-1-methyl-4-{4-[3-(3-trifluoromethyl-phenyl)-ureido]-phenyl}-1H-pyrazolo[3,4-b]pyridin-6-yl)-2,2-dimethyl-cyclobutyl]-N,N-dimethyl-acetamide; and
2-[3-(3-Amino-1-methyl-4-{4-[3-(3-trifluoromethyl-phenyl)-ureido]-phenyl}-1H-pyrazolo[3,4-b]pyridin-6-yl)-2,2-dimethyl-cyclobutyl]-N-cyclopropyl-acetamide
and pharmaceutically acceptable salts and N-oxides thereof.

24. A pharmaceutical composition comprising a compound of claim 23, or a pharmaceutically acceptable salt or an N-oxide thereof, and a pharmaceutically-acceptable diluent or carrier.

25. A pharmaceutical composition comprising a compound of claim 13, and a pharmaceutically-acceptable diluent or carrier.

26. A method according to claim 14, comprising reacting a compound of formula 6:

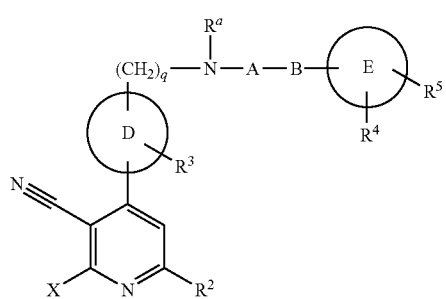

in which X represents OTf, Cl, F, OAc, or OMe; and A, B, D, E, $R^a$, $R^2$, $R^3$, $R^4$, $R^5$ and q are as defined for the compound of formula (I), with a substituted hydrazine of formula 6':

in which $R^1$ is as defined for the compound of formula (I), thereby providing a compound of formula (I):

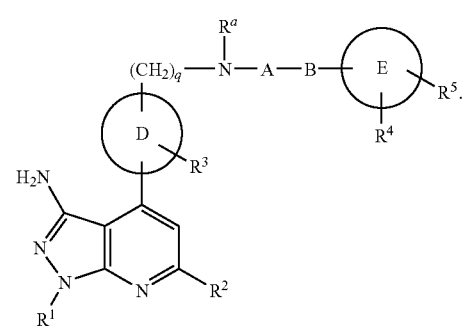

27. A method according to claim 15, comprising reacting a compound of formula 10:

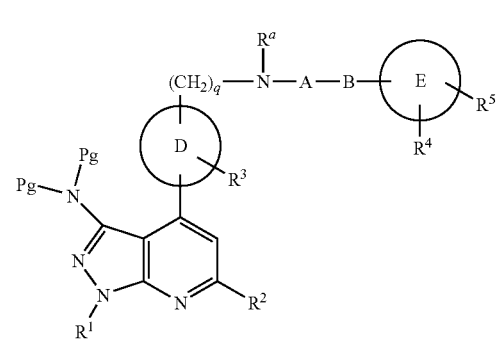

in which

represents a phthalimide-protected amine of formula 10':

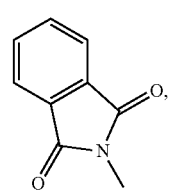

and A, B, D, E, $R^a$, $R^1$, $R^2$, $R^3$, $R^4$, $R^5$ and q are as defined for the compound of formula (I), to be deprotected,
thereby providing a compound of formula (I):

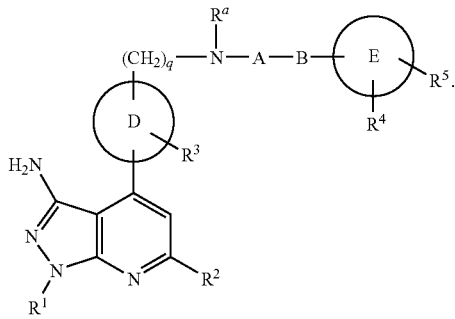

28. A method according to claim 15, comprising reacting a compound of formula 10:

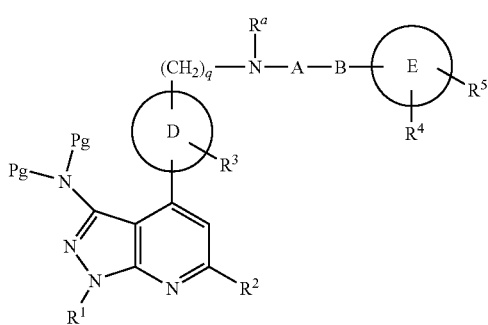

in which

represents a phthalimide-protected amine of formula 10':

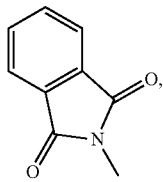

and A, B, D, E, $R^a$, $R^1$, $R^2$, $R^3$, $R^4$, $R^5$ and q are as defined for the compound of formula (I), with hydrazine,
thereby providing a compound of formula (I):

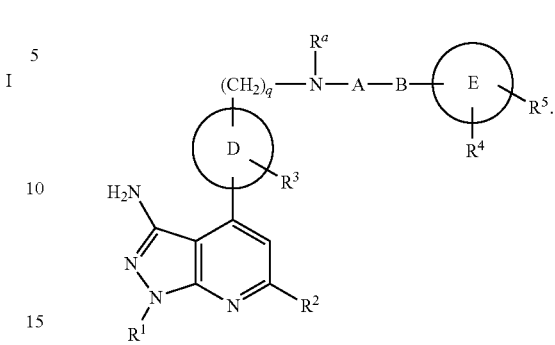

29. A method according to claim 16, comprising reacting a compound of formula II:

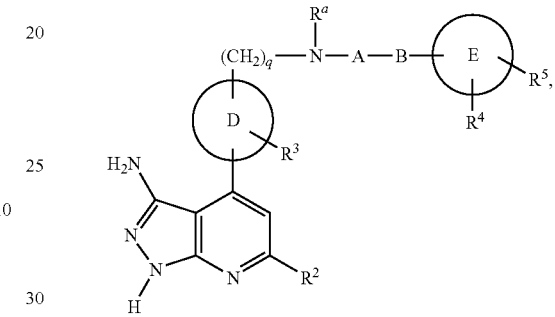

in which A, B, D, E, $R^a$, $R^2$, $R^3$, $R^4$, $R^5$ and q are as defined for the compound of formula (I),
with a compound of formula 11':

$$X'—R^1 \qquad 11',$$

in which $R^1$ is defined as for the compound of formula (I), and X' is OTf, Cl, Br, I, OMs (methanesulfonyl), or OAc,
thereby providing a compound of formula (I):

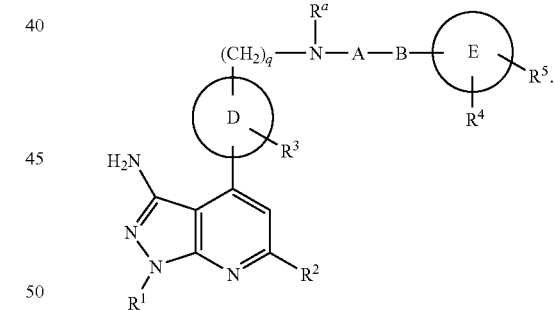

30. A method according to claim 17, comprising reacting a compound of formula Ib:

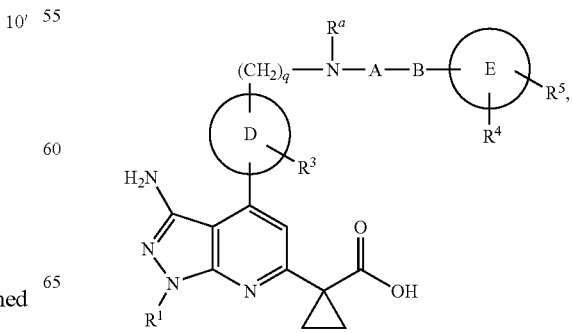

in which A, B, D, E, $R^a$, $R^1$, $R^3$, $R^4$, $R^5$ and q are as defined for the compound of formula (I),
with a compound of formula 14:

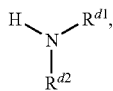
14 in which $R^{d1}$ and $R^{d2}$ are as defined for the compound of formula (I),
in the presence of a coupling agent,
thereby providing a compound of formula Ic:

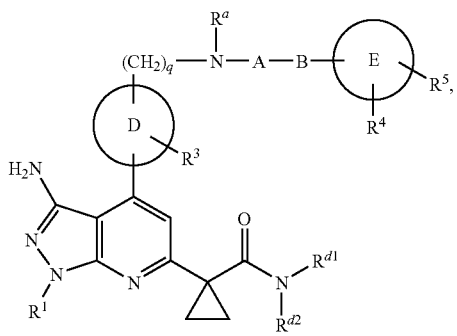
Ic in which A, B, D, E, $R^a$, $R^1$, $R^3$, $R^4$, $R^5$, $R^{d1}$, and $R^{d2}$ and q are as defined for the compound of formula (I).

31. A method of claim 17, comprising reacting a compound of formula Ib:

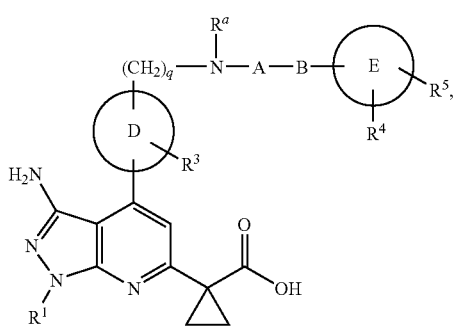
Ib in which A, B, D, E, $R^a$, $R^1$, $R^3$, $R^4$, $R^5$ and q are as defined for the compound of formula (I),
with a compound of formula 14:

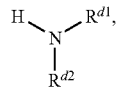
14 in which $R^{d1}$ and $R^{d2}$ are as defined for the compound of formula (I),
in the presence of T3P, thereby providing a compound of formula Ic:

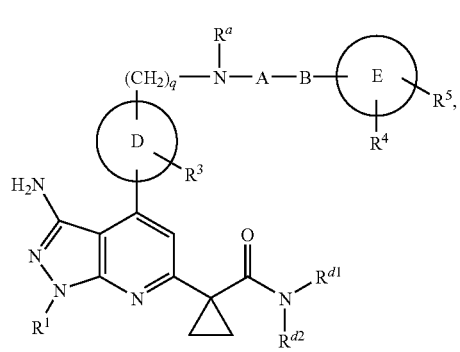
Ic in which A, B, D, E, $R^a$, $R^1$, $R^3$, $R^4$, $R^5$, $R^{d1}$, $R^{d2}$ and q are as defined for the compound of formula (I).

32. A pharmaceutical composition comprising a compound of claim 2, or a pharmaceutically acceptable salt or an N-oxide thereof, and a pharmaceutically-acceptable diluent or carrier.

33. A pharmaceutical composition comprising a compound of claim 3, or a pharmaceutically acceptable salt or an N-oxide thereof, and a pharmaceutically-acceptable diluent or carrier.

34. A pharmaceutical composition comprising a compound of claim 4, or a pharmaceutically acceptable salt or an N-oxide thereof, and a pharmaceutically-acceptable diluent or carrier.

35. A pharmaceutical composition comprising a compound of claim 12, or a pharmaceutically acceptable salt or an N-oxide thereof, and a pharmaceutically-acceptable diluent or carrier.

* * * * *

UNITED STATES PATENT AND TRADEMARK OFFICE
CERTIFICATE OF CORRECTION

PATENT NO.        : 7,825,114 B2                                             Page 1 of 1
APPLICATION NO.   : 11/761621
DATED             : November 2, 2010
INVENTOR(S)       : Ingo Hartung et al.

It is certified that error appears in the above-identified patent and that said Letters Patent is hereby corrected as shown below:

Column 137, line 46 reads "cycloalkyl, or for a $C(O)R^c$ and —$C(O)NR^{d1}R^{d2}$,"
should read --cycloalkyl, $C(O)R^c$ and —$C(O)NR^{d1}R^{d2}$,--.

Column 138, line 7 reads "represents —$C(O)R^b$ or is selected from the preferably"
should read --represents —$C(O)R^b$ or is selected from the group--.

Column 139, line 53 reads "cycloalkyl, or for a $C(O)R^c$ and —$C(O)NR^{d1}R^{d2}$ group,"
should read --cycloalkyl, $C(O)R^c$ and —$C(O)NR^{d1}R^{d2}$ group,--.

Column 142, line 33 reads "cycloalkyl, $C(O)R^c$ of and —$C(O)NR^{d1}R^{d2}$ group,"
should read --cycloalkyl, $C(O)R^c$ and —$C(O)NR^{d1}R^{d2}$ group,--.

Column 155, line 34 reads "31. A method of claim 17, comprising"
should read --31. A method according to claim 17, comprising--.

Signed and Sealed this
Thirteenth Day of March, 2012

David J. Kappos
*Director of the United States Patent and Trademark Office*